(12) United States Patent
Gabara

(10) Patent No.: US 8,008,070 B2
(45) Date of Patent: Aug. 30, 2011

(54) USING COULOMB FORCES TO STUDY CHARATERISTICS OF FLUIDS AND BIOLOGICAL SAMPLES

(75) Inventor: Thaddeus John Gabara, Murray Hill, NJ (US)

(73) Assignee: MetaMEMS Corp., Murray Hill, NJ (US)

( * ) Notice: Subject to any disclaimer, the term of this patent is extended or adjusted under 35 U.S.C. 154(b) by 853 days.

(21) Appl. No.: 11/952,984

(22) Filed: Dec. 7, 2007

(65) Prior Publication Data
US 2009/0148932 A1   Jun. 11, 2009

(51) Int. Cl.
*C12M 1/33* (2006.01)
(52) U.S. Cl. .................................................. 435/306.1
(58) Field of Classification Search ................ 435/306.1
See application file for complete search history.

(56) References Cited

U.S. PATENT DOCUMENTS

| | | | |
|---|---|---|---|
| 4,228,527 A | | 10/1980 | Gerber et al. |
| 4,848,536 A | * | 7/1989 | Machida |
| 4,885,719 A | | 12/1989 | Brahmbhatt |
| 4,947,228 A | | 8/1990 | Gabara |
| 5,095,401 A | * | 3/1992 | Zavracky |
| 5,298,800 A | | 3/1994 | Dunlop |
| 5,317,202 A | * | 5/1994 | Waizman |
| 5,355,577 A | | 10/1994 | Cohn |
| 5,396,195 A | | 3/1995 | Gabara |
| 5,406,848 A | * | 4/1995 | Okada |
| 5,646,828 A | | 7/1997 | Degani et al. |
| 5,708,389 A | | 1/1998 | Gabara |
| 5,838,021 A | | 11/1998 | Ancona |
| 5,847,930 A | * | 12/1998 | Kazle |
| 6,141,260 A | | 10/2000 | Ahn et al. |
| 6,256,880 B1 | * | 7/2001 | Ulmer |
| 6,281,590 B1 | | 8/2001 | Gabara |
| 6,300,149 B1 | | 10/2001 | Smith |
| 6,465,336 B2 | | 10/2002 | Gabara |
| 6,597,048 B1 | | 7/2003 | Kan |

(Continued)

FOREIGN PATENT DOCUMENTS
JP  08-320231  12/1996
(Continued)

OTHER PUBLICATIONS
Appendix of specification, paragraphs [0231] to [0242], filed on Dec. 7, 2007.

(Continued)

*Primary Examiner* — Bobby Ramdhanie
(74) *Attorney, Agent, or Firm* — Thaddeus Gabara

(57) ABSTRACT

A LoC (Lab on a Chip) is described to analyze surface properties of fluid drops. Substrates with cavities near the edge are filled with fluids that have a contact angle greater than 90°. The surfaces of two different drops can be brought in contact with one another by using Coulomb forces. Several experiments can be carried out while the drops are in contact: the concentration of the fluid in each drop can be altered, tangential and normal forces can be applied to the contact surface, voltage differences across and current flow through the contact surface can be monitored. MEMS pumps can be used to mix reagents or buffers with the fluid to determine the protein concentration or to extract DNA from whole cells, respectively. Substrates holding optical components can be used to align fibers with either lasers or receivers. The alignment is automatic and controlled by a control unit.

21 Claims, 65 Drawing Sheets

U.S. PATENT DOCUMENTS

| | | |
|---|---|---|
| 6,638,627 B2 | 10/2003 | Potter |
| 6,724,609 B2 | 4/2004 | Sun |
| 6,798,120 B1 | 9/2004 | Fearing |
| 6,841,917 B2 | 1/2005 | Potter |
| 6,856,297 B1 | 2/2005 | Durham et al. |
| 6,995,039 B2 | 2/2006 | Harris |
| 7,217,582 B2 | 5/2007 | Potter |
| 7,225,674 B2 | 6/2007 | Clark |
| 7,250,826 B2 | 7/2007 | Gabara |
| 7,543,497 B2 | 6/2009 | Balogh |
| 7,555,950 B2 | 7/2009 | Ruohio et al. |
| 2001/0053565 A1 | 12/2001 | Khoury |
| 2004/0046618 A1 | 3/2004 | Sheen |
| 2004/0080456 A1 | 4/2004 | Tran |
| 2005/0196981 A1 | 9/2005 | Hashimoto |
| 2006/0065051 A1 | 3/2006 | Balogh |
| 2006/0122504 A1 | 6/2006 | Gabara |
| 2006/0201629 A1 | 9/2006 | Hashizume |
| 2007/0018739 A1 | 1/2007 | Gabara |
| 2007/0176704 A1 | 8/2007 | Gabara |
| 2007/0204706 A1 | 9/2007 | Kishimoto |
| 2009/0109595 A1 | 4/2009 | Herchen et al. |
| 2009/0115071 A1 | 5/2009 | Karashima et al. |

FOREIGN PATENT DOCUMENTS

| | | |
|---|---|---|
| JP | 2001-235329 | 2/2000 |

OTHER PUBLICATIONS

Wheeler, H., "Fundamental Limitations of Small Antennas", Pro. of the IRE, vol. 35, Issue 12, Dec. 1947, pp. 1479-1484.

Bohringer et al. "Computation Methods for Design and Control of MEMS Micromanipulator Arrays", Computing in Science and Eng., Jan.-Mar. 1997, (vol. 4, No. 1), pp. 17-29.

Cohn et al., "Microassembly Technologies for MEMS", Proc. SPIE Micromaching and Microfabrication, Sanata Clara, Ca. Sep. 21-22, 1998, pp. 164-178.

Liu, "Novel Electrostatic Repulsive Forces in MEMS Applications by Nonvolatile Charge Injection", The 15th IEEE Int. Conf. MEMS, 2002, p. 598-601.

Fearing, "Survey of sticking effects for micro parts handling", Intelligent Robots and Systems 95, Proc. 1995 IEEE/RSJ Inter, Conf. Aug. 5-9, 1995, pp. 212-217.

Academic Press Dictionary of Science and Technology, published 1992, credo reference (see the two attached NPL sheets).

Wakayama et al., Nanotechnology, 15, 2004, pp. 1446-1449, p. 14.

Nakajima et al., Applied Physics Letters 71, Jul. 3, 1997, pp. 353-355.

Electrical/Optical Issues in I/O CMOS Interfaces Gabara, T.J.; *Optical Interconnect Workshop, Oak Ridge National Laboratory*, Oak Ridge, TN, Nov. 8, 1999.—p. TJG 8.

\* cited by examiner

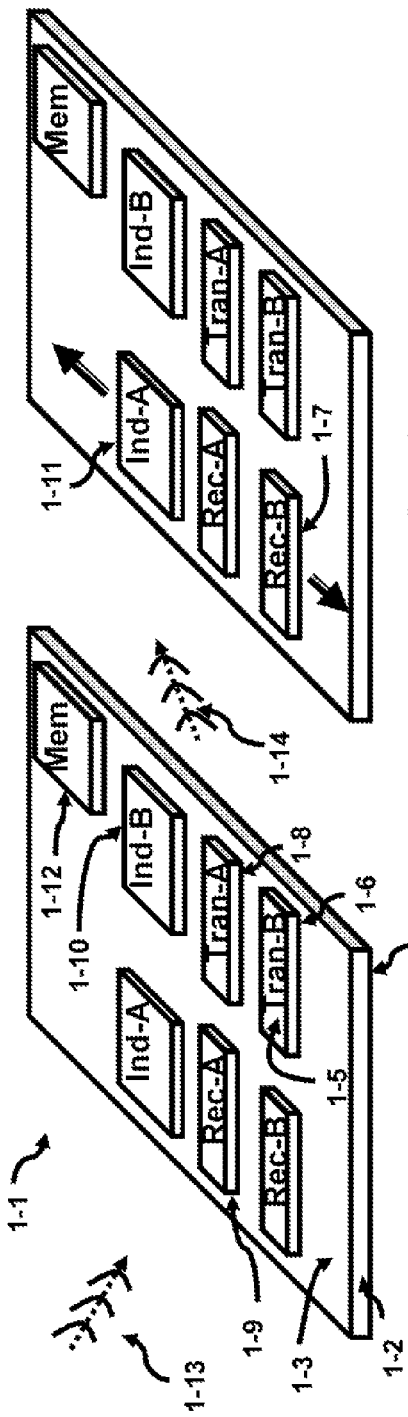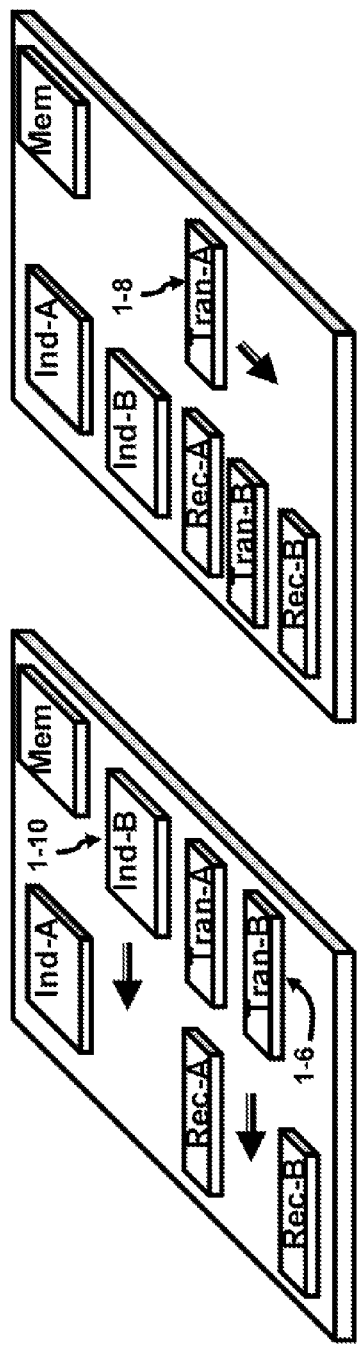

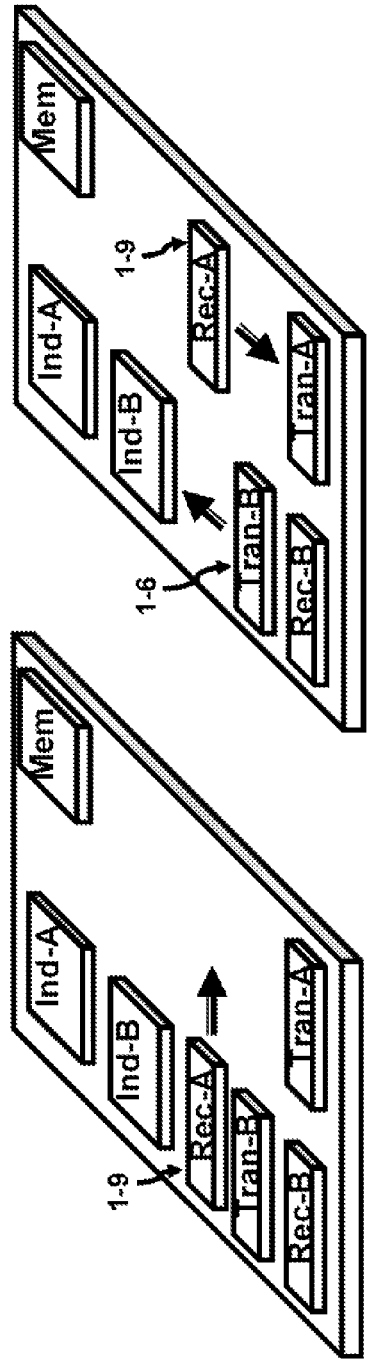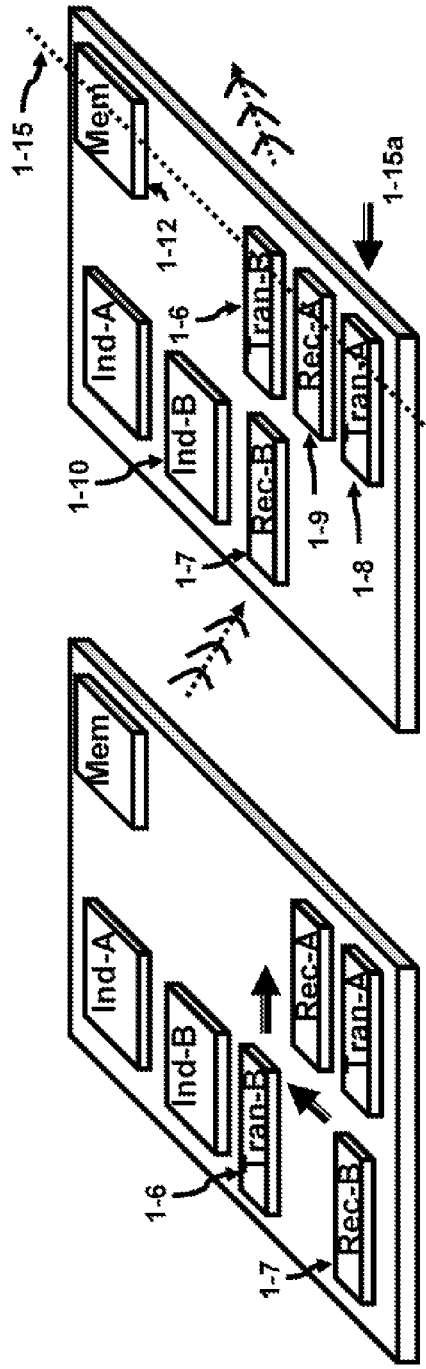

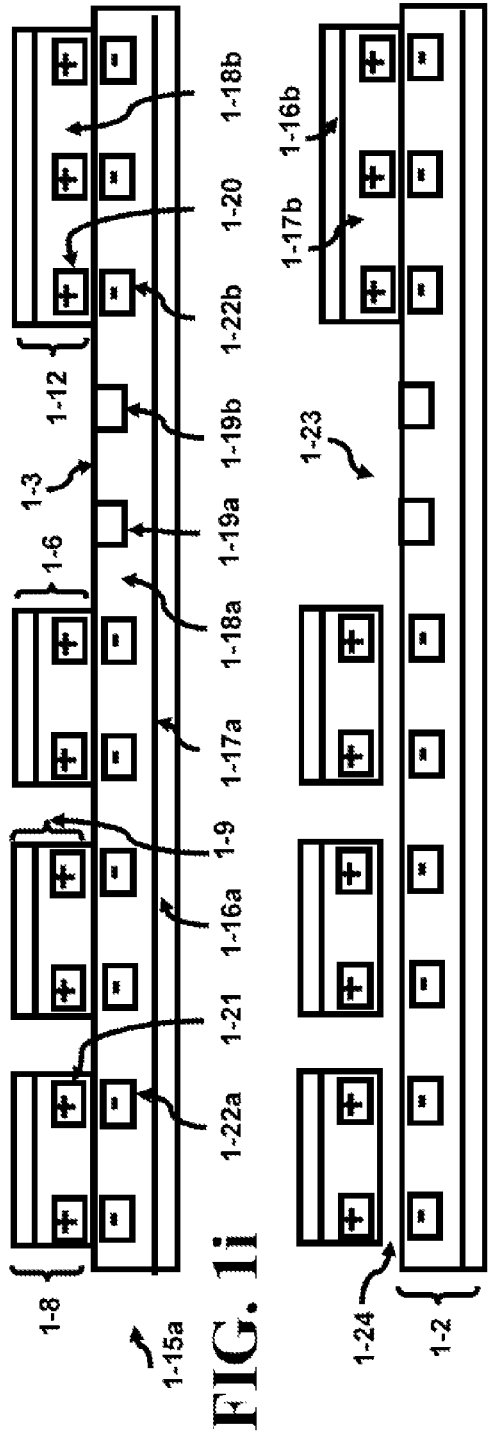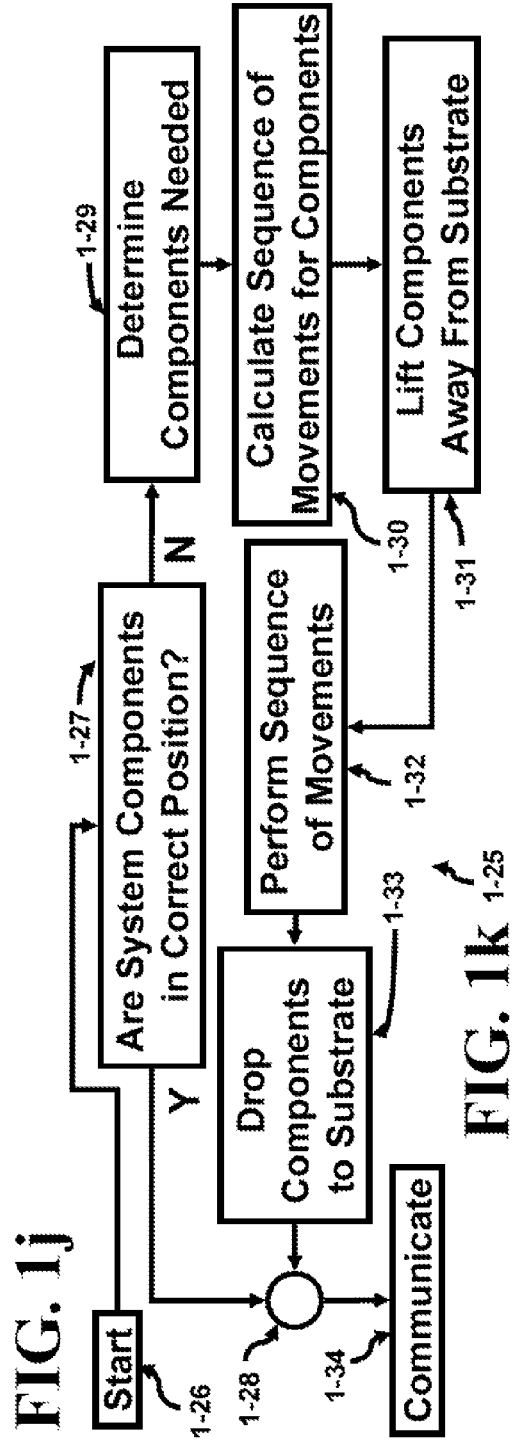

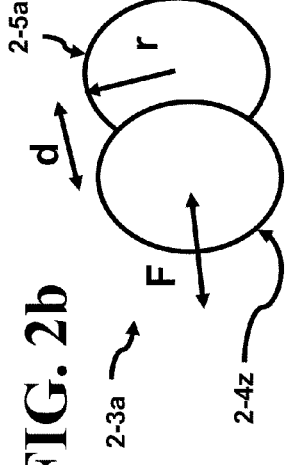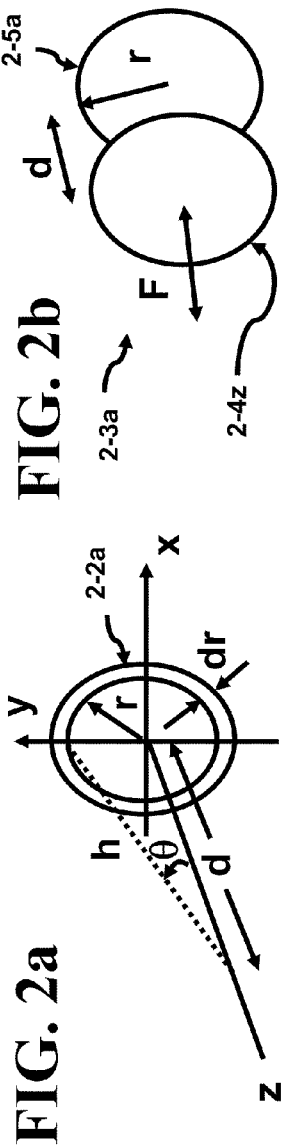

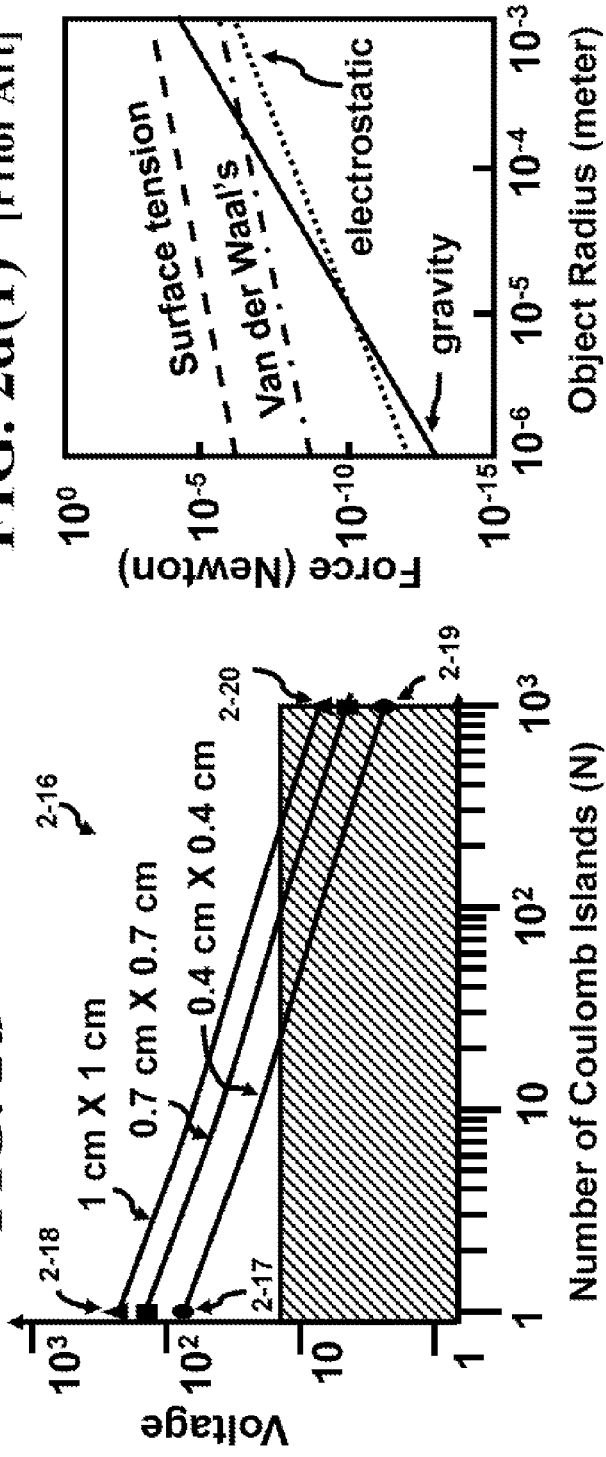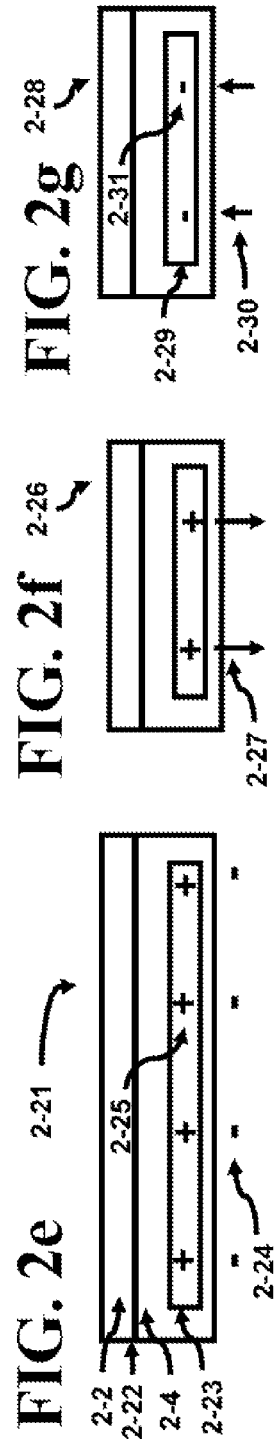

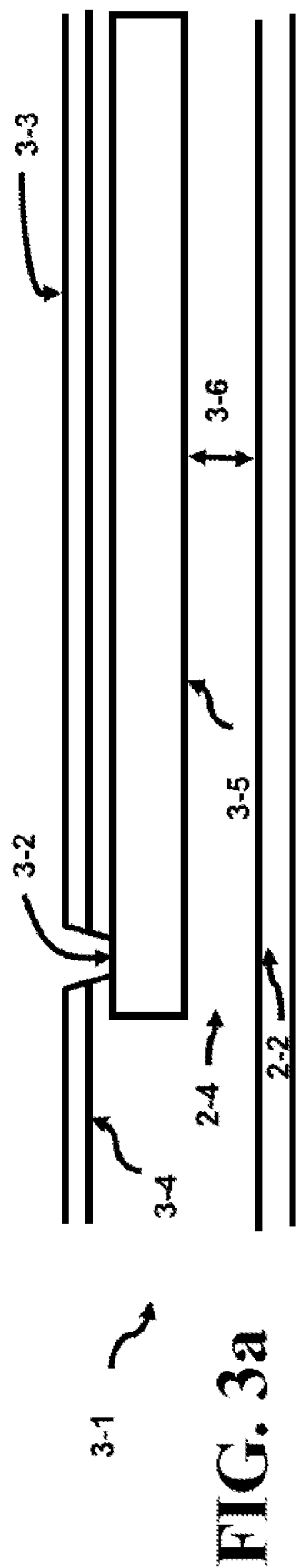
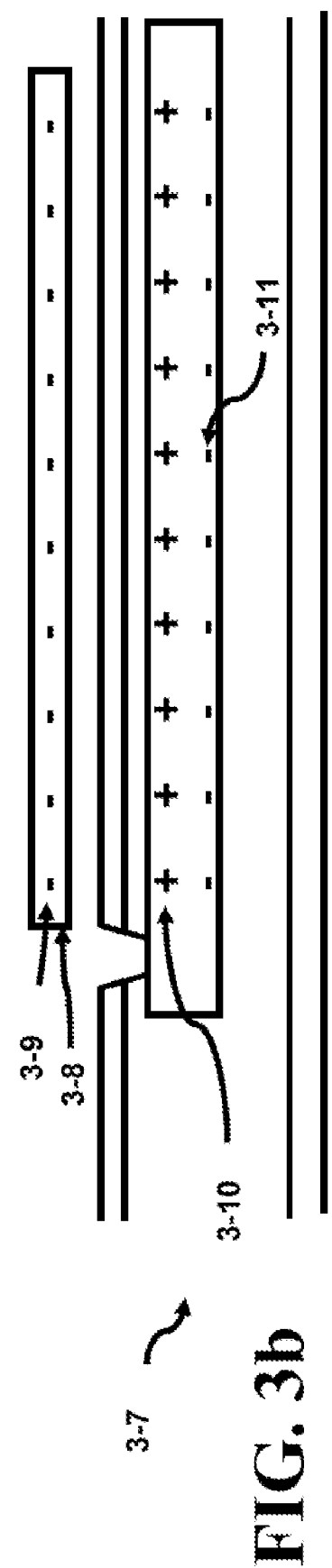

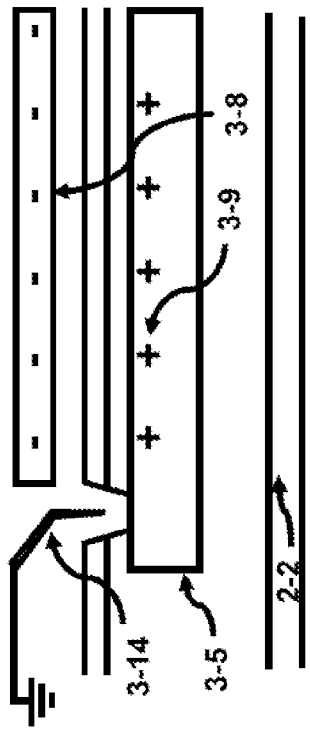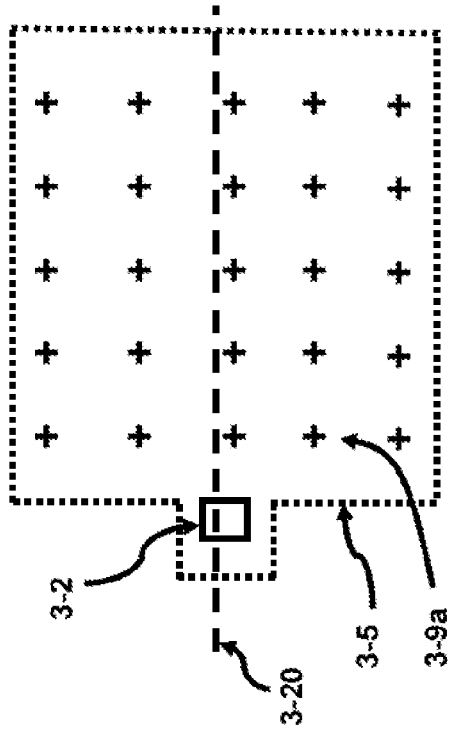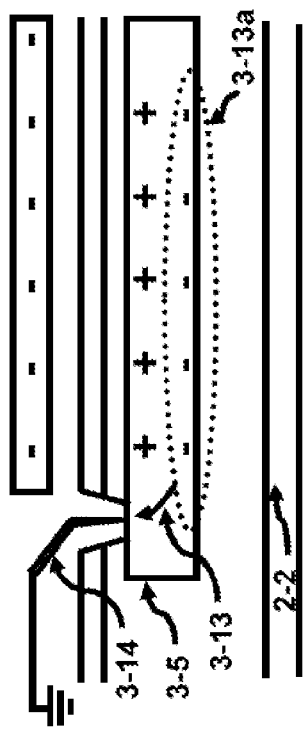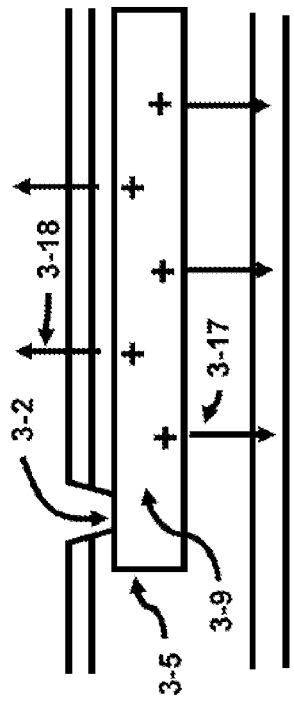

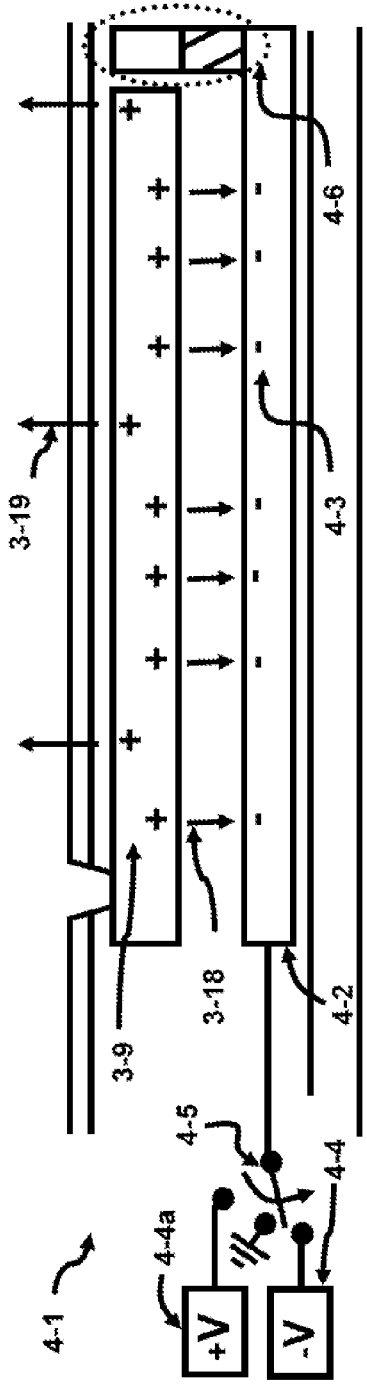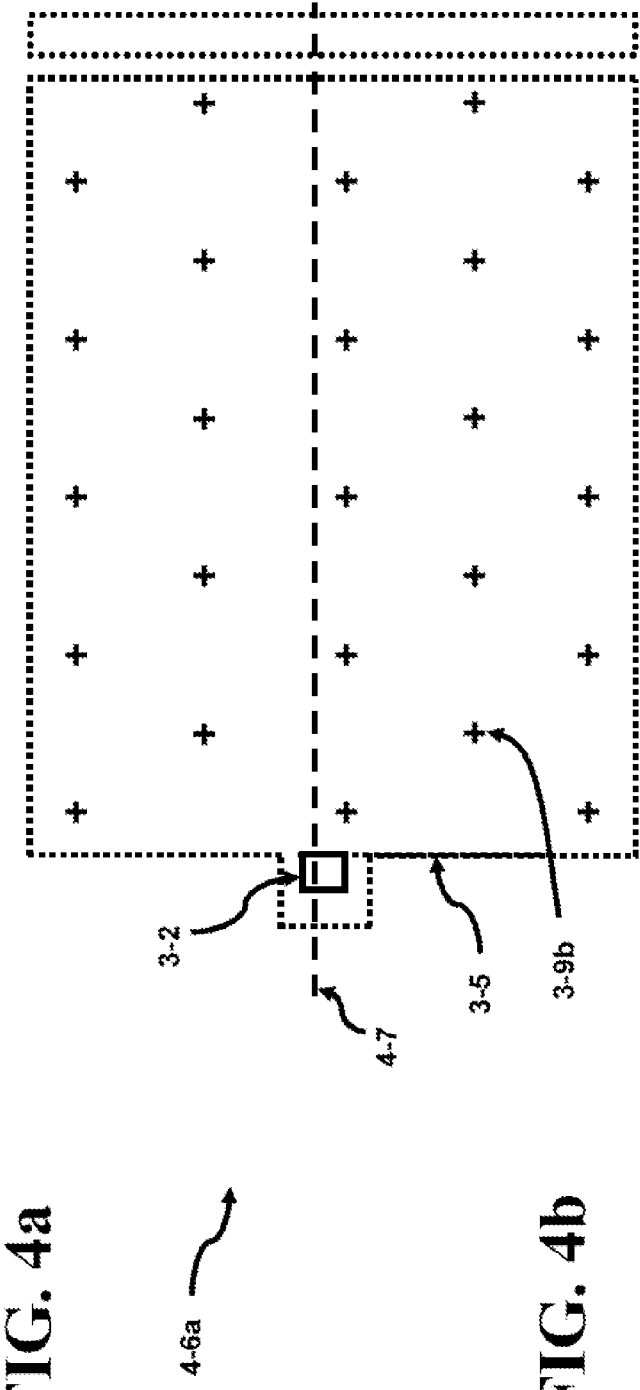
FIG. 4a
FIG. 4b

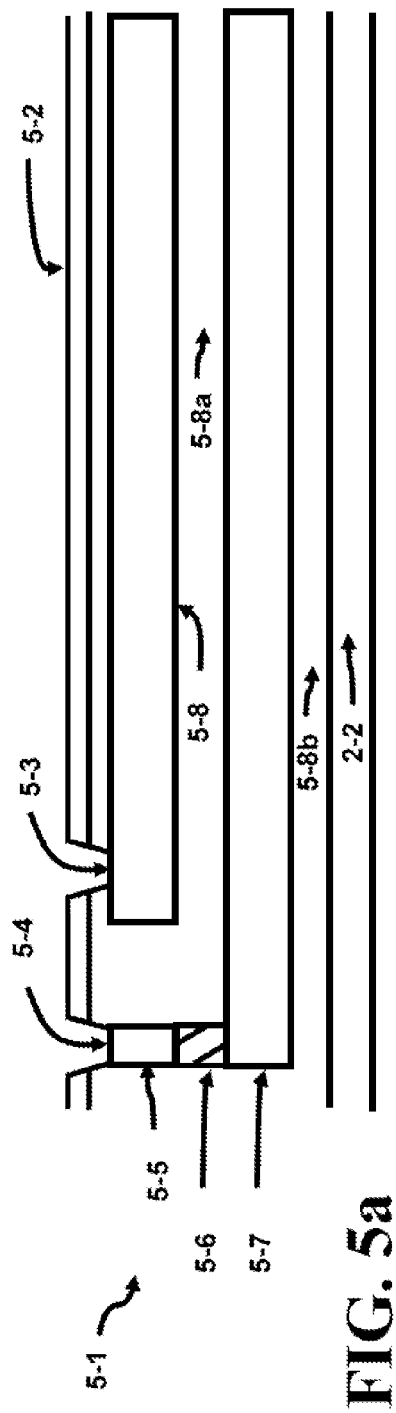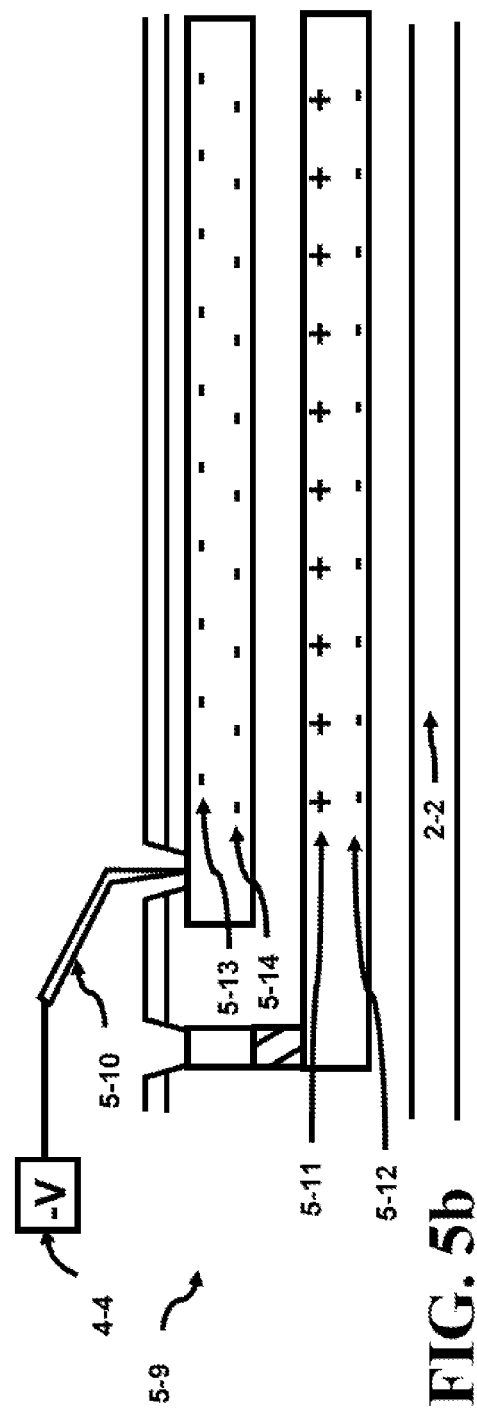
FIG. 5a
FIG. 5b

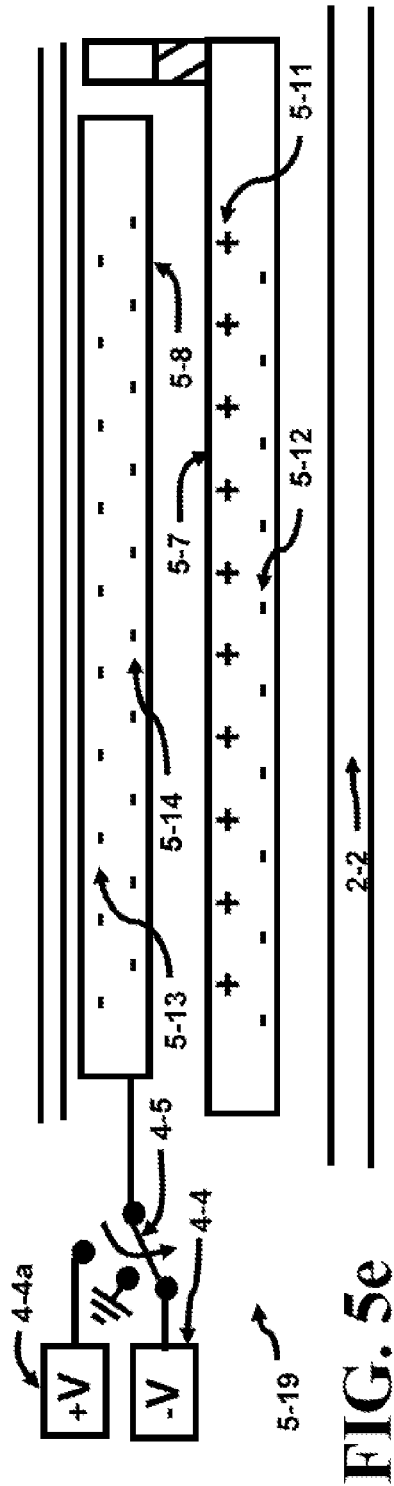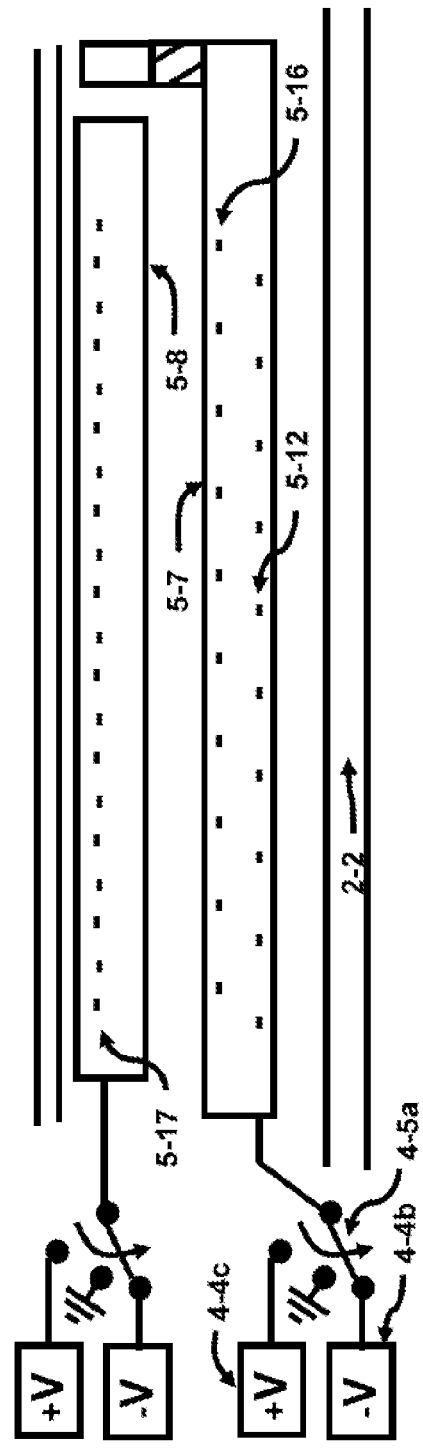
FIG. 5e
FIG. 5f

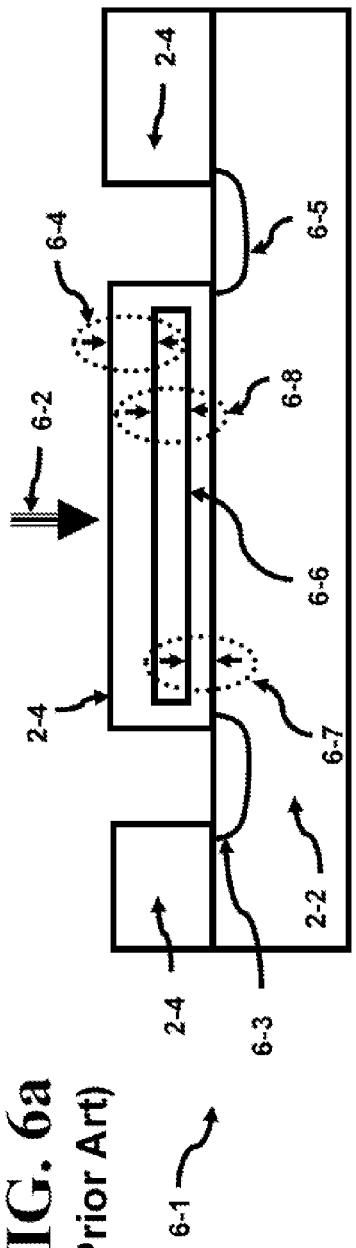
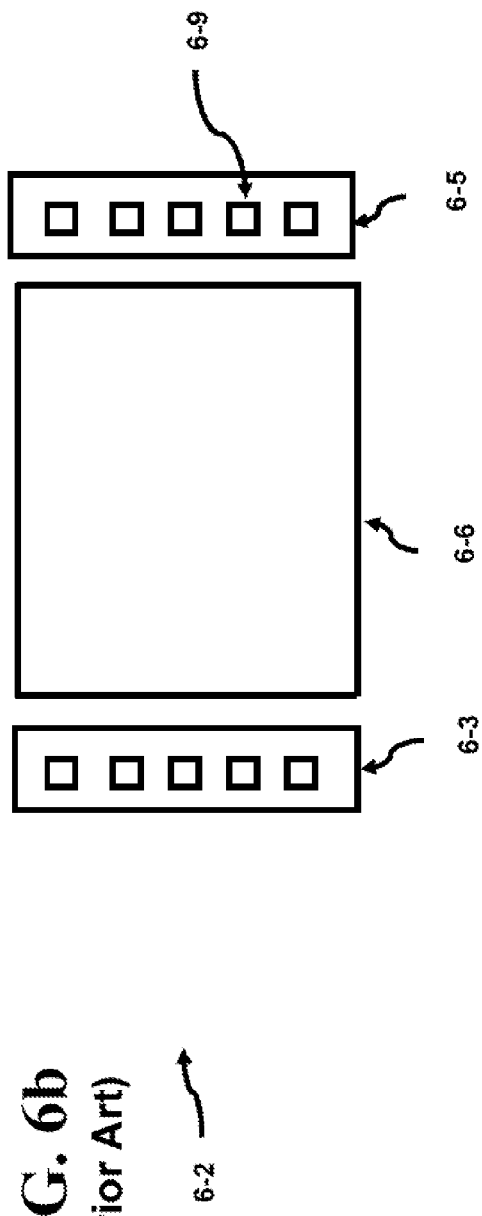
FIG. 6a (Prior Art)
FIG. 6b (Prior Art)

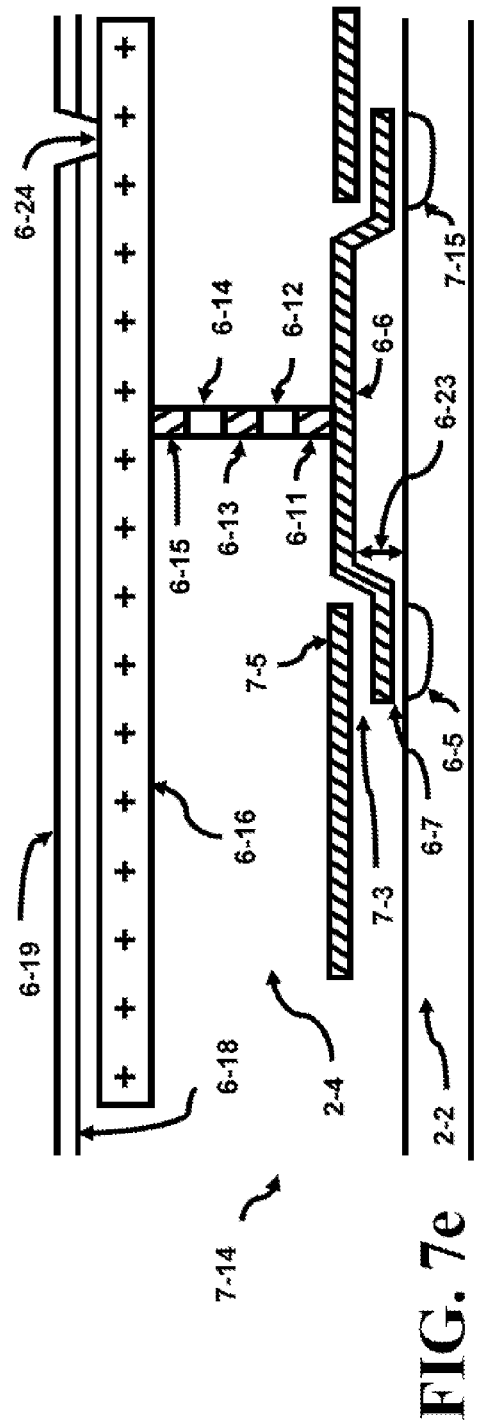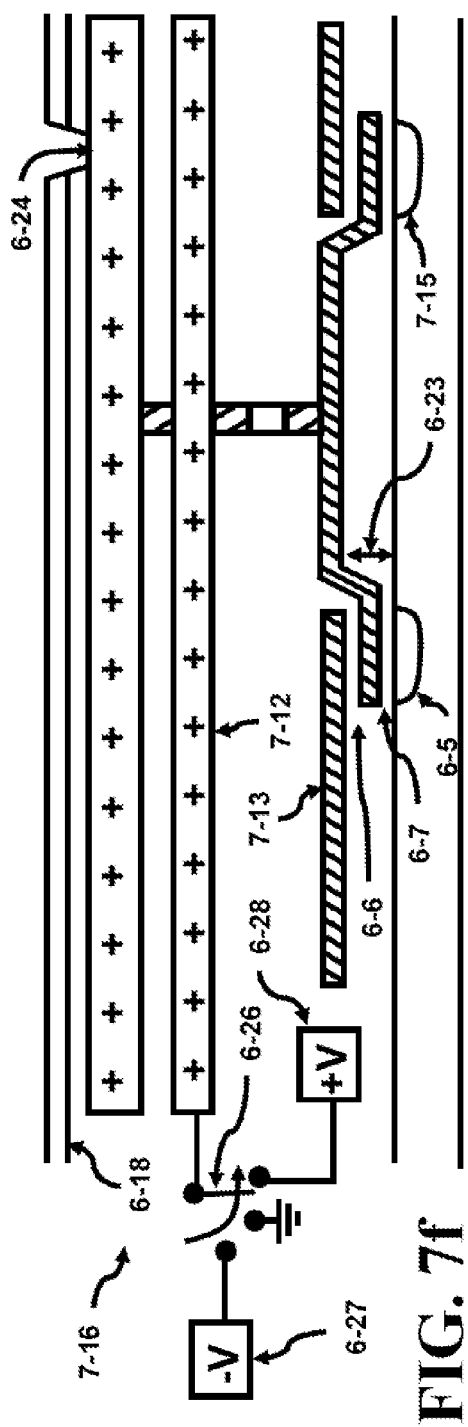

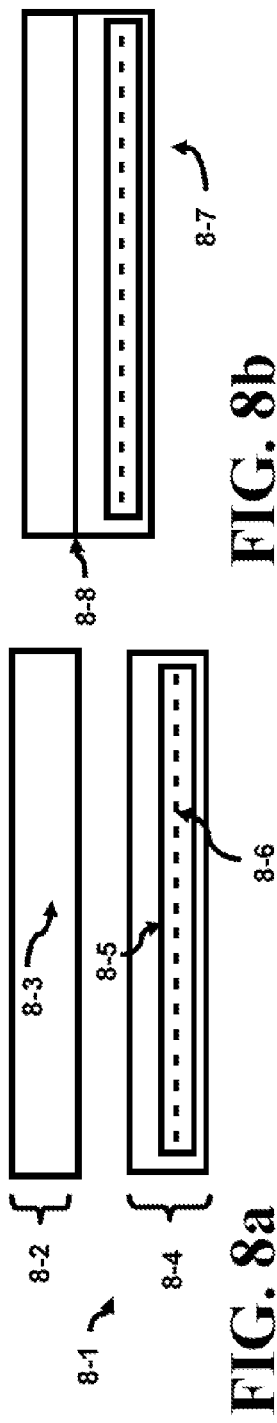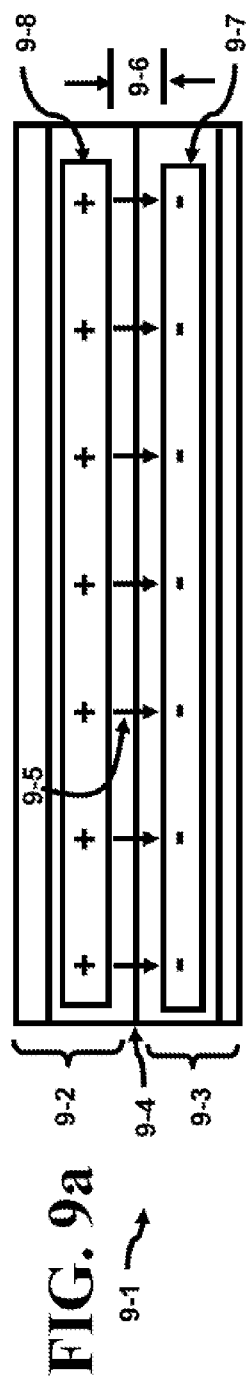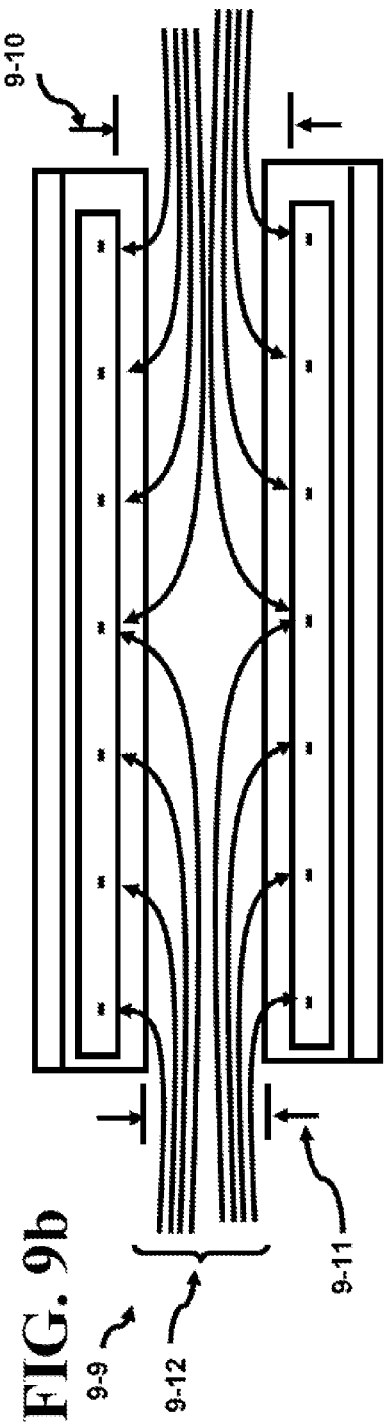

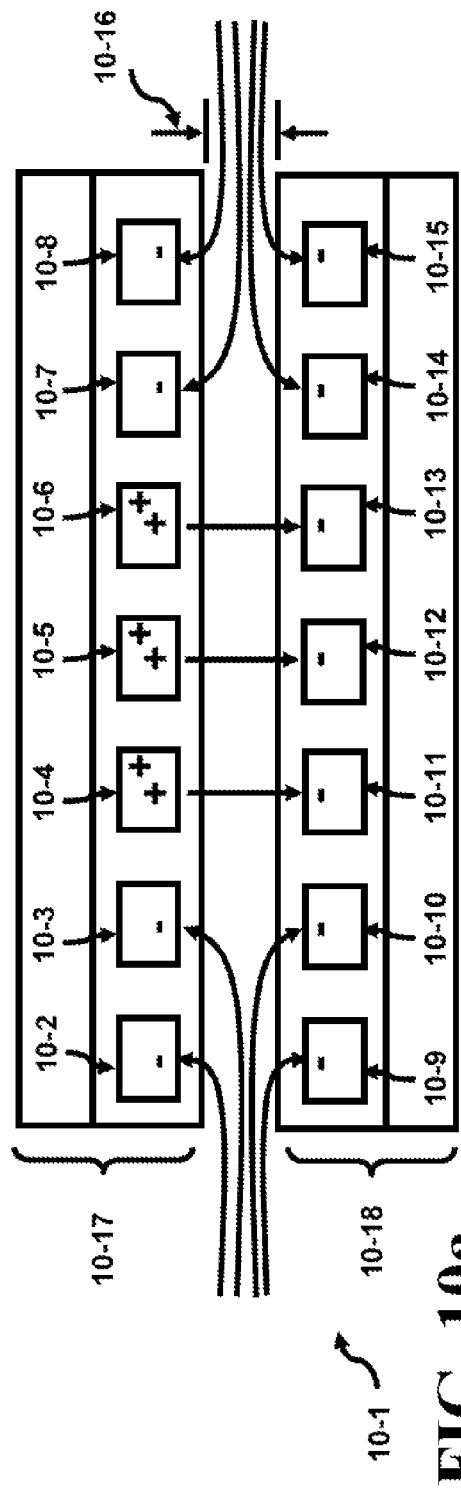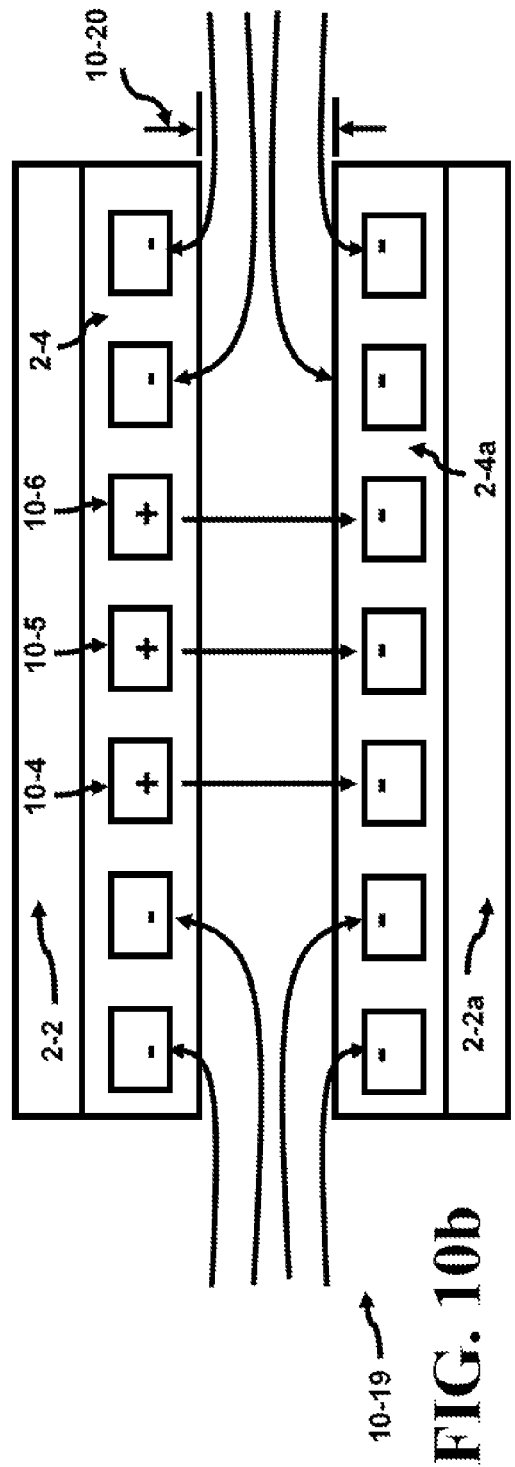

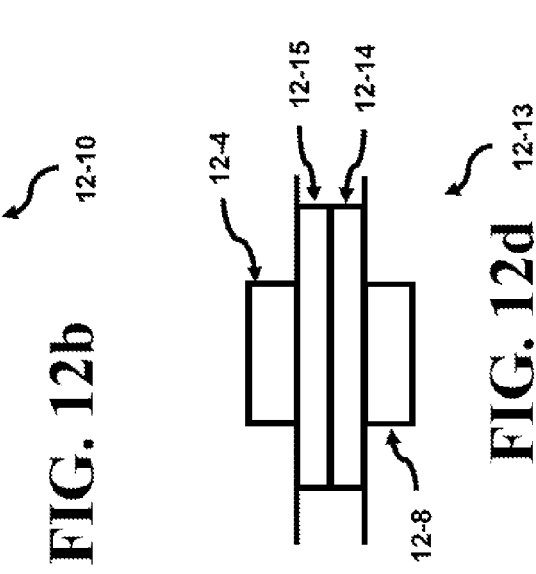
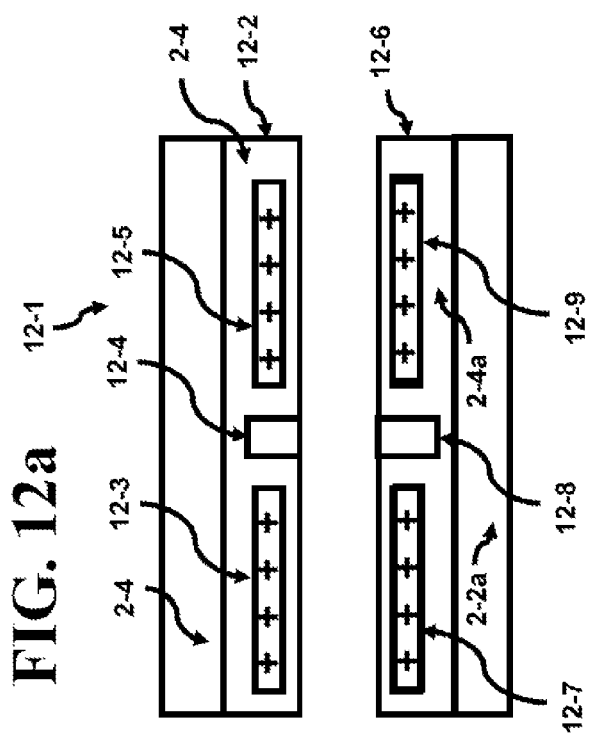
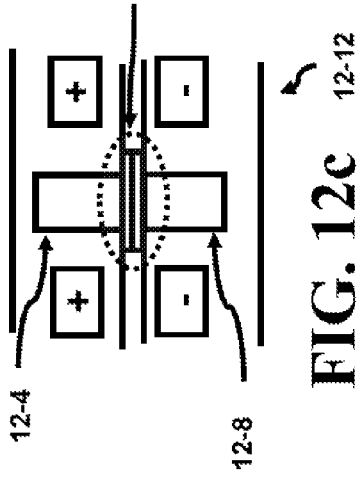
FIG. 12a  FIG. 12b  FIG. 12c  FIG. 12d

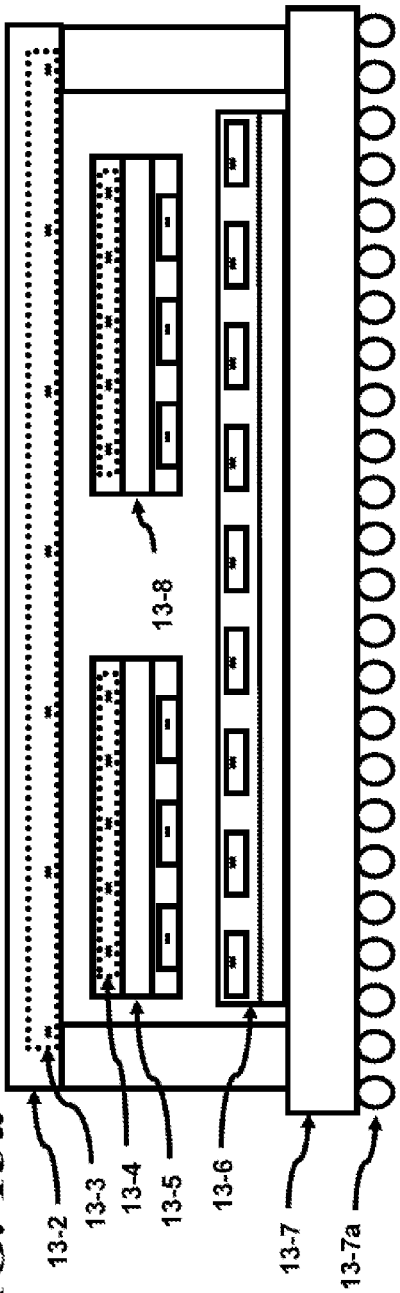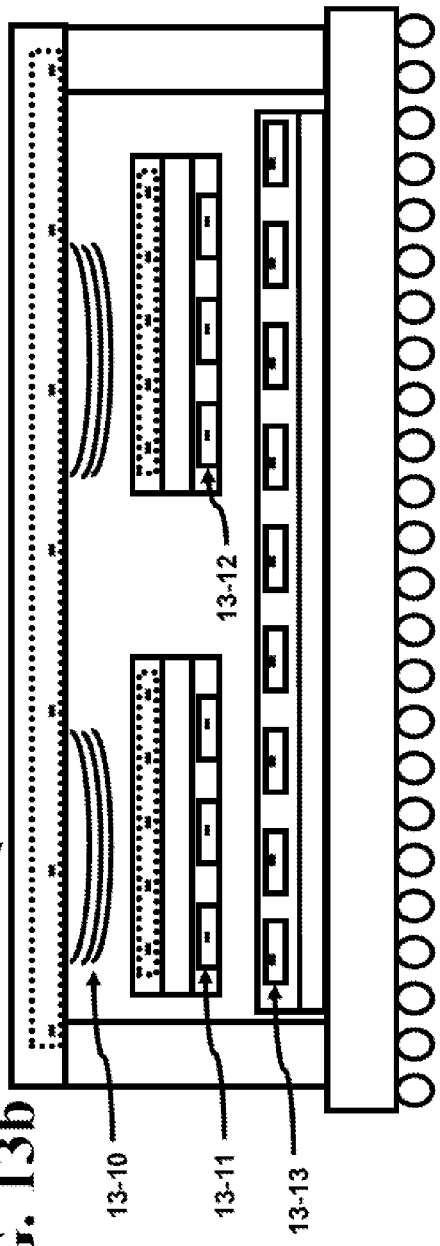

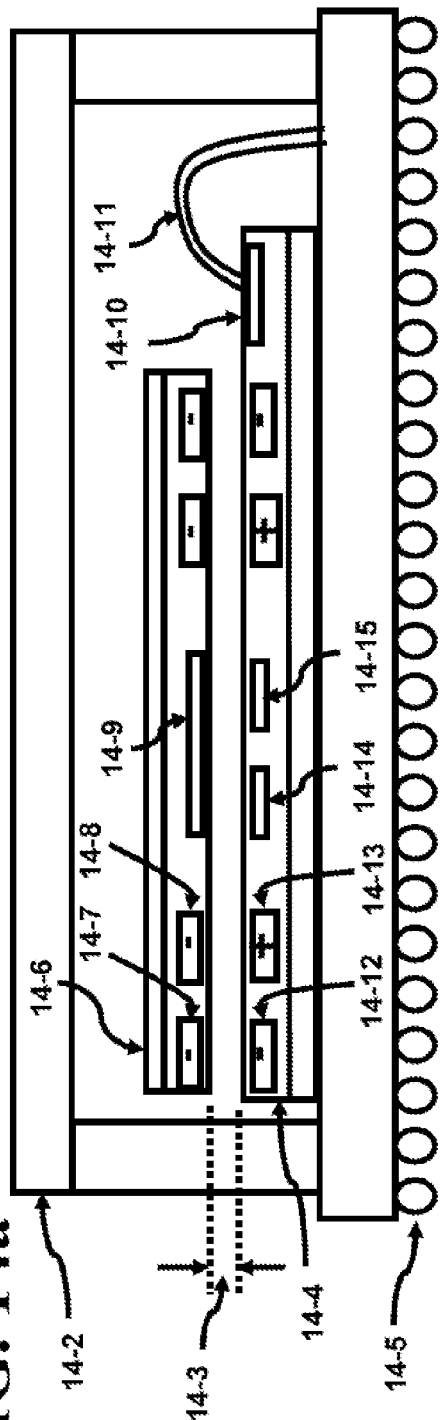
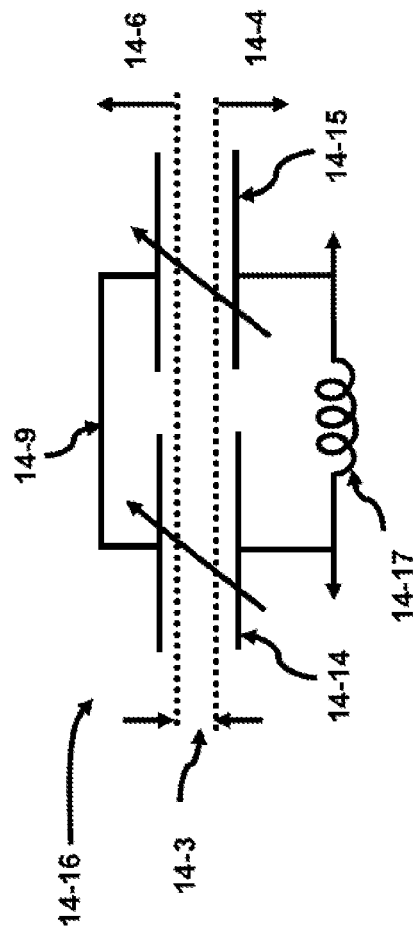
FIG. 14a
FIG. 14b

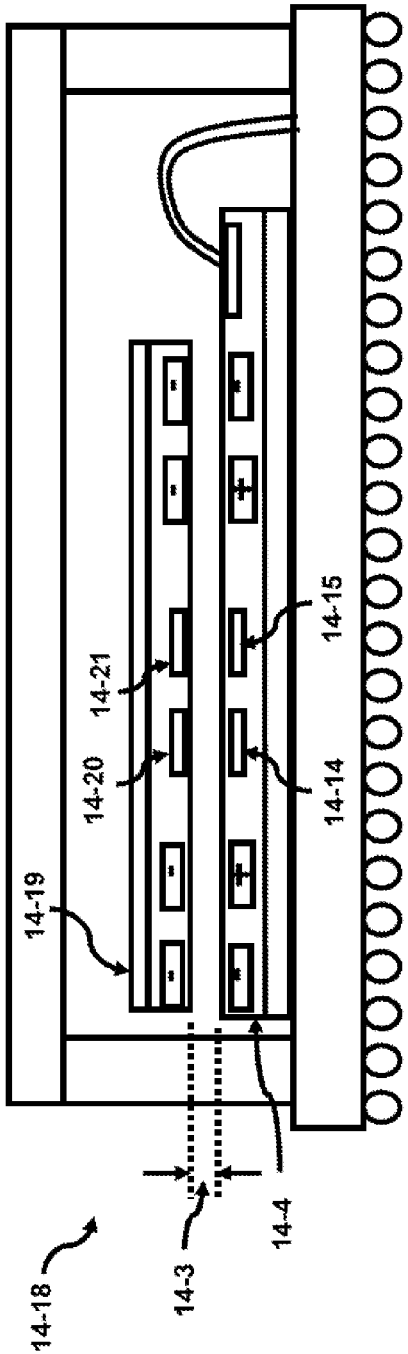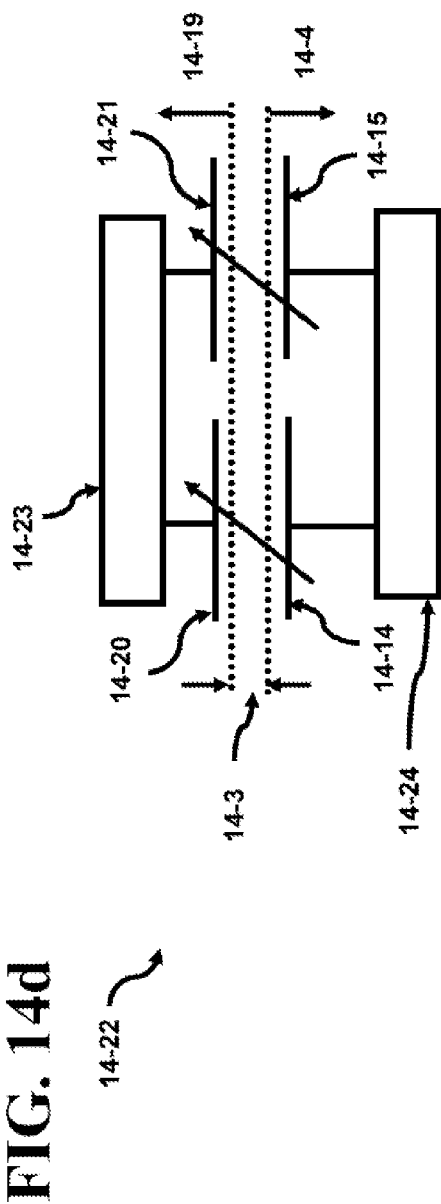
FIG. 14c
FIG. 14d

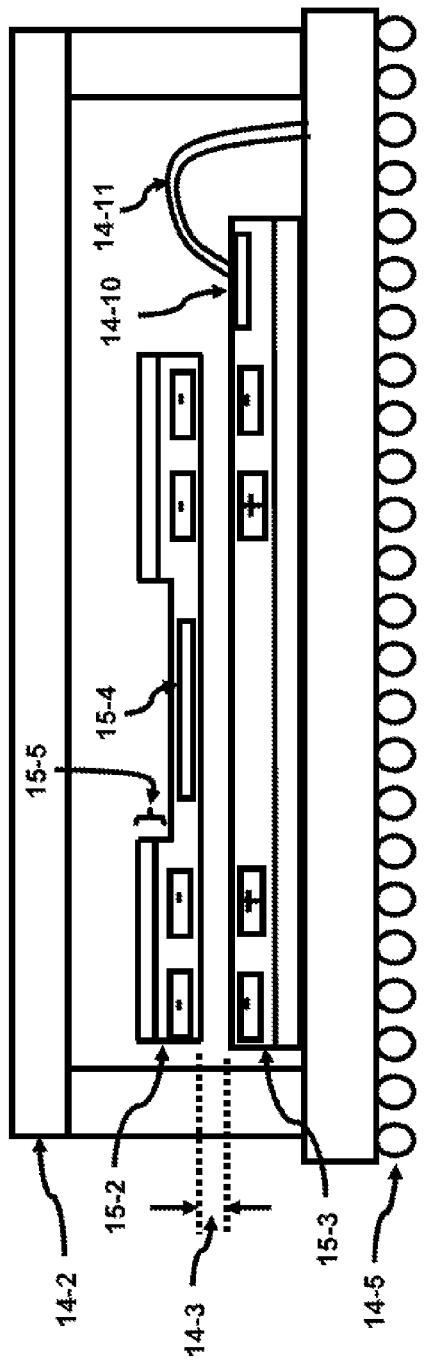
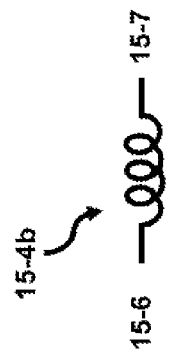
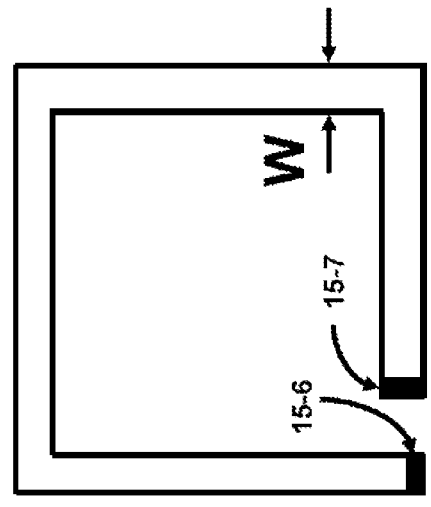

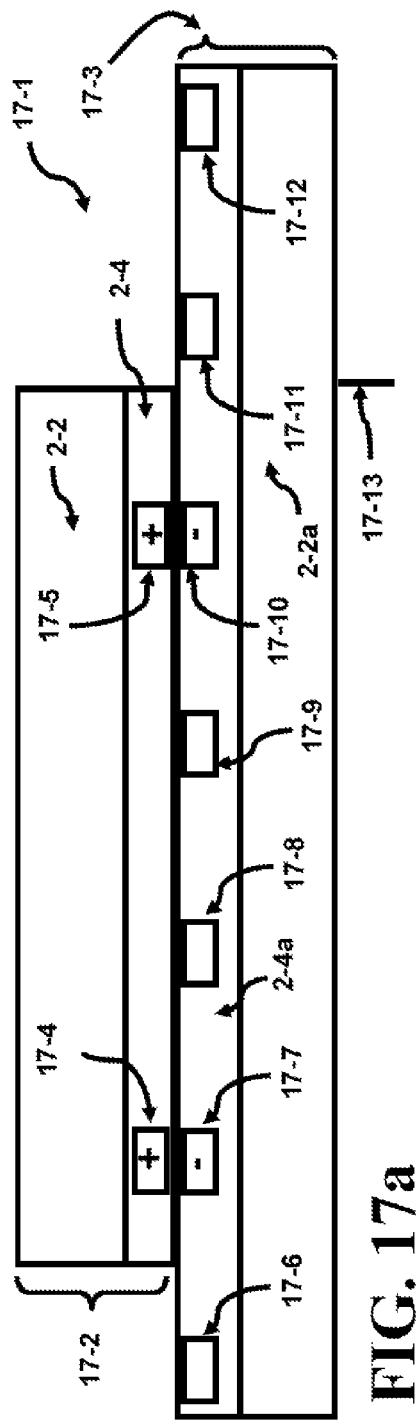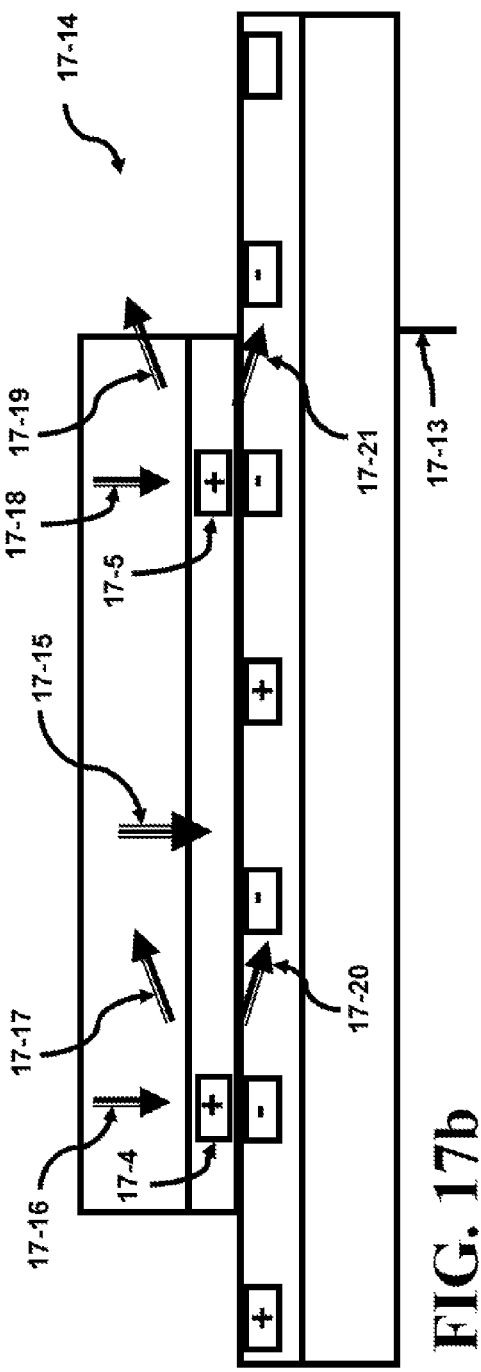
FIG. 17a
FIG. 17b

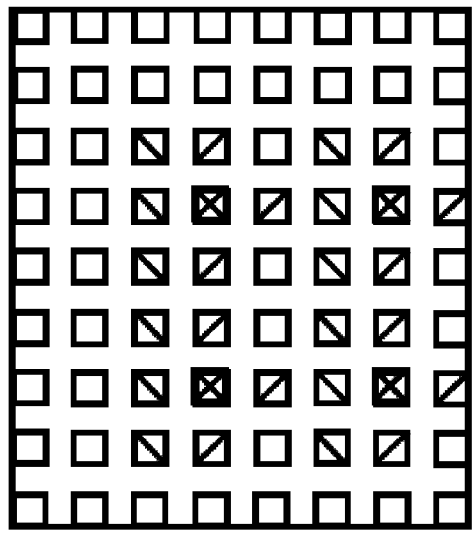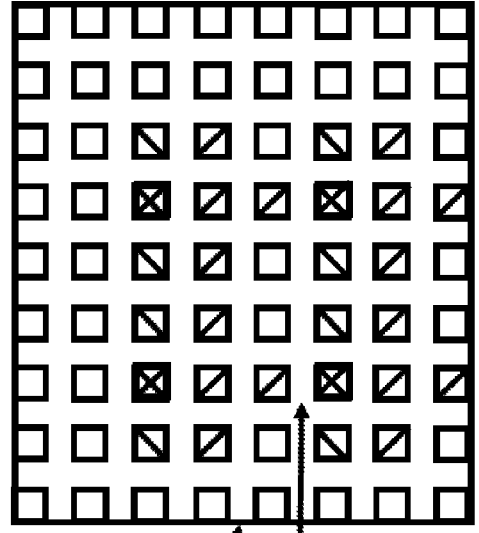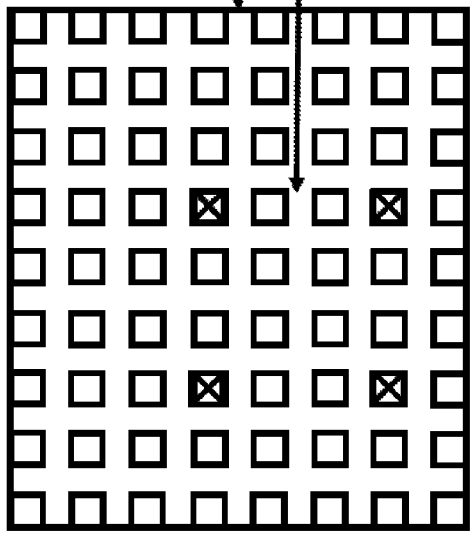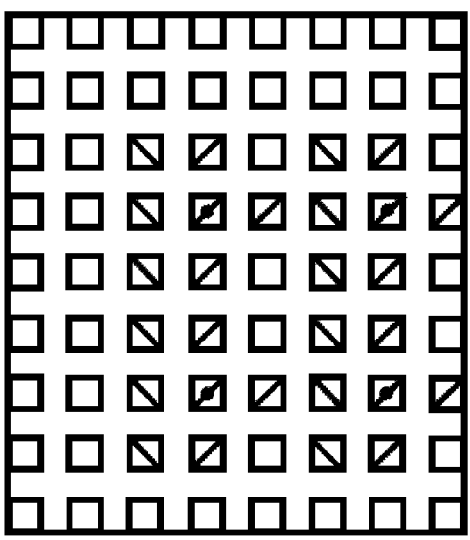
FIG. 21a
FIG. 21b
FIG. 21c
FIG. 21d

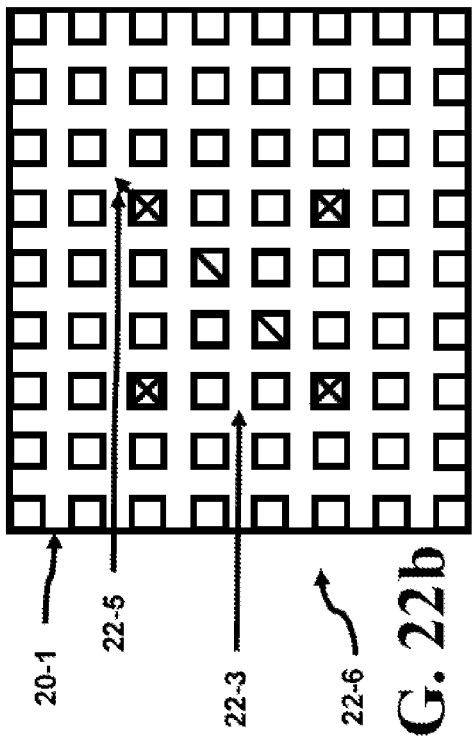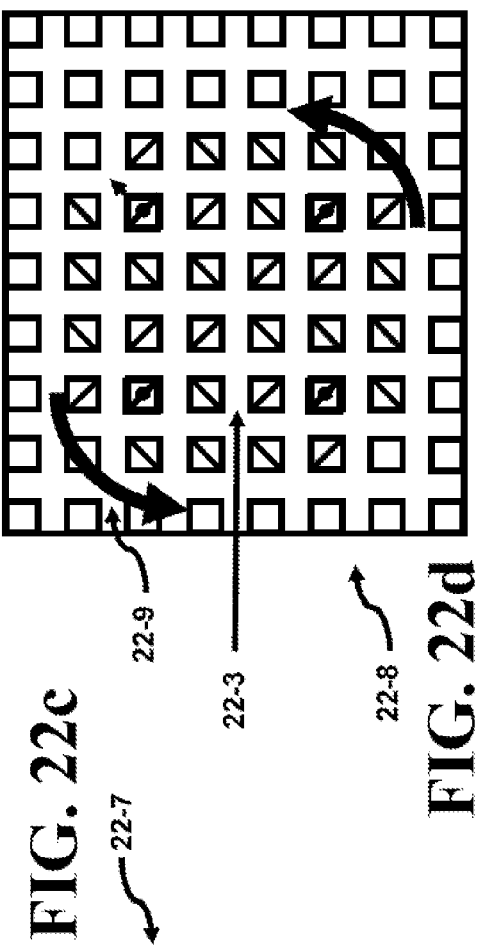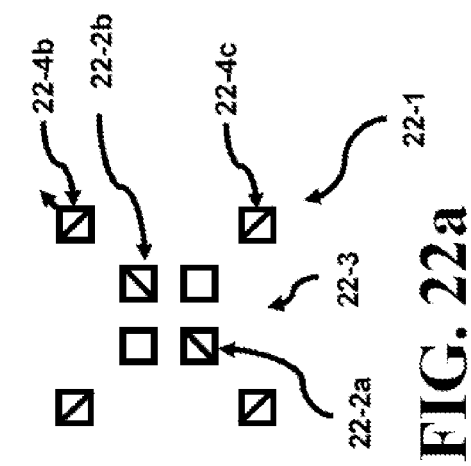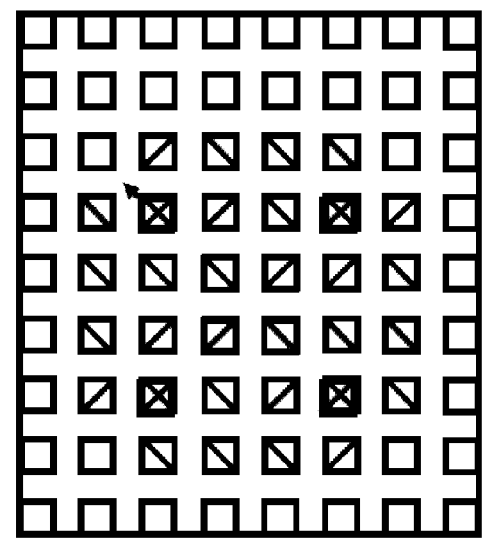
FIG. 22a
FIG. 22b
FIG. 22c
FIG. 22d

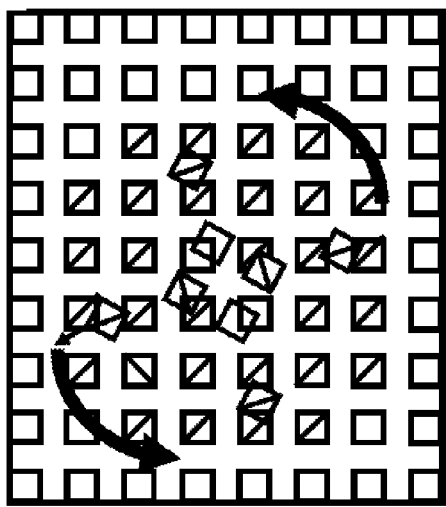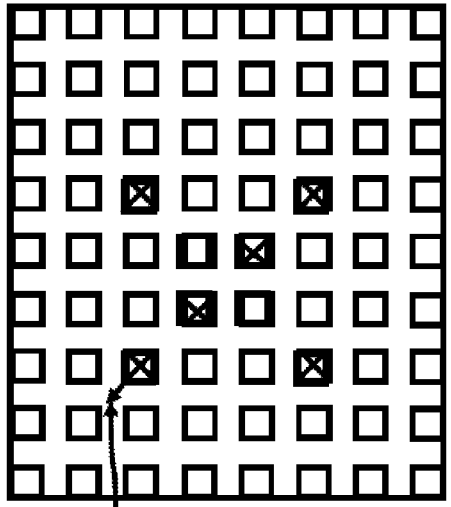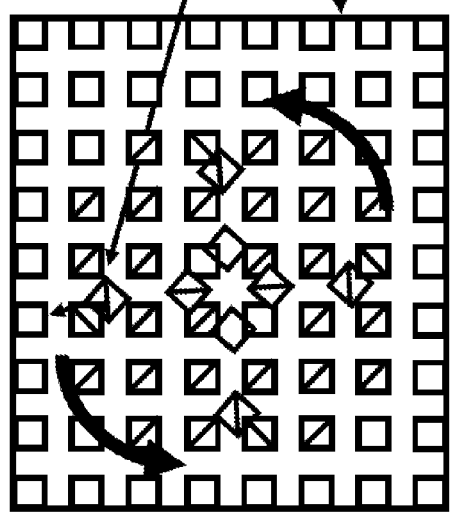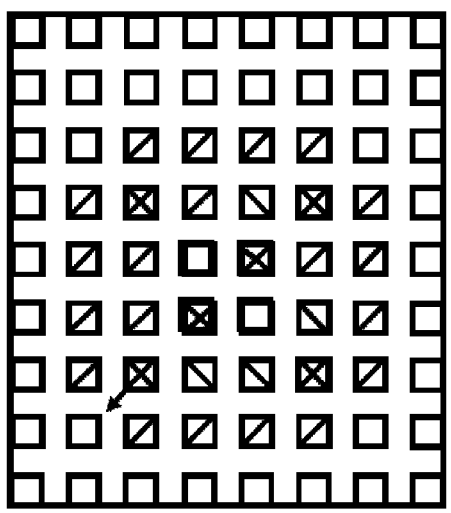

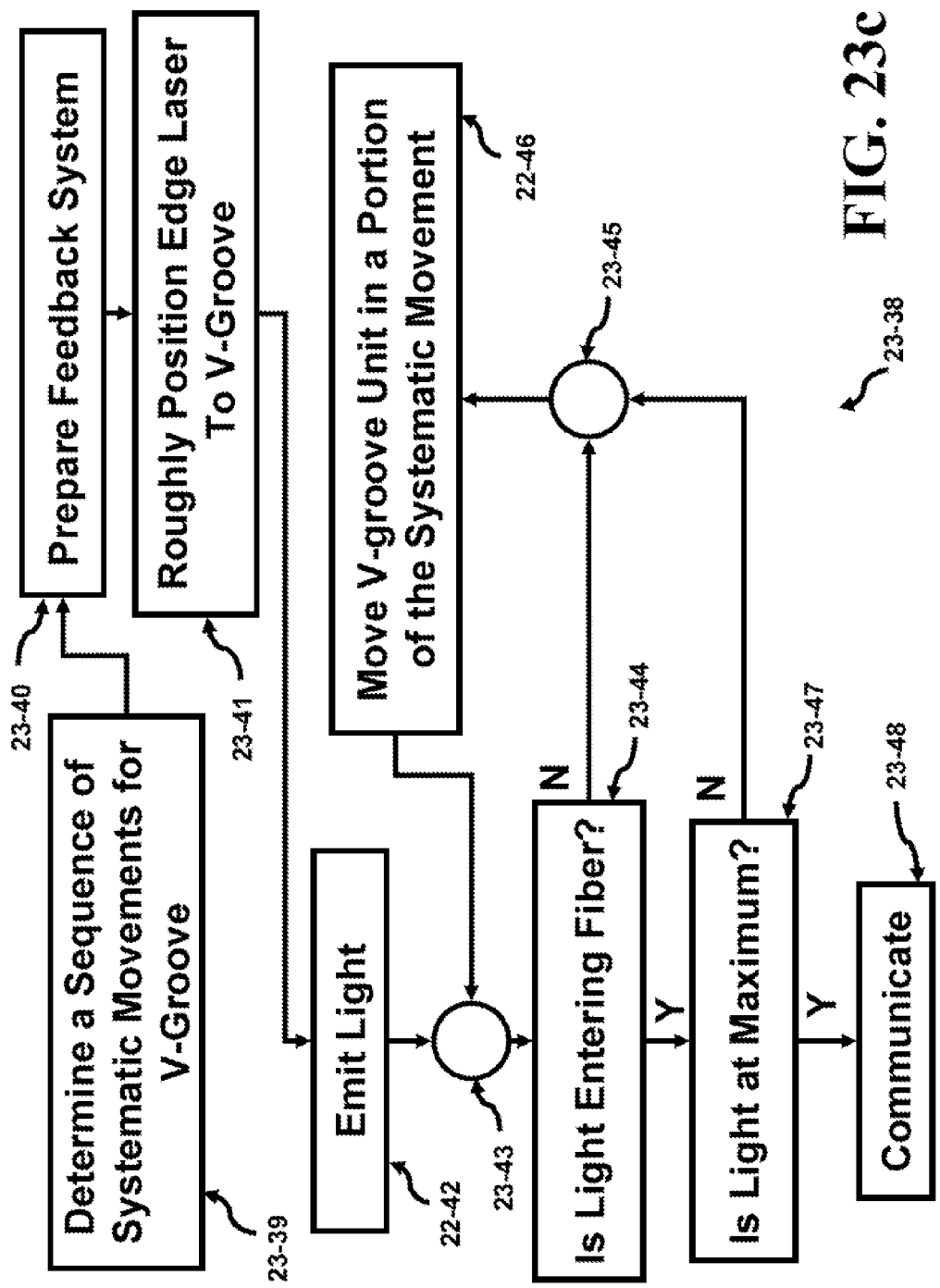

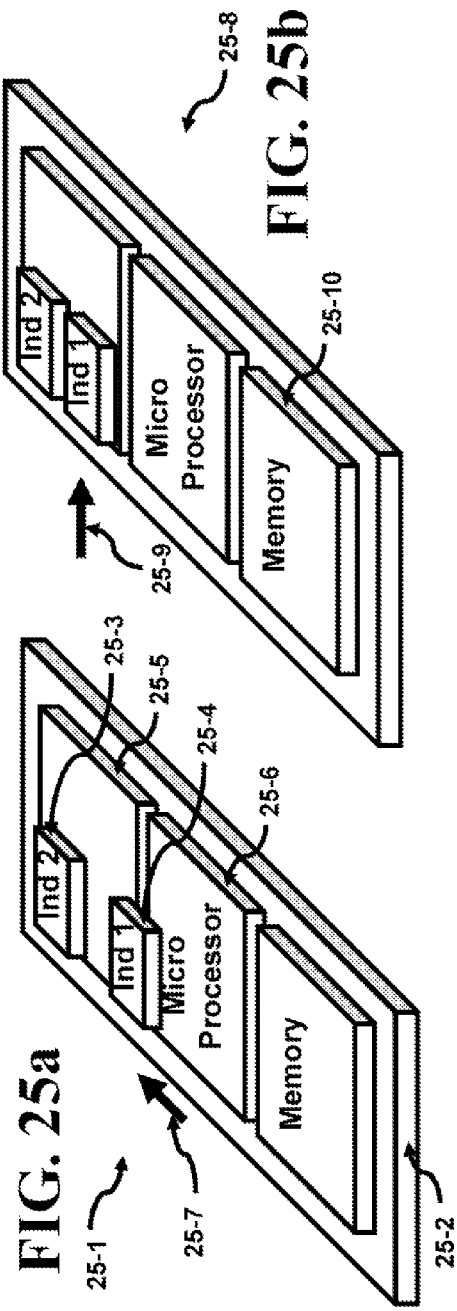
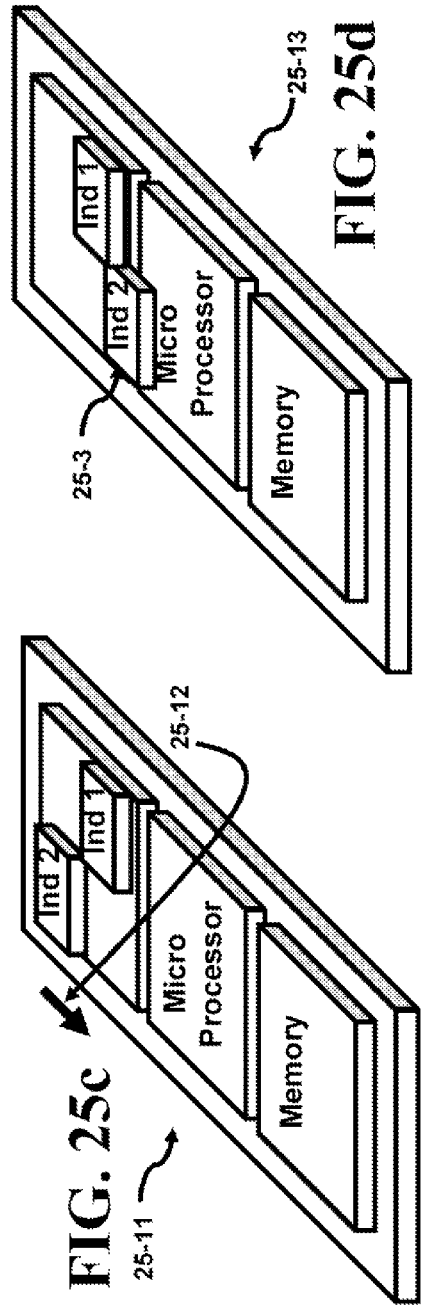

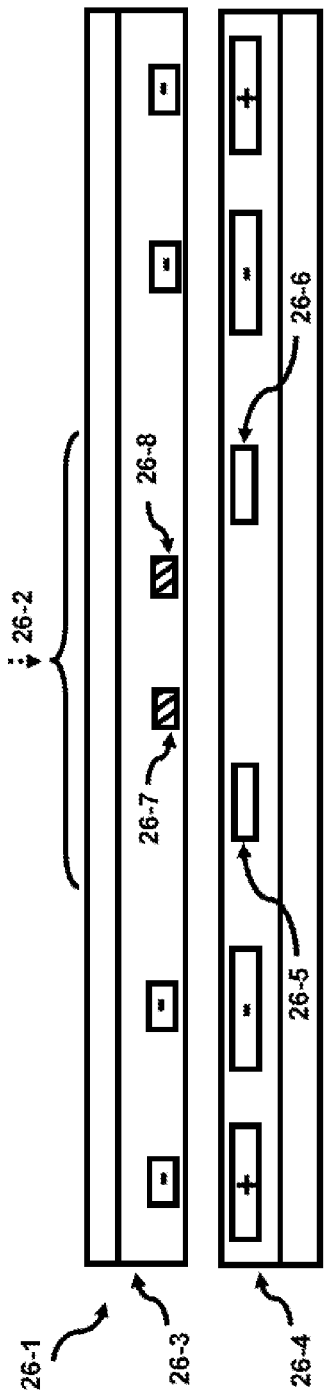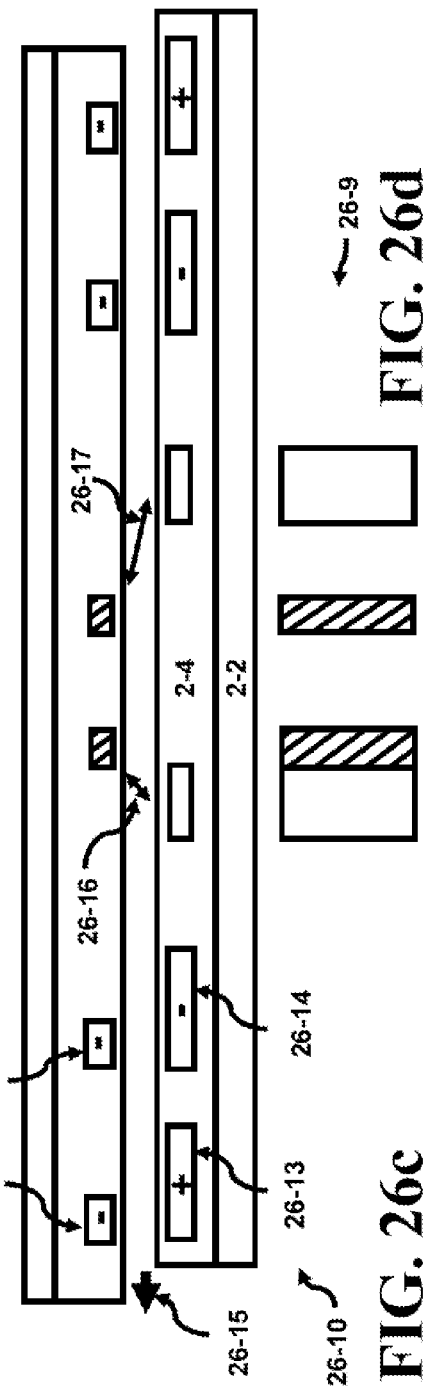

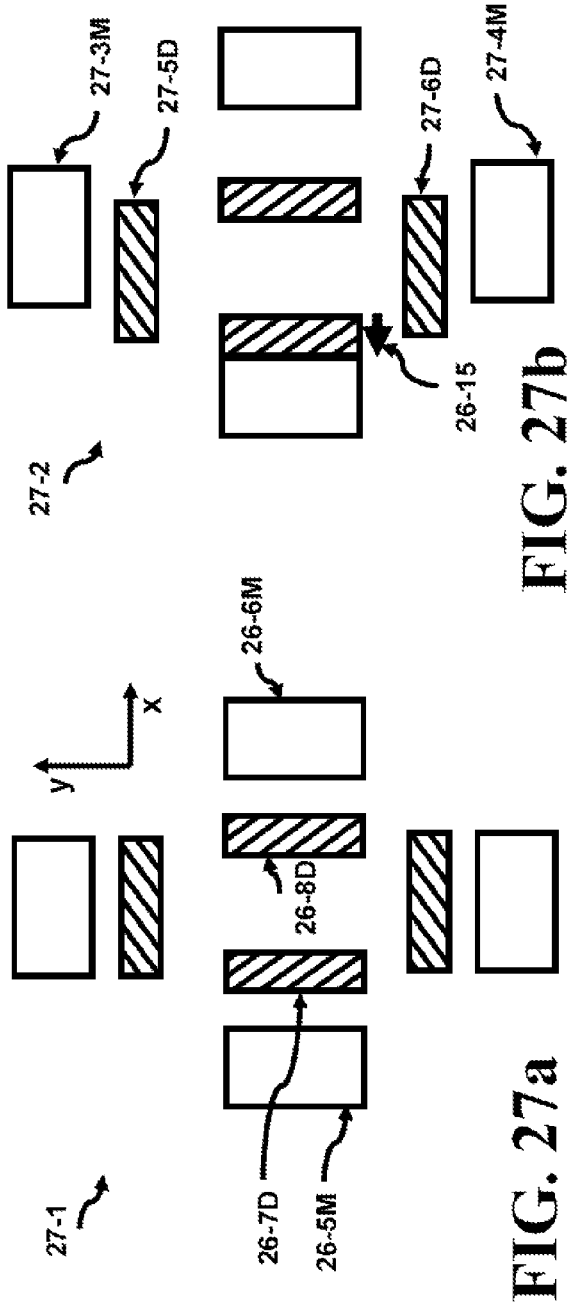

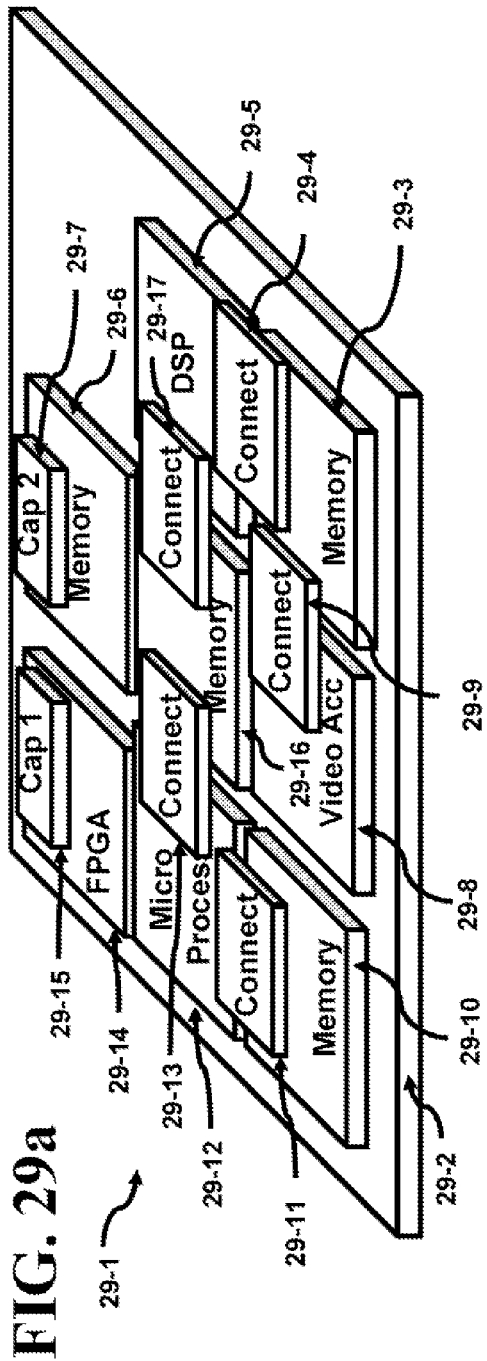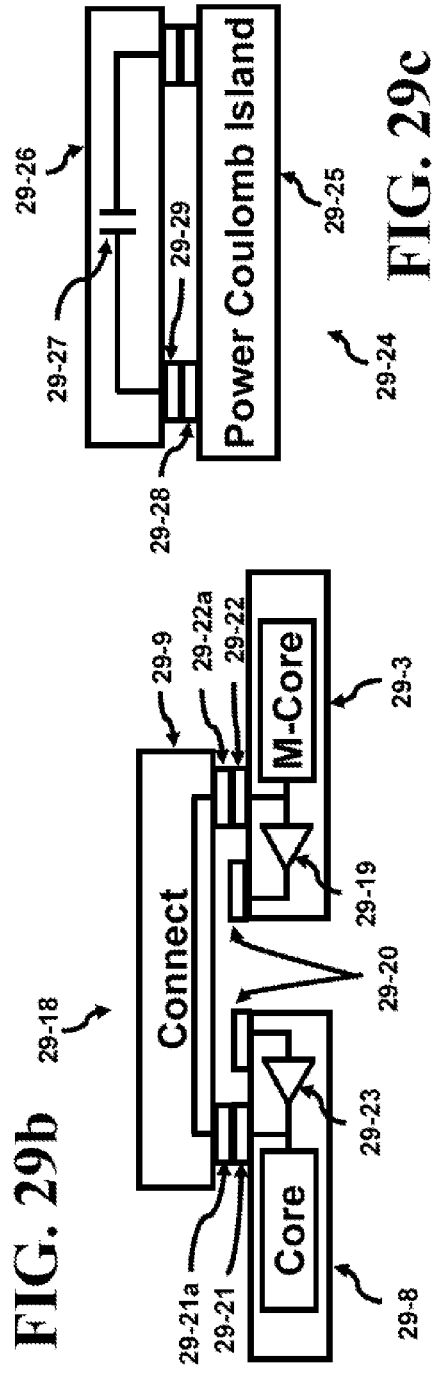
FIG. 29a
FIG. 29b
FIG. 29c

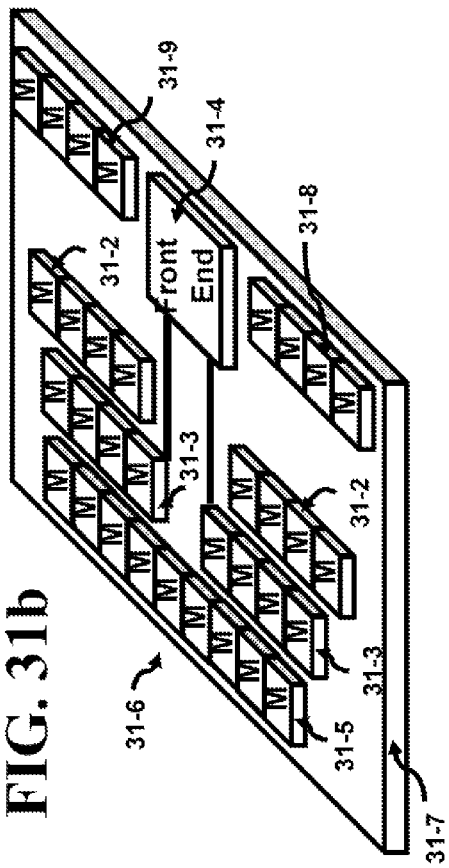
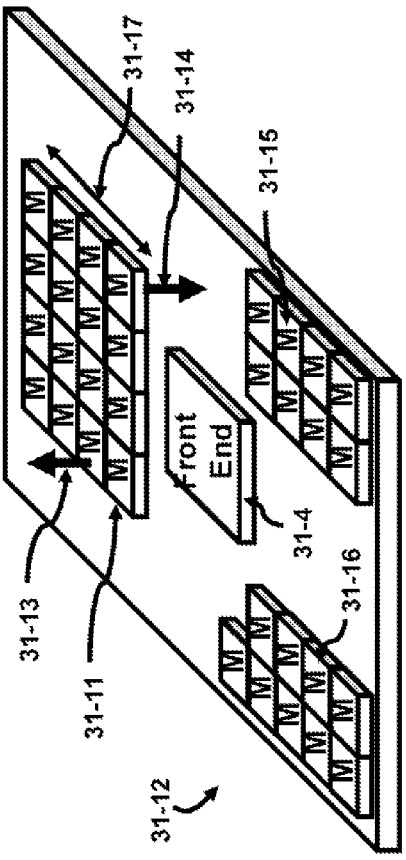
FIG. 31b
FIG. 31d
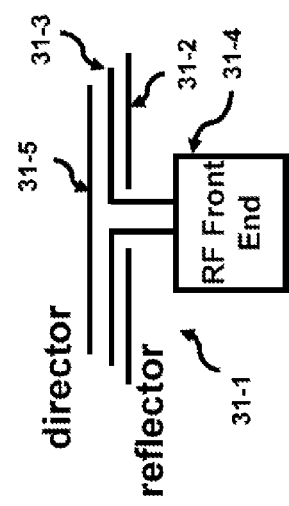
FIG. 31a
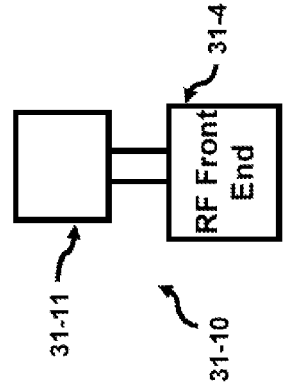
FIG. 31c

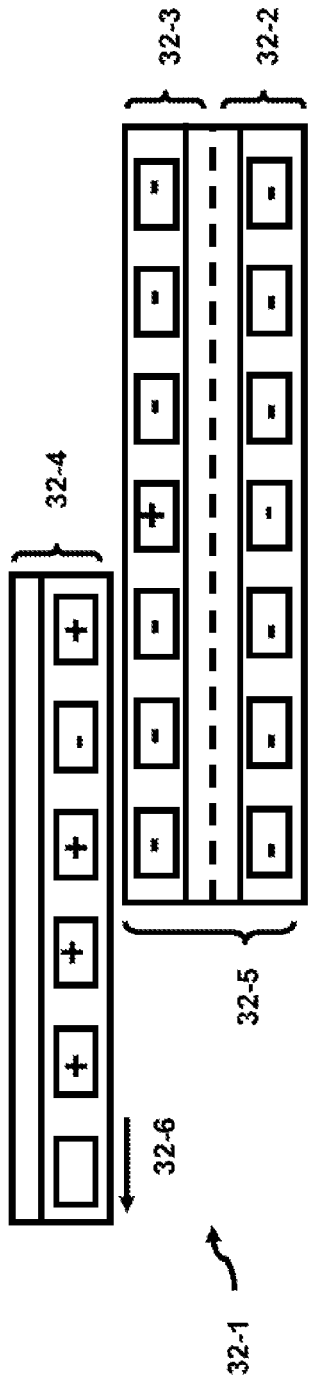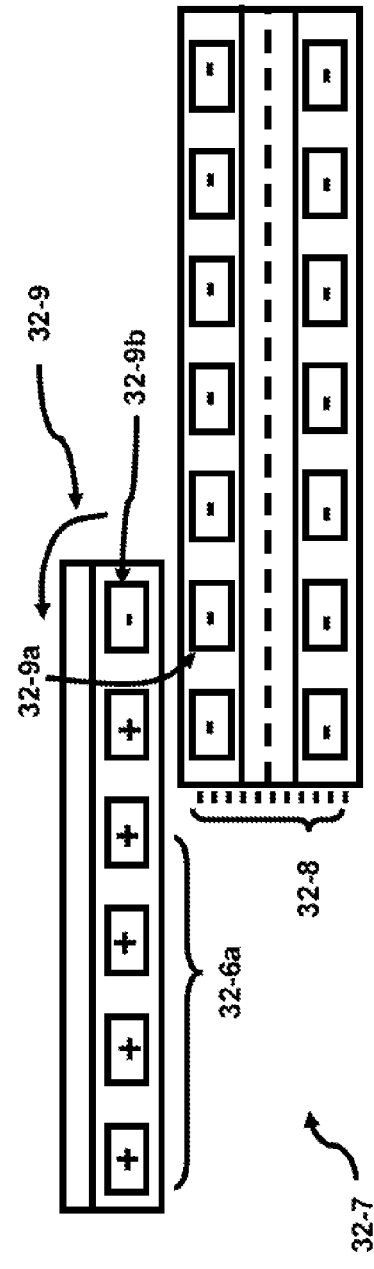
FIG. 32a
FIG. 32b

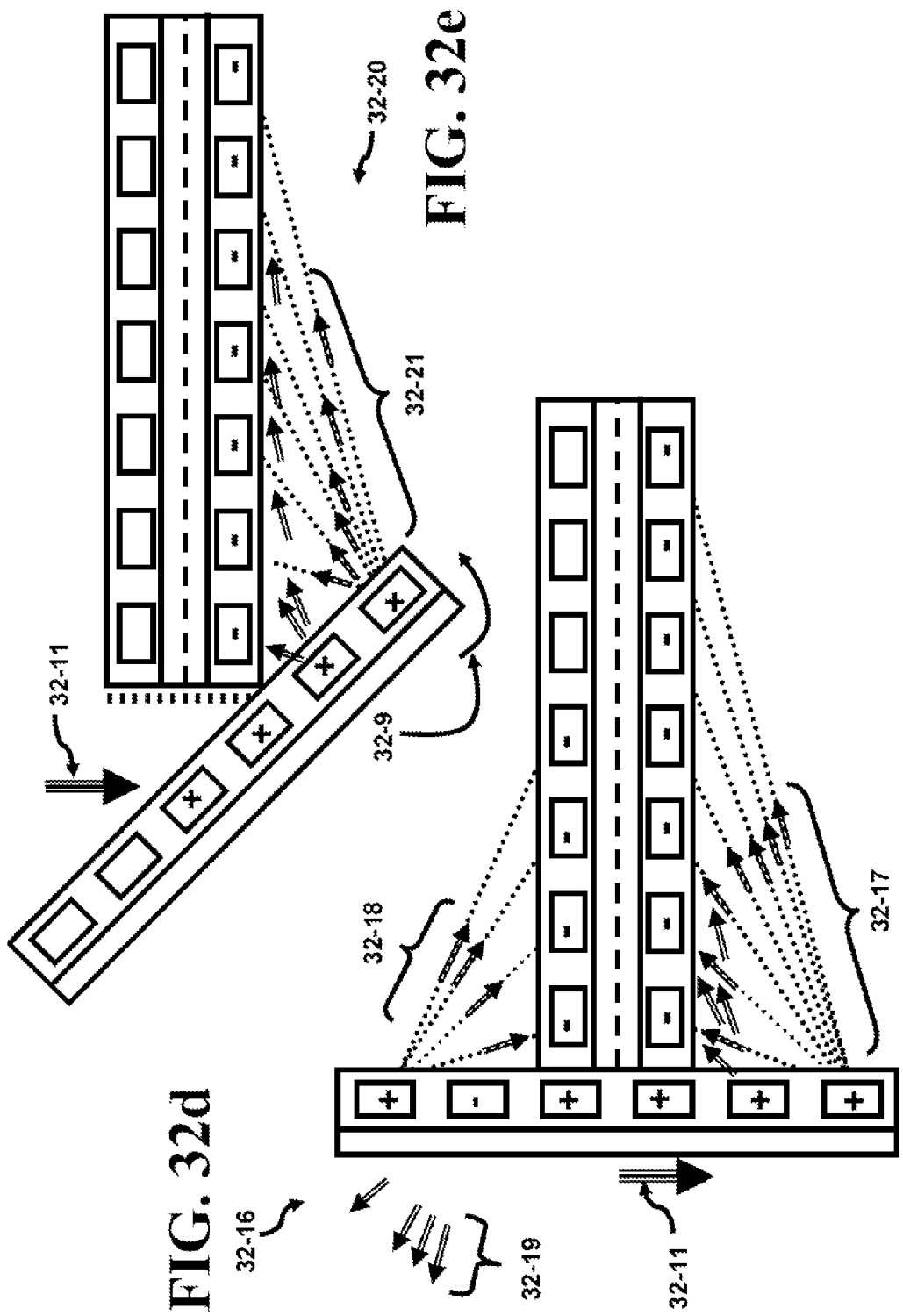

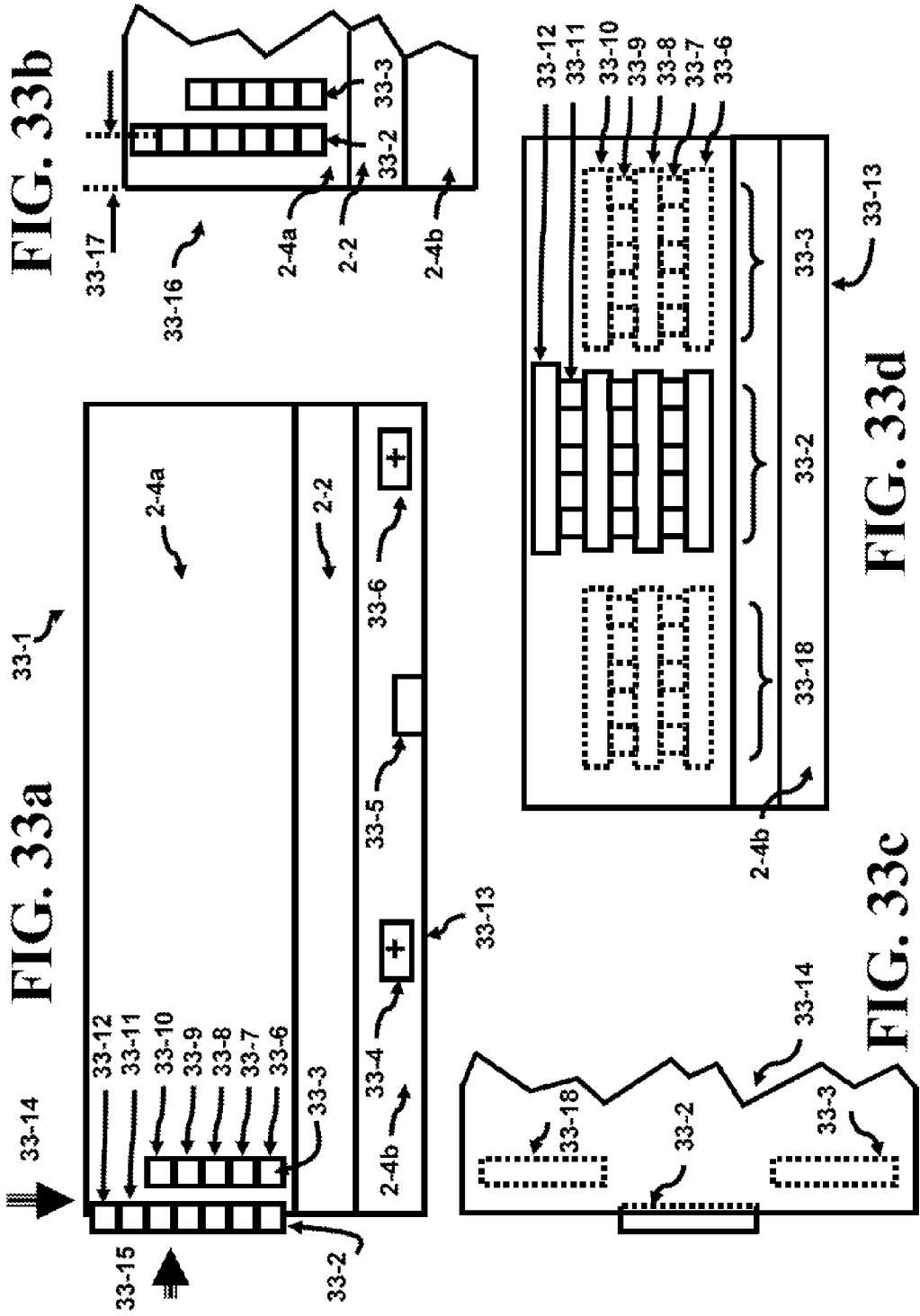

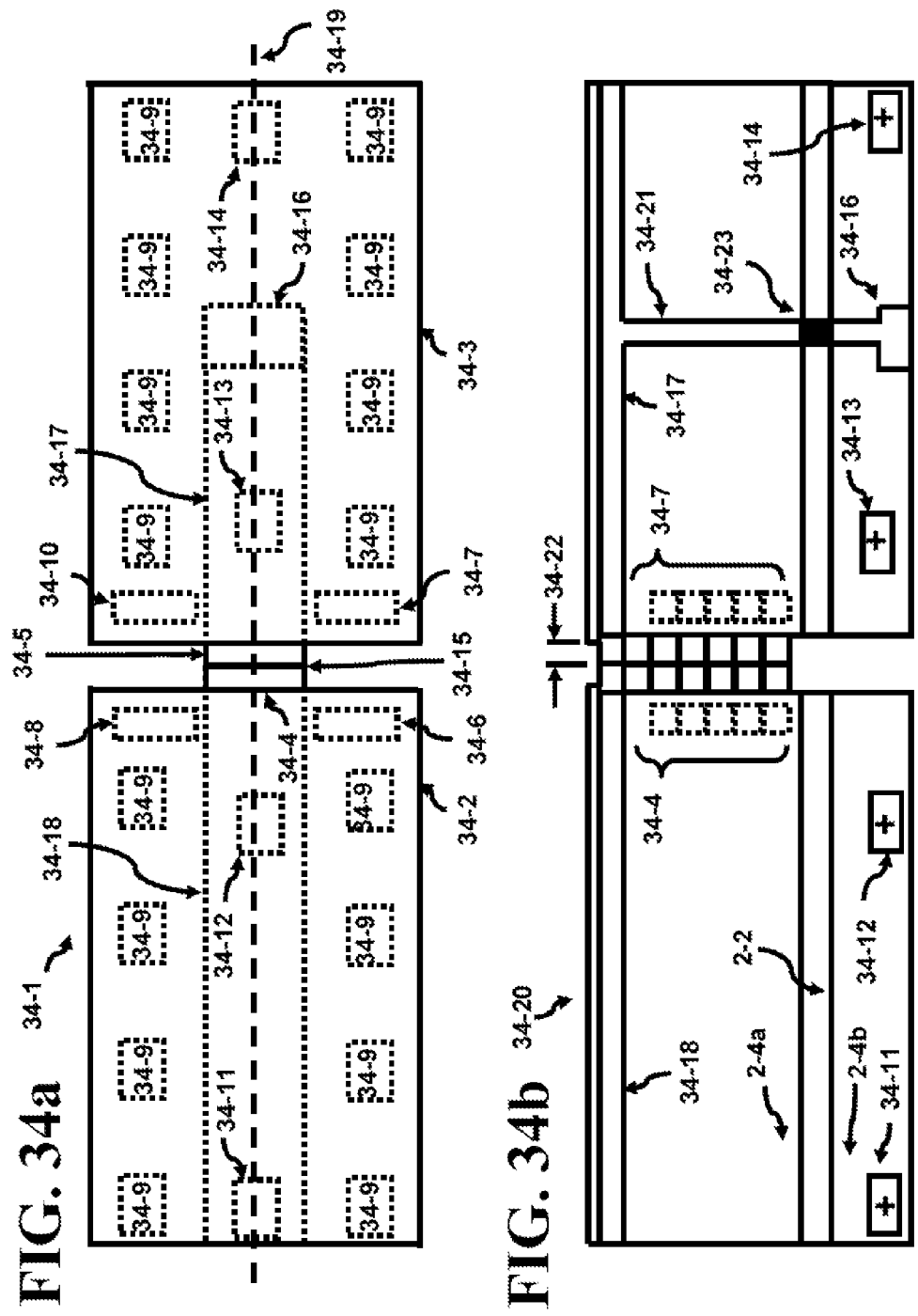

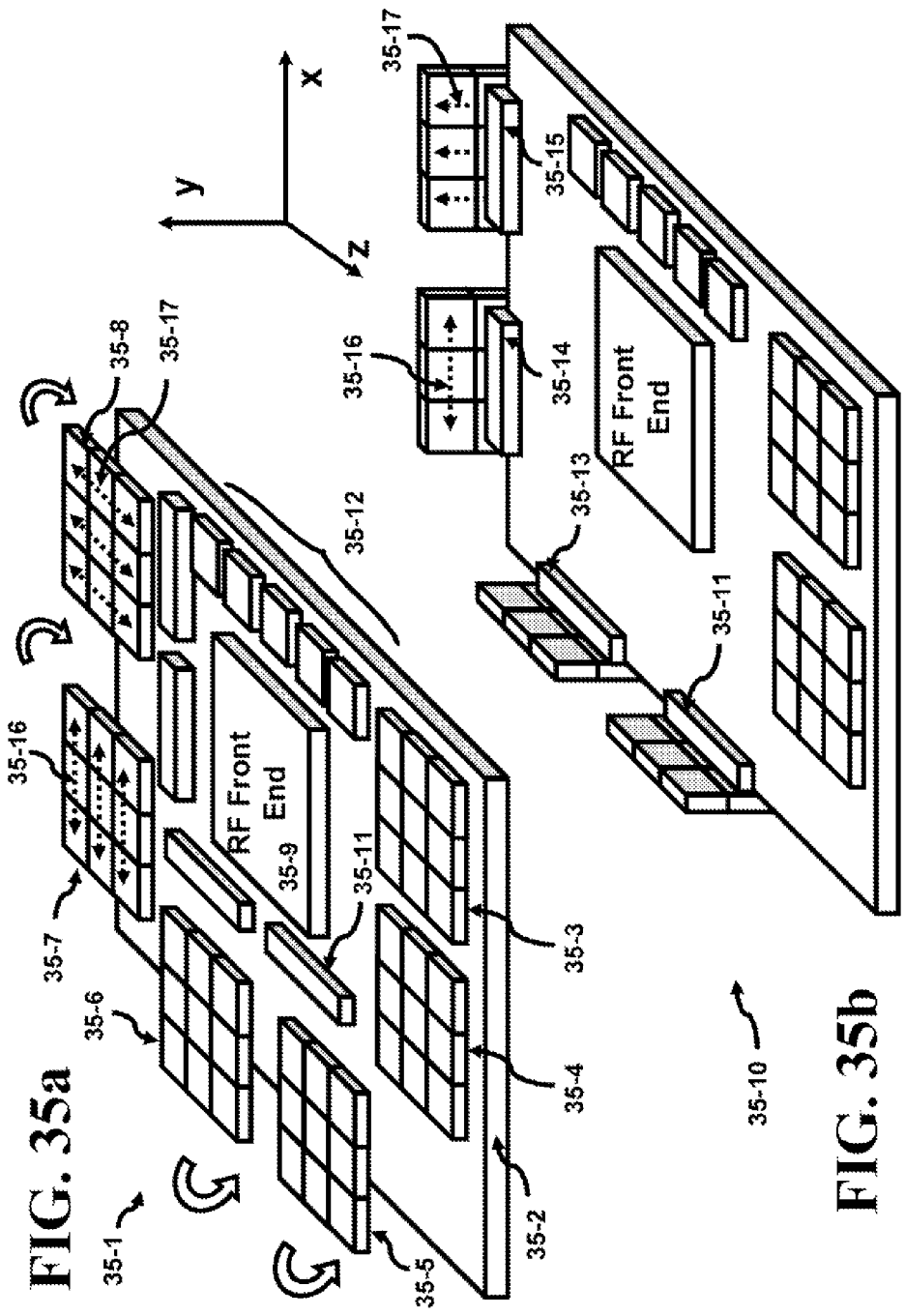

USING COULOMB FORCES TO STUDY CHARATERISTICS OF FLUIDS AND BIOLOGICAL SAMPLES

BACKGROUND OF THE INVENTION

ASIC (Application Specific Integrated Circuit) and custom logic typically are unforgiving systems since an error in the logic may not allow for an easy recovery once the device has been fabricated. The re-design cycle time can be 3-4 months. An FPGA (Field Programmable Gate Array), however, is an on the fly reconfigurable Boolean logic system. The heart of Reconfigurable logic is the configurable logic block which is formed using Boolean logic and can be altered very easily since an input digital signal can modify the operation of the logic block without physically altering it. The ability to program, use, reprogram, use and reprogram, use and continue this cycle infinitum are features very desirable which allow a system to adapt to different changing specifications or conditions quickly. The re-design cycle can be done in seconds. This helps explain why the reconfigurable logic business has grown into a several billion dollar enterprise.

Reconfigurable systems are very useful and allow for a rapid change to the system to achieve the desired behavior in a short time period. There are situations where some systems that would desire the ability to be reconfigurable but currently are not able to do so. These systems contain a component that is a discrete element: inductor, capacitor or antenna. It is difficult to replace these discrete elements with switches formed from active circuitry since the circuitry introduces loss and degrades the characteristics of the discrete elements. An RF (Radio Frequency) switch is used to switch the antenna from the transmitter to the receiver and the switch itself unfortunately introduces a loss of about 0.5 db. This is because it is difficult to replace metal with active components. In order to switch in a different value of an inductor, a first switch must disconnect the first inductor and a second switch must connect the new inductor. However, the switch introduces a loss and reduces the Q of the inductor; this is typically an undesirable effect. Finally, variable capacitors are currently formed by active devices; diodes or MOS gates, etc. These capacitors can behave nonlinearly and have a limited range of linear operation over a given voltage range.

In addition, wireless systems are comprised of hardware such as transmitters, receivers, DSPs (Digital Signal Processor), memory, D/A (Digital to Analog), A/D, filters and antennas. Typically, the wireless communication channel in a system may operate in a new frequency band. However, the system would perform better if the passive components could be changed to operate at that new frequency band. Since the hardware is physically soldered and bound in place in the system, it is very difficult to replace them with hardware that has been optimized to operate at this newer frequency band. One approach to this problem is to design the hardware so it operates over a larger frequency band. The consequences are a loss in gain and not being able to achieve the ultimate performance with an optimum design.

It would be very desirable to have a system that can be physically reconfigured to adapt to a changing conditions. For example, it would be desirable to have an inductor, antenna, capacitor or other hardware components to be physically alterable after they have been placed in the system. This specification addresses these concerns as described in the following section.

BRIEF SUMMARY OF THE INVENTION

One embodiment is dropping droplets of fluids onto substrates, forming various contact angles, overhanging the droplets over the edge of the substrate and moving two substrates until at least one droplet from each substrate make contact. Then, friction can be applied to the common surface to understand the properties of the surface tension. In addition, potentials can be applied across the membrane to study the diffusion properties and the concentration levels can be adjusted within the droplet to determine its effect. Another embodiment is forming a LOC (Lab on a Chip) where biological fluids and samples can be pumped, mixed, analyzed and confined into cavities. One embodiment of using Coulomb forces is to adjust and align laser from/into optical fibers. Another embodiment allows a pattern of non-overlapping metallic sheets to determine the acceleration of the system. As the acceleration causes the distances between the metallic sheets to vary, the amount of acceleration can be determined. An orthogonal placed pattern of sheets can be used to determine the direction of the acceleration. Such a device can be used to enable air bags during a car crash.

Another embodiment is described which uses Coulomb forces to adjust the physical dimensions of antennas. Thus, antennas can be adjusted in the field to better match the carrier frequency. Several antennas: the Yagi, the patch, the bow-tie, the meanderline, and the dipole antenna can be adjusted to benefit from this adjustment. As more antennas can be placed on a substrate, additional flexibility occurs such as using an antenna at a given carrier frequency to transmit a signal while the second antenna can be used to receive the signal at a different carrier frequency. Conversely, the antennas can be used in a MIMO system to provide a multi-channel wireless communication where the antennas can be moved on the surface of a substrate to improve reception. One embodiment is the ability to rotate an antenna substrate 90° around the edge of a substrate. This allows antennas to be formed that exist in three orthogonal planes. Receiving and transmitting signals in three orthogonal dimensions improves reception if one of the signals fades in a given dimension. Many of these techniques are also applicable to inductor construction.

Another embodiment is described that can assemble substrates over one another to form a stacked substrate. The various layers of the stacked substrate can be separated from each other by using Coulomb forces. One embodiment shows how a beam substrate can be used to increase the separation. The instructions for assembly and a FSM (Finite State Machine) can be included in the stacked substrate to pave the way for a self-constructing 3-D automaton. The beam substrate can be used to carry heat, fluids, electrical power or signals between the various layers of the stacked cells besides providing a mechanical support. The embodiment of a stacked substrate can be assembled into a cylindrical coil, a transformer or a coupled transformer depending on the construction of the beam structure. In one embodiment, the magnetic coupling of the transformer can be altered by changing the distance between the separated substrates.

In another embodiment, metallic plates can be positioned over one another to form capacitor which can be used to detect motion, distance, velocity, position and identity of the substrates. These capacitors can be used to form an LC tank circuit where the distance between the plates of the capacitor can be altered to alter so that the capacitance is altered and the frequency is changed. The capacitor can be used to communicate digital information between the substrates.

In another embodiment, a combination of attractive and repulsive Coulomb forces can be used to form a levitation system using at least two substrates. Another is to have two outer substrates that make a channel region and confine a third substrate within the channel region. The system can be levitated just by using only like charges. In order to introduce further control, some of the islands can be altered in the strength and polarity of their charge to move the third substrate vertically within the channel region.

Another embodiment is increasing the number of Coulomb islands to decrease the required voltage that needs to be applied to the island. This helps in reducing the stress applied to the junctions and devices.

In another embodiment, the substrate can be processed to exposed metallic posts or electrical contacts that can provide a DC connection to provide power and DC signals. In addition the edge can be etched to expose the metal layers in a substrate to allow an electrical connection to occur.

In one embodiment of the invention is a system where the substrates can be reconfigured by the application of adjustable Coulomb forces between juxtaposed surfaces of substrates to create new systems. These forces can be used to detach, raise, move, rotate, drop and reattach substrates into new system configurations. An embodiment of placing a pattern of islands on each juxtaposed substrate and determining the sequence and charging to lift, move and dropping a substrate. The determination is done by a control unit that can be confined to one of the substrates, distributed among several substrates, calculated on the fly, stored in memory, or calculated externally. Feedback from the sensors can be used to control and stabilize the movement of the substrate. The master control can be in the mother substrate.

In another embodiment, a Faraday shield can be placed under the Coulomb island to isolate the Coulomb island from the remainder of the substrate. In addition, the potential of the Faraday shield can be altered to control the electric field leaving the substrate and thereby controlling the force being applied to a juxtaposed Coulomb island. Another embodiment is performing edge processing of a substrate. Vertical Coulomb islands and vertical Faraday shields can be formed. This inventive aspect allows Coulomb islands to be charged to attract two or more substrates along their edge.

In another embodiment, charge is induced in a metallic Coulomb island by an externally charged plate. The Coulomb island can have a probe opening to directly charge the island, and then this charged Coulomb island can be used to induce a charge on another Coulomb island. The probe opening can be mechanically probed using an external probe or a MEMS probe. In another embodiment, the gate of a non-volatile memory that is isolated is connected to a Coulomb island where the entire combined structure is surrounded by an insulator. The island is placed at the surface of the substrate to maximize the forces that can be generated between this island and another island located near the surface of a second substrate. Furthermore, several non-volatile devices can be connected to the island simultaneously where each device can be optimized to perform a special function.

In another embodiment, Coulomb forces are used to detach substrates from the system to decrease leakage current in that substrate to decrease power dissipation. An embodiment allows an inductor on a substrate to be levitated so that losses of the inductor are decreased. Another embodiment is wire bonding a substrate to power and DC supplies and using the Coulomb force to lift the substrate so that the substrate is levitated. Another embodiment is using the Coulomb forces between two substrates to cause one of the substrates to overhang a new substrate which does not have Coulomb islands. However, the substrate over hanging the new substrate can electrically connect to the new substrate to introduce a new circuit element into the new substrate.

BRIEF DESCRIPTION OF THE DRAWINGS

Please note that the drawings shown in this specification may not be drawn to scale and the relative dimensions of various elements in the diagrams are depicted schematically and not to scale.

FIGS. 1a-1h depict a reconfigurable system in accordance with the present invention.

FIG. 1i) illustrates a side cross-sectional view of the reconfigurable system with the daughter substrates connected and j) levitated to the mother substrate in accordance with the present invention.

FIG. 1k shows a flowchart to reconfigurable the system in accordance with the present invention (Note that the decision unit has a block shape instead of a diamond one).

FIGS. 2a depict the diagram used to calculate the force of a charged disk in accordance with the present invention.

FIG. 2b illustrates two charged islands juxtaposed to each other in accordance with the present invention.

FIG. 2c) reveals plot of gravitational force of substrates and the voltage necessary to apply to an island pair, d) a plot of the voltage applied to the islands to maintain a constant force as a function of the number of islands, and d(1)) the forces between a sphere and a plane in accordance with the present invention.

FIG. 2e) presents a portion of a limit component from a reconfigurable system with a surface charge and f-g) depict a portion of a unit component from a reconfigurable system with an electric field in accordance with the present invention.

FIG. 3a illustrates a chargeable plate in a reconfigurable system in accordance with the present invention.

FIG. 3b reveals forming an induced charge on a chargeable plate in a reconfigurable system in accordance with the present invention.

FIG. 3c shows the cross sectional view of a probe (could be external or on-substrate) routing excess negative charge to a power supply in a reconfigurable system in accordance with the present invention.

FIG. 3d presents the probe being disconnected in a reconfigurable system in accordance with the present invention.

FIG. 3e depicts the cross sectional view of the electric field from the chargeable plate in a reconfigurable system in accordance with the present invention.

FIG. 3f illustrates the top view of the chargeable plate in a reconfigurable system in accordance with the present invention.

FIGS. 4a and 4c reveal the cross sectional view of the electric field of the chargeable plate after placing a second chargeable plate (forming a Faraday Shield) beneath the initial chargeable plate in a reconfigurable system in accordance with the present invention.

FIGS. 4b and 4d show the top view of the chargeable plate in a reconfigurable system in accordance with the present invention.

FIG. 8a) depicts two substrates preparing to be bonded together where one substrate has been given a charge and b) illustrates the charged bonded substrate of FIG. 8a.

FIG. 9a) reveals a positive charged substrate held by an attractive Coulomb force to the negative charged substrate and b) shows the repulsive Coulomb force between two similarly charged substrates in accordance with the present invention.

FIG. 10a) presents repulsive/attractive charged substrates that are held apart by a repelling Coulomb Force and b) depicts the repulsive/attractive charged substrates (one with less positive charge) causing more separation due to a less attracting Coulomb force in accordance with the present invention.

FIG. 13 a) shows a packaged system incorporating a levitating Coulomb force device and b) presents a packaged system incorporating a levitating Coulomb force device extracting energy from a magnetic field in accordance with the present invention.

FIG. 14 depicts a packaged system incorporating a levitating Coulomb force device that contains a portion a) of a capacitor and c) a second version of a capacitor in accordance with the present invention.

FIG. 14 illustrates the schematic diagram showing b) the adjustable capacitor and d) a pair of adjustable capacitors in a packaged system incorporating a levitating Coulomb force device in accordance with the present invention.

FIG. 15a) presents a packaged system incorporating a levitating Coulomb force device containing an inductor, b) depicts a physical layout of an inductor coil and c) illustrates the schematic of the inductor in accordance with the present invention.

FIG. 21a) presents the superposition of the daughter substrate placed over the mother substrate illustrating the combined symbols as defined in FIG. 20c where the four islands on the mother substrate are charged positively, b) depicts the charging of addition islands on the mother substrate in preparation to move the daughter substrate vertically, c) illustrates reversal of charge placed on the islands located at (2, 1), (5, 1), (2, 4) and (5, 4) to levitate and move the daughter substrate through the potential gradient formed in FIG. 21b and d) reveals that the daughter substrate has moved one division upwards in accordance with the present invention.

FIG. 22a) shows the 2-D structural view of a daughter substrate containing the four negatively charged corner Coulomb islands and two internal islands charged positively, b) presents the superposition of the daughter substrate placed over a mother substrate illustrating the combined symbols as defined in FIG. 20c where the four outer islands on the mother substrate are charged positive, c) depicts the charging of addition islands on the mother substrate in preparation to rotate the daughter substrate, d) illustrates reversal of charge placed on the islands located at (2, 2), (5, 2), (2, 5) and (5, 5) to levitate and rotate the daughter substrate through the potential gradient formed in FIG. 22b and e) reveals that the daughter has rotated 45° and f) depicts the daughter after a rotation of slightly more than 45° in accordance with the present invention.

FIG. 22g) shows that the daughter has rotated another 45° (note that the symbols on the daughter substrate have been corrected due to the 90° rotation) and h) presents the daughter substrate attached to the mother substrate after being rotate 90° in accordance with the present invention.

FIG. 25a) illustrates a mother substrate carrying three daughter and two granddaughter substrates where one of the granddaughters is repositioned, b) reveals further repositioning of the granddaughter, c) shows the second granddaughter being repositioned and d) presents the final reconfiguration of the second inductor connected to the Microprocessor in accordance with the present invention.

FIG. 26a) depicts an accelerometer comprised of a mother and daughter substrate having horizontal offset capacitors, b) illustrates an above view of the horizontal offset capacitors, c) reveals a displacement of the daughter substrate due to a deceleration and d) shows an above view of the horizontal offset capacitors after the displacement in accordance with the present invention.

FIG. 27 presents a 2-D surface view of the offset capacitors a) used to determine movement in the x and y-directions and b) after a deceleration in the −x direction in accordance with the present invention.

FIG. 27 illustrates a 2-D surface view c) of a second embodiment of offset capacitors and d) of a third embodiment of offset capacitors in accordance with the present invention.

FIG. 29a) depicts a system of daughter and grand daughter substrates, b) shows a side view of the connect substrate bypassing the I/O circuits and c) presents a capacitor that is fully charged to provide auxiliary power to a daughter substrate to provide energy to power the Coulomb islands in accordance with the present invention.

FIG. 31a) shows an RF front end connected to a Yagi antenna, b) presents the construction of a Yagi antenna, c) depicts an RF front end connected to a patch antenna and d) illustrates the construction of a patch antenna for higher frequencies in accordance with the present invention.

FIG. 33a) shows cross sectional view of the results of edge processing forming vertical metal sheets, b) presents edge before edge processing, c) depicts the top view of an edge and d) illustrates a side view in accordance with the present invention.

FIG. 34 shows the a) top view and b) side view of two substrates connected on their edges in accordance with the present invention.

FIG. 35a) depicts an RF front end, antenna substrates and other substrates on a mother substrate and b) illustrates the finished construction of a 3-dimentional antenna in accordance with the present invention.

DETAILED DESCRIPTION OF THE INVENTION

Figure 4C:
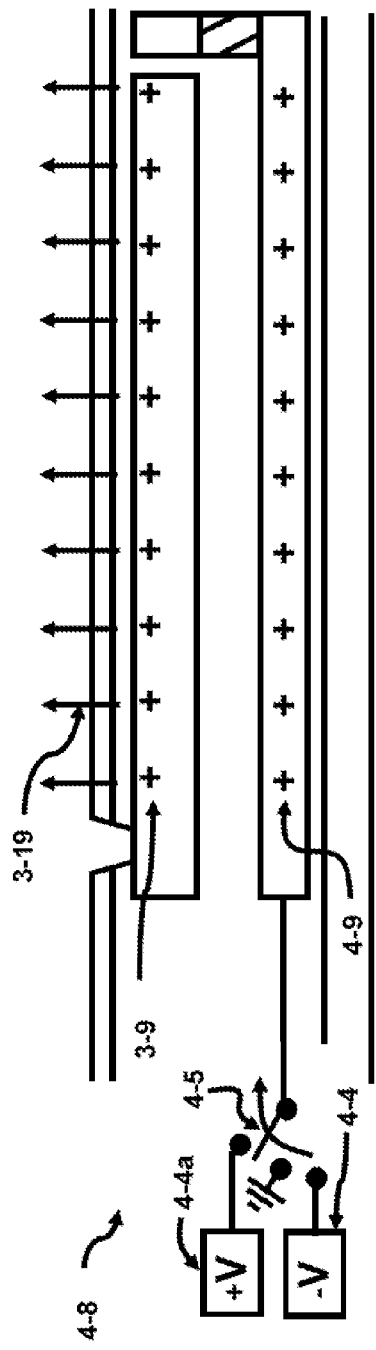

Several inventions are presented and are described in this specification. All the prior art that has been cited fail to show the inventive techniques including, but not limited to: a moving component that; 1) can be detached from its surroundings; 2) can contain Coulomb islands with opposing charges: 3) can freely move by using Coulomb forces formed by Coulomb charges, and; 4) can adjust the charge of the Coulomb islands in both magnitude and polarity.

FIG. 1a shows a reconfigurable system 1-1 which uses Coulomb force to levitate and position the upper substrates on the top surface of the lower substrate. The lower substrate will be addressed as the mother substrate 1-2 while the upper ones (1-6 through 1-12) will be called the daughter substrates in several descriptions. The substrates can be a die, comprised of dice (chips), MCM (Multi Chip Modules), MEMS (Micro-Electro-Mechanical Systems), wafer bonded components or any of the previous combinations. For instance, a memory substrate (or die) has two surfaces (a top and bottom surface) and has four edges, while a third substrate is formed using a wafer bonding process to combine a first and second substrate that are now physically bonded together as one substrate. The third substrate also has a top and bottom surface and has four edges. In addition, once the substrates are fabricated, placed in a system, and levitated the substrate is completely isolated from the remaining portions of the system. Note in this case, some of the daughter substrates can be moved while the mother substrate is rigid or connected to a reference foundation (not shown). In one case, the daughter substrate can turn around the edge of the mother substrate and position itself on the bottom side of the mother substrate. The substrates shown in this description depicts only those components that relate to the idea being conveyed. However, any circuitry, devices or any other components formed by using the technology that fabricated the substrates can also be used to build VLSI systems on that given substrate. The mother substrate 1-2 in this case is a DSP core, although it could be a processor, microcontroller, memory, FPGA, a portion of a MCM, MEMS, or any structure upon which processing steps can be applied to form Coulomb islands or metallic sheets within the mother substrate.

The Coulomb islands can be of a variety of shapes; circular, oval, rectangular or polygon. The Coulomb islands can be perforated or have an ameba shape, for instance, a Coulomb island can be multi-fingered. The daughter substrates are attached and connected to the top surface 1-3 of the mother substrate 1-2. The system 1-1 is currently being used to communicate using a Standard frequency band within the United States as indicated by the incoming 1-13 and outgoing 1-14 electromagnetic radiation carrying voice, data, pictures or video.

While traveling on the road, the user of the system arrives within the domain of a new base station that uses a different frequency range in another Standard frequency band for that region. An automatic sensing unit within the communication device or the user's input is used to command the system 1-1 to reconfigure itself to operate in this different band. To operate in this frequency range, it would be required to replace the Rec-A 1-9, Tran-A 1-8 and Inductor-A 1-11 which were optimum for the prior band with the Rec-B 1-7, Tran-B 1-6 and Inductor-B 1-10 that are optimum for the different band. Replacing the current components with new components offers several advantages at the system level. A few of the advantages are elimination of RF switches which cause loss, reduction of power dissipation (since only a minimum number of devices need to be powered), optimum frequency band optimization (since components that target the desired frequency band are used) and improved quality factor of the inductor. Note that although only one input/output wireless path is illustrated on the mother substrate 1-2, more than one input/output paths can be incorporated into the system 1-1, for example, MIMO (Multi Input-Multi Output) system.

The sequences of steps are outlined in FIG. 1*b* through FIG. 1*g*. FIG. 1*b* shows daughters 1-7 and 1-11 being moved apart, FIG. 1*c* shows daughters 1-6 and 1-10 being moved left, FIG. 1*d* shows 1-8 being moved down, FIG. 1*e* shows 1-9 being moved right, FIG. 1*f* shows daughters 1-6 and 1-9 being moved in opposite directions, FIG. 1*g* shows daughters 1-6 and 1-7 being moved in a clockwise direction, and FIG. 1*h* shows the daughters 1-6, 1-7 and 1-10 in their final position. Note that these three new daughters are placed in the same locations as the previous three daughters. The positions of the electrical interface are common to all replaceable substrates. Communication is reestablished after the daughters make electrical contact after the reconfiguration has completed.

Several alternatives using reconfiguration are possible. This depends on the distribution of the communication system between the mother and daughter substrates. For example, the mother substrate can contain busses which interconnect a portion of the "A" daughters to the "B" daughters and use reassembly-switch substrates that reconfigure the remaining portion of the interconnect between these two sets of daughters and the mother substrate. Another case is for the mother substrate to contain two communication systems and several sets of daughter substrates. One set of daughters substrates can be used to communicate on one band while another set of daughter chips are being reconfigured to be allowed to operate in a different band. This situation may occur at the boundary between the two different base stations to insure that a communication channel is not lost.

The control unit to perform this operation may be shared with all substrates or the control unit may exist within the mother substrate, within one of the daughter substrates which is not being reconfigured, for example, memory 1-12 or a combination of the two. The control unit has a computation component that determines the current position of the daughter substrates and calculates the sequence of steps required to reconfigure the daughter substrates to achieve the desired configuration.

Sensors located between substrates are used by the control unit to determine the identity, location, vertical position, velocity, and direction of movement of the daughter substrates. One form of the sensors can use capacitive coupling between a levitated daughter chip and the mother substrate to transfer this information. In one case, power does not have to necessarily be dissipated in the daughter substrates using the sensors. The sensor signal enters a first plate of a first capacitor in the mother substrate and is capacitively coupled to the second plate of a first capacitor located in the daughter substrate. Electrically this signal is coupled to a second plate of a second capacitor located in the daughter substrate that in turn is capacitively coupled to a first plate of a second capacitor located in the mother substrate. A sensing unit on the mother substrate can measure the total capacitance of the series connected capacitors. This value can be used to derive several physical parameters of the system 1-1 as will be described in a later section. Besides the sensor, the parallel plates on the daughter and mother substrates can be used to form capacitors. These capacitors can also be used to send/receive data, signals, clocks, etc.

The system 1-1 uses sheets of charge to form Coulomb forces. These non-infinite sheets of charge should be isolated from each other by an oxide or dielectric layer. These sheets of charge are also called Coulomb islands. Then by charging these sheets, the Coulomb force that forms between the sheets can be used to perform operations. The sheets can be charged using one of several techniques: 1) being mechanically probed, either using an external probe, such as a testing probe or a MEMS probe; 2) induced charging; 3) F-N (Fowler-Nordheim) tunneling; 4) ion implantation; or 5) by a combination of the previous possibilities. Note that for the first technique, an opening in the oxide layer will be required to allow the entry of the mechanical probe. This opening should be as small as possible to minimize the exposure of the uncovered surface of the element to the outside environment which can make contact with the surface and alter the amount of stored charge on the element. Otherwise, one of the superior aspects of the Coulomb island is that the charge can be held indefinitely. So once the insulated metallic element is charged, the charge remains and the element can be used over and over again without further dissipation in energy to generate a Coulomb force. For example, the Coulomb force formed between two sheets of charge, one on the mother and one on the daughter, can be used to levitate the daughter substrate indefinitely. The metallic element can be a metal, for example, aluminum, copper, gold, or it could be a doped semiconductor like polysilicon.

Most of the charged elements described in this specification are planar in nature where the plane can be a small segment or "Coulomb island" several micrometers on a side forming a metallic planar surface. In some cases, electron implantation can be used to blanket the entire back surface of a wafer with the same charge. The plane in this case would be a large Coulomb island covering the entire backside of the substrate. Note that the charge can be deposited by electron implantation as described in U.S. Pat. Nos. 6,841,917 and 7,217,582. Note that once this charge is placed into the substrate, they cannot be easily changed. Thus, this charge is typically non adjustable after this processing step. In this specification, some of the charge elements that will be described will be called Coulomb islands. Some of these Coulomb islands will have a permanent charge or are charged once, others can be adjusted in magnitude even while the island is performing an operation and is completely detached from the mother substrate, some will have sheets parallel to the surface of the mother substrate, and some with sheets parallel to the edge of the mother substrate. The Coulomb islands are used to generate Coulomb forces that can be used to move the daughter substrates.

A cross sectional view along 1-15a is given in FIG. 1i corresponding to the position of the dotted line 1-15 of FIG. 1h when the daughter substrates are physically and electrically connected to the mother substrate along the surface indicated by 1-3. Several issues surround the details of how this contact is made: 1) an electrical contact establishes electrical connectivity between the substrates; 2) a second electrical contact can also be formed that is capacitive in nature; and 3) the Coulomb force is used to make contact. For example, the physical contact is made by squeezing the daughter substrates to the mother substrate. The squeezing force is created by using the Coulomb force between oppositely charged Coulomb islands. The electrical contacts allow for DC signal (busses, control signals, etc.) and power supply connections (VSS, VDD, VREF, etc.). The substrate maintains stability while the daughter substrates are being levitated or in movement by the use of sensors and a control unit incorporating feedback as will be described later.

Shown are the daughter substrates from left to right 1-8, 1-9 1-6 and 1-12. All are in contact with the mother substrate 1-2. Substrates as defined in this specification will contain a portion for foundation, a portion for holding some of the components (devices, interconnects, via, oxide layers, etc.) that form the circuits and possibly a portion holding mechanical components (MEMS, MCM). The substrates have two portions, for example, substrates 1-2 and 1-12 show a foundation portion (1-16a and 1-16b) and a component portion (1-18a and 1-18b), respectively.

The foundation portion supports the component portion and offers: 1) the ability to handle the substrate without fracturing the substrate into pieces during handling; 2) removal of heat; and 3) possibility of conducting the power supply current (for example, U.S. Pat. No. 4,947,228). In some cases, the substrate is abrasively background to reduce the thickness of the substrate, so they: 1) fit into a final packaged portable system; 2) improve heat transfer; 3) increase flexibility; and 4) reducing the height of stacked substrates (for instance, stacked memory). This foundation portion typically has a thickness ranging from ten's of micrometers to 500 micrometers. It can consist of one or more layers of semiconductor material (silicon, III-V, such as GaAs), an oxide layer ($SiO_2$ . . . ), or a combination of the two. In some cases, the foundation portion could also contain devices (such as devices formed in the semiconductor material), their contacts (source/drain, diffused interconnect, etc.), drilled vias and Coulomb islands. One well known substrate is SOI (Silicon On Insulator). The conventional CMOS (Complementary Metal Oxide Semiconductor) process also falls into this category since the CMOS process typically has a foundation and component portions. The silicon substrate could be epitaxial or bulk construction where an epi or a bulk CMOS wafer can be partitioned to have a foundation portion and a component portion. A few possibilities are suggested but are by no way limiting.

The component portion contains the remaining elements that are required to provide electrical activity, mechanical motion, and electrical connectivity to the substrate. The metal interconnect layers in the component portion comprises; their oxide separation layers, vias, plugs, I/O (Input/Output) pads, power busses, electrical contacts, antennas, inductors, Coulomb islands, moveable metallic components (MEMS) and capacitors. A few of these examples are shown as examples in FIG. 1i which shows the Coulomb islands [see 1-21, 1-22a, 1-22b and 1-20]. An insulator such as an oxide layer completely surrounds the Coulomb island to insure its isolation. Once charged, the island can remain charged indefinitely.

The component portion would be mechanically polished, for instance using CMP (Chemical-Mechanical Planarization), to planarize the top surface of the substrate. After this step, the Coulomb islands which are formed in the component portion create Coulomb forces between the two surfaces more uniformly as the daughter substrate moves over the top surface of the mother substrate since both surfaces are more planar. In addition, when the Coulomb forces cause the mother and daughter substrates to contact, the planarization also insures that electrical contact can be made. FIG. 1i illustrates the electrical contacts 1-19a and 1-19b. These two contacts are exposed at the surface and allow a physical electrical connection such as a power or a DC signal. The surface of the contacts can be co-planar with the surface or may extend above the surface. Several examples will be given.

The electrical contact is formed between the contacts which protrude above the surface of the substrate. This may require another processing step, for example, removing some of the oxide layer from the top surface to expose and form the protrusion of the metal mesa plateau. Also, the post can possibly be plated with gold (Au) or any other non-tarnishing conductive layer. This would allow the mother substrate post to make electrical contact with all daughter metallic pads. This electrical contact will be made by the Coulomb force created between oppositely charged Coulomb islands on juxtaposed substrates. The pattern of the electrical contacts on the daughter substrate that make contact with the mother substrate is called the "footprint." Note that the footprint located on the mother substrate is the mirror image of the footprint of the mating daughter. Any daughter substrates that can be exchanged need to have at a bare minimum have a portion of a footprint in common. The charged Coulomb islands would be positioned below the existing oxide surface even after the processing step of removing the oxide to create the metal post.

Another possibility is to use MEMS to form mechanical contacts and extrude the contacts from a cavity formed in the substrate. These contacts would be forced out using the generated Coulomb force between Coulomb islands so that electrical contact can be made with a conductive plate on a juxtaposed substrate.

Additional portions can be combined together by using wafer bonding. For instance, the bottom of a first substrate can be wafer bonded to the bottom of a second substrate. This layering sequence would consist of the component, foundation, foundation and component portions. The two component portions would contain signals, interconnect and could contain the charged Coulomb islands.

In addition, a charged Coulomb island can be formed on the backside of the substrate using electron implantation. Thus, either the foundation portion or the component portion can contain charged Coulomb islands.

FIG. 1*j* illustrates the situation where the system 1-23 levitates several of the daughter substrates as the gap 1-24 shows to prepare them for movement. The Coulomb islands of the daughter substrate were altered from "positive" to "negative" charge. Since the mother and daughter substrates now have "like" charges on the Coulomb islands, the daughter substrates separate and levitate over the mother substrate. Many details of the illustration have been simplified to present one key idea of levitation disregarding the stability of the levitated substrates which will be described later. Note that the separation can be used to detach the daughter substrates from the power grid network in the mother substrate to significantly reduce the leakage current that each of the daughter substrates would have drawn otherwise. This separation can be performed to reduce the parasitic power dissipation of the system when it is in a power down state.

A flowchart 1-25 is depicted in FIG. 1*k* that provides the steps to position the substrates into their new locations. The first step is occurs at start 1-26, then a question "Are Daughters in correct position?" 1-27 is performed, if not then the daughter substrates required 1-29 and a calculation of movement for all daughters substrates 1-30 is performed by a control unit (not shown), then the required daughters substrates are raised from the mother substrate 1-31, the sequence of movements are preformed 1-32, and the daughters are dropped or connected to the mother 1-33. Otherwise, the system moves to communicate 1-34.

The Coulomb force is used to detach, levitate, move and reattach the daughter substrates to reconfigure the system. The Coulomb force is formed between at least two charged elements. These elements can consist of charged points, lines, planes, or volume distributions. When the elements are point charges, the following equation holds:

$$F = \frac{Q_1 Q_2}{4\pi \varepsilon_r \varepsilon_0 R_{12}^2} \text{ Newtons} \quad (1)$$

where $Q_1$ and $Q_2$ are the point charges, $\varepsilon_0$ is the permittivity of free space, $\varepsilon_r$ is the relative permittivity of free space, and $R_{12}$ is the separation between the charges. The $\varepsilon_r$ for $SiO_2$ is 3.9 while air is 1.0.

The Coulomb forces are linear and the total force due to three point charges ($Q_1$, $Q_2$ and $Q3$) on a reference charge $Q_r$ is the sum of the forces due to the three point charges on the reference charge. The $a_{r1}$, $a_{r2}$ and $a_{r3}$, are unit vectors and $R_{r1}$, $R_{r2}$ and $R_{r2}$ are distances from the reference charge to the other charges in the Cartesian coordinate system. The variables in front of the unit vectors determine the magnitude and sign of the forces:

$$F = \frac{Q_r Q_1}{4\pi \varepsilon_r \varepsilon_0 R_{r1}^2} a_{R1} + \frac{Q_r Q_2}{4\pi \varepsilon_r \varepsilon_0 R_{r2}^2} a_{R2} + \frac{Q_r Q_3}{4\pi r \varepsilon_r \varepsilon_0 R_{r3}^2} a_{R3} \text{ Newtons} \quad (2)$$

Since each unit vector can be comprised of an x, y and z components, each of these three components can be determined separately from Equ. 2.

The electric field intensity on the z-axis due to a circular sheet of charge (see 2-2*a*) in the xy-plane as shown in FIG. 2*a* is:

$$E = \frac{1}{4\pi \varepsilon_r \varepsilon_0} \oint \frac{dq}{r^2} a_r = \frac{1}{4\pi \varepsilon_r \varepsilon_0} \int_r \int_\theta \frac{2\pi \rho_s r dr \cos\theta}{h^2} a_z \text{ Volts/meter} \quad (3)$$

where $\rho_s$ is the surface charge density, r is the radius of the ring with a width dr, and θ is the angle between the z-axis and the side h. This can be simplified to $$E = \frac{\rho_s}{2\varepsilon_r \varepsilon_0} \int_0^\phi \sin\theta d\theta a_z = \frac{\rho_s}{2\varepsilon_r \varepsilon_0} [1 - \cos\phi] \text{ Volts/meter} \quad (4)$$

where φ is the displaced angle measured from a point on the z-axis to the edge of the disk so is a function of z. For instance, a φ of 90° would be an infinite plane while a φ of 45° would be the case where the distance above the circular sheet of charge equals the radius of the circular sheet (where d=r in FIG. 2*a*). As the point along the z-axis approaches (0, 0, 0), the displaced angle increases to 90°.

FIG. 2*b* illustrates on overlapping view 2-3*a* of two Coulomb islands 2-4*z* and 2-5*a*. The islands are metallic and have a radius of r and are separated from each other by the distance of h. Each of these islands can be formed on separate substrates. If both islands are charged, a force F will be exerted against the other. Assume that the Cartesian coordinate system of FIG. 2*a* is superimposed against the image of FIG. 2*b* where the center of the island 2-5*a* is located at (0, 0, 0) while the center of the island 2-4*z* is located at (0, 0, d). Using Equ. 4, the force at (0, 0, d) due to the island 2-5 can be calculated by determining φ. The force exerted between the two islands can be determined if an assumption is made that the entire charge of the island 2-4*z* of charge $\pi r^2 \rho_{sr}$ is located at (0, 0, d). Although this is an approximation, doing so, would result in the approximate force between two circular sheets of charge juxtaposed over one another. As indicated by Equ. 5, as the two islands are brought closer together, φ increases causing the cos() term to decrease and thereby generating a larger force between the two islands.

$$F = \frac{\rho_s \rho_{sr} \pi r^2}{2\varepsilon_r \varepsilon_0} [1 - \cos\phi] \text{ Newtons} \quad (5)$$

where $\rho_{sr}$ is the surface charge density of the island 2-4*z* located at (0, 0, d).

Substrates can have rectangular outlines with various aspect ratios and side dimensions that ranges from a fraction of a millimeter to over a centimeter. FIG. 2*c* presents a graph 2-6 of the gravitation force of three different square silicon substrates 2-9 through 2-11 with the indicated side dimensions where the substrate thickness is the independent variable. The force as indicated by the grouping 2-12 is read from the vertical axis on the left. The substrate thickness is given in micrometers and the thickness of the silicon substrate can be reduced by back grinding. Back grinding can reduce the gravitational force by an order of magnitude as indicated by the points 2-7 and 2-8 where the thickness was reduced to 65 micrometers from over 500 micrometers. Similar curves can be generated using other materials; SiN, GaAs, etc. once their densities are given.

In the graph of 2-6, the right vertical axis provides the voltage necessary to generate a force corresponding to the points 2-7 and 2-8. The islands are positioned as indicated in FIG. 2b and the value r was set to 50 micrometers and the height h was set to 5 micrometers. The system will function at a minimum height that will depend on the degree of planarization of the two mating surfaces. These islands are also called Coulomb islands and the two juxtaposed islands form a pair of Coulomb islands. The relative permittivity of the medium between the two islands is mostly air; so $\in_r$ is set to the value one. Please note this over simplification to simply the analysis; the oxide thickness between the island and the surface of the substrate will be of the order of 1 micrometer. For the following calculations, the oxides were not included. Then Equ. 5 could be solved for $\rho_s$ assuming that the two surface charge densities are equal causing the magnitude of the charge on each plate to be the same. The surface charge density can be multiplied by the area of the island where the island is assumed to have a zero thickness; thereby providing the charge $Q_s$ associated with the surface of the island. The capacitance of these islands is approximately 0.15 femtofarads. Therefore the voltage applied to the islands is:

$$V = \frac{Qs}{C} \text{ Volts} \tag{6}$$

In order to generate the forces associated with the points 2-7 and 2-8, the potential of each island is indicated as voltage. As the magnitude of the potential decreases, the charge for a given C also decreases. Equ. 6 was used to determine that the voltage 74 and 220 volts are required for one pair of Coulomb islands to generate the force $10^{-4}$ and $10^{-3}$ newtons, respectively.

The force has been estimated using only one pair of Coulomb islands and it has been assumed that the entire electric field is used to generate this force. Thus, by reducing the thickness of the substrate and thereby decreasing its weight by an order of magnitude, the required potential can be decreased almost three times. This has a big impact on several issues, some are: 1) lower voltages stress the parasitic diode junctions of the substrate less; 2) lower voltages reduce the stress the gate, drain and source of the devices on the substrate; and 3) generating lower voltages will drop the power dissipation. Some of the electric field lines of the Coulomb island in a conventional process without any special considerations will terminate back into the substrate and reduce the Coulomb force between the two substrates. The thickness of the component section of a substrate is less than 10 micrometers (each metal/oxide layer consumes about 1.5 to 2 micrometers) so some of the force will be lost in the substrate unless special modifications are made, for example, the use of Faraday shields. Oxide substrates also help to deduce the loss. When substrates are levitated over the mother substrate, a minimum distance of separation needs to be determined. This helps in several ways: 1) a smaller distance of separation requires less voltage which in turn dissipates less power; 2) a lower voltage reduces the stress of materials due to high electric fields; and 3) as the daughter substrate decreases in area, the ability to maintain the daughter substrate stable at greater distances of separation becomes more difficult. If each of the surfaces are planar to within +/−1 micrometer over a large area, then a separation of slightly more than 4 micrometers should be a comfortable distance between these two large area substrates. However, the amount of required separation between the substrates may need to be evaluated for each daughter substrate.

Several of the special conditions include layout and processing techniques: 1) the introduction of a Faraday shield as discussed later helps to prevent some of these electric field lines from terminating back unto the substrate; 2) any unrelated metallic regions near the islands should be placed further away from the islands; and 3) any heavily doped substrate elements that can terminate these lines can be etched away to remove their presence if possible. SOI (Silicon On Insulator) is a good candidate to reduce the lines terminating on the substrate for the third point mentioned above.

Although one pair of islands can generate the force necessary to overcome the gravitational force, applying the force to a 1 cm$^2$ substrate would require careful placement of the pair of islands and careful application of the force to lift the substrate. Besides, the high values of voltages that were determined earlier would cause a voltage breakdown to occur in the air between the Coulomb islands. Another feature of this invention is the ability to place multiple pairs of Coulomb islands over the surface of the substrate. The spreading of the pairs of Coulomb islands over the surface of the substrate has several benefits: 1) the force can be evenly distributed to lift the substrate equally and more controllably; 2) the force that each pair of islands must generate is the total force divided by n, where n is the number of pairs of islands; 3) since the force per island decreases, the required voltage to generate this force also decreases, which reduces the voltage stress that is applied to materials in the substrate even further; 4) with a large number of pairs of islands, various combinations of potential variations applied to and among them allow a myriad of manipulations available to the levitated substrate; and 5) the stability of controlling the levitated substrate becomes easier since the forces are spread over a larger area.

The voltage stress involves the various seimiconductor diode junctions, oxide and air breakdown concerns. Diodes can breakdown when a maximium reverse voltage is applied across the junction. The source/drain regions of an MOS device, the emitter/base/drain junctions of a BJT, and parasitic diode formed during manufacturing are examples of diodes. Similarly, thin oxides as formed between the gate and channel of an MOS device have a breakdown voltage. As the number of island pairs increases, the voltage required to generate the net Coulomb force decreases; thereby, reducing the voltage stress.

An example is described to explain how the voltage that is applied to a multiple of islands can be decreased as the number n of island pairs increases. In FIG. 2c, a potential of 220 volts is required to generate a first force of $10^{-3}$ newtons for a 1 cm×1 cm substrate with a thickness of 500 micrometers. A potential of 74 volts is required to generate a force of $10^{-4}$ newtons for a 0.4 cm×0.4 cm substrate with a thickness of 500 micrometers using a similar island pair. In FIG. 2d, these two points correspond to the points 2-18 and 2-17, respectively. If ten pairs of islands are spread over the surface of these substrates, the magnitude of the potential that is required on each island is 69 and 23 volts, respectively. At a hundred pairs of islands, the magnitude of the potential is 22 and 7.3 voltages, respectively. When 1000 pairs of islands are used the potential applied to each island is only 7 and 2.3 volts, respectively, as indicated by the point 2-20 and 2-19. Thus, as the number of islands is increased, the potential that needs to be applied to the islands is decreased, thereby decreasing the voltage stress applied to and between the substrates in the system. The breakdown voltage of air, Si and SiO2 are approximately 3E4, 3E5 and 5E6 volts/centimeter, respectively. The shaded area indicates where the breakdown voltage of air would not be exceeded for a gap of 5 micrometers. Fortunately, an oxide layer coats each Coulomb island and this would tend to increase the maximum breakdown voltage between two juxtaposed Coulomb islands. Secondly, if the thickness of the substrate is decreased, the new set of the three corresponding curves in FIG. 2d would be shifted downwards offering the possibility of these substrates having lower numbers of Coulomb islands.

FIG. 2d(1) reproduces FIG. 3 from a publication by R. Fearing entitled "Survey of sticking effects for micro parts handling", Intelligent Robots and Systems 95, Proc. 1995 IEEE/RSJ Inter, Conf. Aug. 5-9, 1995, pp. 212-217. FIG. 2d(1) depicts the gravitational, electrical, van der Waals and surface tension where the attractive force is between a sphere and a plane. In a dry air environment, a situation where the Coulomb forces of our invention can be utilized, surface tension can be disregarded. Thus, we see that gravity equals the van der Waals force at a radius of about 200 micrometers. Note that the electrostatic force exceeds the van der Waals at a radius of about 1 millimeter. The final design that is chosen needs to balance the mass of the substrate (gravity) against the number, planar area and voltage of the Coulomb islands. For smaller substrates, these variables need to be reexamined to safely overcome the van der Waals force.

FIG. 2e depicts a substrate 2-21 with a foundation portion 2-2 supporting the component portion 2-4 and the division between them 2-22. A coulomb island 2-23 is located in 2-4. The island 2-23 is charged positively 2-25. Negative charges or impurities 2-24 can attach to the surface of a substrate in an uncontrolled environment. This condition would attempt to neutralize the benefit of fabricating a coulomb island since the electric field intensity formed outside of the substrate is reduced. A hermetically sealed package and better passivation procedures can be used to reduce this concern.

FIG. 2f and FIG. 2g both depict the cases (2-26 and 2-28) where the exposure to an environment containing impurities is reduced and the electric field intensity extends away 2-27 and into 2-30 due to the positive charge 2-25 and the negative charge 2-31 in the coulomb islands 2-23 and 2-29, respectively. The coulomb islands should be as close to the surface of the substrate as possible to maximize the force that would be applied to an opposing and juxtaposed substrate that contain charged Coulomb islands.

FIG. 3a reveals a cross section view of a substrate 3-1 containing a Coulomb island 3-5 in the component portion 2-4 with an access opening 3-2 for a probe. The top surface 3-3 may be covered with an oxide layer and a pacification layer 3-4. The Coulomb island 3-5 should be placed as close as possible to the surface 3-3 and as far as possible from any unassociated metallic conductors in the region 3-6. It is desirable to have the electric field intensity lines exit the surface 3-3. This would provide greater control of the levitation process if the electric field intensity was prevented from being terminated in the substrate. If not stated explicitly, numbers (e.g., 2-2) which were identified earlier carry the same meaning.

FIG. 3b shows 3-7 and the formation of a positive 3-10 and negative 3-11 charges forming on the top and bottom of the Coulomb island 3-5, respectively. By bringing a negatively charged sheet 3-9 in an external plate 3-8 close to the Coulomb island 3-5, induced charging causes the charge distribution on the coulomb island to have a positive sheet 3-10 adjacent to the plate 3-8 and a negative sheet 3-11 formed on its opposing side. Note that the total charge on the Coulomb island 3-5 is currently neutral. Furthermore, for the quasi-static case, the electric field intensity inside the Coulomb island 3-5 is zero and all induced charges move to the surface of the Coulomb island 3-5. The charge distribution is shown to be evenly distributed; however, the shape of the metallic sheet can cause some of the changes to group at the corners and create an uneven distribution. To simplify the discussion, an even distribution over the surface was assumed. Furthermore, note that the positively induced charge of 3-10 formed in the Coulomb island 3-5 now attracts the negatively charged sheet 3-9 in the external plate 3-8. This is known as the induced force.

The next step is to remove the negative charge from the coulomb island 3-5. FIG. 3c illustrates the situation 3-12 when a probe 3-14 which is connected to ground is connected to the island through the opening 3-2. The negative charge 3-13a is discharged to ground indicated by the path 3-13. FIG. 3d shows the probe 3-14 being disconnected from the island 3-5. The positive charge is located on the top surface of the Coulomb island as illustrated in 3-15 due to the presence of the negatively charged plate 3-8.

Once the plate 3-8 is removed, as illustrated in FIG. 3e, the positive charge 3-9 redistributes itself over the surface of the coulomb island 3-5 to insure that the electric field intensity parallel to the surface of the coulomb island 3-5 is zero. This redistribution of charge causes the formation of two electric field intensities 3-17 and 3-18 in opposing directions. FIG. 3f shows the surface view 3-19 of the coulomb island 3-5. An approximate representation of the charge distribution 3-9a on the surface of the island is depicted in the view 3-19. Although a rectangular island is illustrated, the island can have a variety of shapes; circle, square, triangular, or any geometric shape bounding a surface area. Furthermore, these islands can also contain perforations or openings within the boundaries of the shape. Charges in metal tend to move towards the sharp corners and by the proper placement of these opening (which create corners) the regular distribution of corners can offer a more uniform charge distribution over the surface of the shape. Since the islands can have variety of shapes, this specification will use the rectangular island (unless mentioned otherwise) without openings to simplify the diagrams and provide a simple explanation of the invention. Note that the dotted line 3-20 in FIG. 3f represents the cross sectional view illustrated in FIG. 3e.

The cross sectional view 4-1 in FIG. 4a illustrates the introduction of a second plate 4-2 juxtaposed and placed beneath the Coulomb island 3-5. The plate 4-2 can be set to a given negative 4-4, ground, or a positive 4-4a voltage potential using the switch 4-5. Setting the switch to the minus voltage 4-4 creates a negative charge distribution 4-3 on the plate 4-2. The electric field intensity 3-18 starts at the positive charge 3-9 and terminates on the negative charge 4-3. The net electric field intensity leaving the surface of the substrate is indicated by the electric field intensity 3-19. The corresponding top view 4-6a is given in FIG. 4b. Note that by comparing the surface charge distribution 3-9a in FIG. 3f with the surface charge distribution 3-9b illustrated in FIG. 4b, the potential applied to the plate 4-2 can be adjusted to decrease the surface charge distribution 3-9b (visible by the reduced number of "+" symbols). The electric field intensity 3-19 leaving the top surface of the coulomb island 3-5 has been reduced. The plate 4-2 creates a Faraday shield for the Coulomb island 3-5. The Faraday shield is a metallic sheet and coupled metal components (vias, traces, etc.) that act together to shield the Coulomb island from the remainder of the substrate. The shield which is fabricated in the substrate is a barrier which attempts to give the Coulomb island autonomous behavior independent of the remainder of the substrate. Ideally, the Faraday shield should isolate the Coulomb island. For example, the metal trace/via stack 4-6 which extends the Faraday shield surrounding the island can be used all around the perimeter of the Coulomb island. This would help provide a better isolation of the Coulomb island. A second feature of the Faraday shield is that a potential can be applied to the shield to influence the behavior of the Coulomb island. The adjustment of the negative potential 4-4 can be used to directly alter the surface charge distribution which in turn alters the electric field intensity 3-19. This is one of the benefits of the Faraday shield since the electric field intensity associated with the top surface of the coulomb island can be adjusted which in turn can be used to control the Coulomb force being applied to another juxtaposed and closely spaced Coulomb island. The cross sectional view given in the diagram 4-1 corresponds to the dotted line 4-7 in FIG. 4*b*.

Figure 4D:
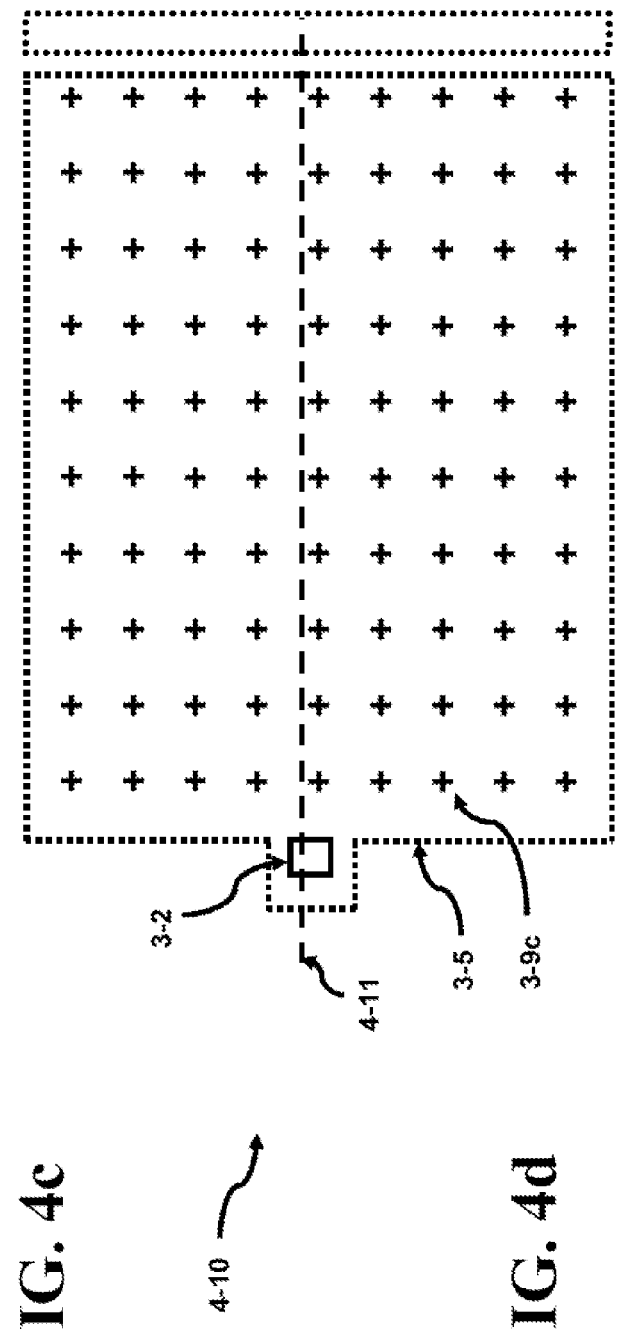

FIG. 4*c* illustrates the case 4-8 where the voltage potential 4-4*a* which is positive is applied to the plate 4-2. A sheet of positive charge 4-9 forms on the plate 4-2. The positive potential on the plate 4-2 causes the electric field intensity 3-19 to increase. As before by adjusting the magnitude of the voltage potential 4-4*a*, the charge distribution 3-9*c* in FIG. 4*d* can be increased. Thus, the Faraday shield can be used to control the electric field intensity 3-19 and thereby control the magnitude of the Coulomb force being applied to another juxtaposed charged Coulomb island. In addition, the voltage potentials (4-4 and 4-4*a*) can be applied to the switch 4-5 using either externally provided voltages or by generating the voltage potentials on chip using well know voltage generating circuits such as charge pumps which are used widely in non-volatile memories.

FIG. 5*a* shows a cross sectional view 5-1 of a Coulomb island 5-8 with a Faraday shield 5-7, separated by an oxide layer 5-8*a*. An oxide layer 5-8*b* is beneath Faraday shield 5-7. Two small openings 5-3 and 5-4 in the oxide allow both plates to be mechanically probed. Since the Faraday shield 5-7 is further below the surface 5-2, a via 5-6 and metal plug 5-5 form the contact and provides an ohmic path to the probe point 5-4. One of the advantages of probing the metallic plate is that once the probe establishes a charge on the plate, the leakage resistive path is very high once the probe is pulled away allowing the island or shield to maintain the charge for a long time. This probe can be an external probe (test-like) or an internal one (formed by a MEMS structure). However, if semiconductor switches are used to deposit charges onto the metallic plates, the device provide a leakage path and will discharge the plate in a shorter amount of time. In this case, the plate would have to be periodically re-charged at specified intervals. On the other hand, in the case of the external probes, the Coulomb island and Faraday shield can be charged during the testing of the device at wafer level. Once the wafer is sawed into individual substrates (dice) these substrates using a pick and place tool can be placed on a mother substrate which has its Coulomb island and Faraday shield similarly charged. The Coulomb forces developed between the Coulomb islands on the mother and individual substrates can be used to hold the substrates together. The next step would be to prepare these components for package assembly. Then, once the packaged device is complete, the daughter substrates can be reconfigured into a desired system.

FIG. 5*b* shows a cross sectional view 5-9 of a probe 5-10 applying a negative voltage 4-4 to the Coulomb island 5-8. The negative voltage causes charge to form at the surface as the sheets 5-13 and 5-14. Note that in reality the charge covers all sides of the island to reach an equilibrium condition although only the top and bottom of the island have been discussed to simplify the explanation. The lower sheet of charge 5-14 causes the shield 5-7 to build an induced charge of a positive sheet 5-11 and a negative sheet 5-12 as shown.

Figure 5C:
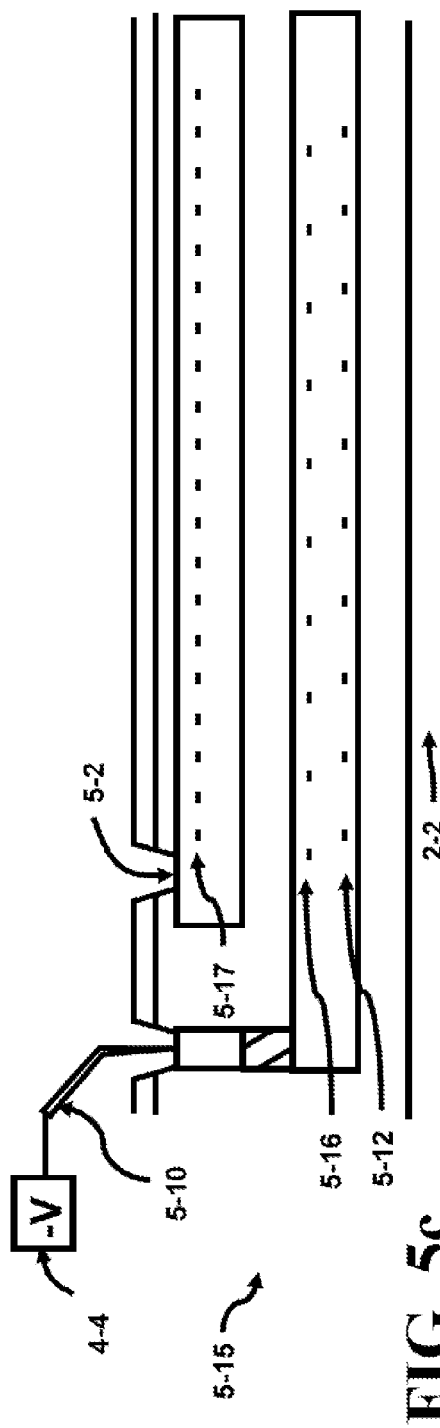
FIG. 5a) presents the cross sectional view of the Faraday Shield, b) depicts the cross sectional view of a negatively charged plate causing an induced charge to form on a second chargeable plate in a reconfigurable system, c) illustrates a negative probe canceling the excess positive charge of the second chargeable plate of the cross sectional view of the Faraday Shield, d) reveals a negative charge on the second plate, e) the island set to a negative potential and f) the shield set to a negative potential in accordance with the present invention.
Figure 5D:
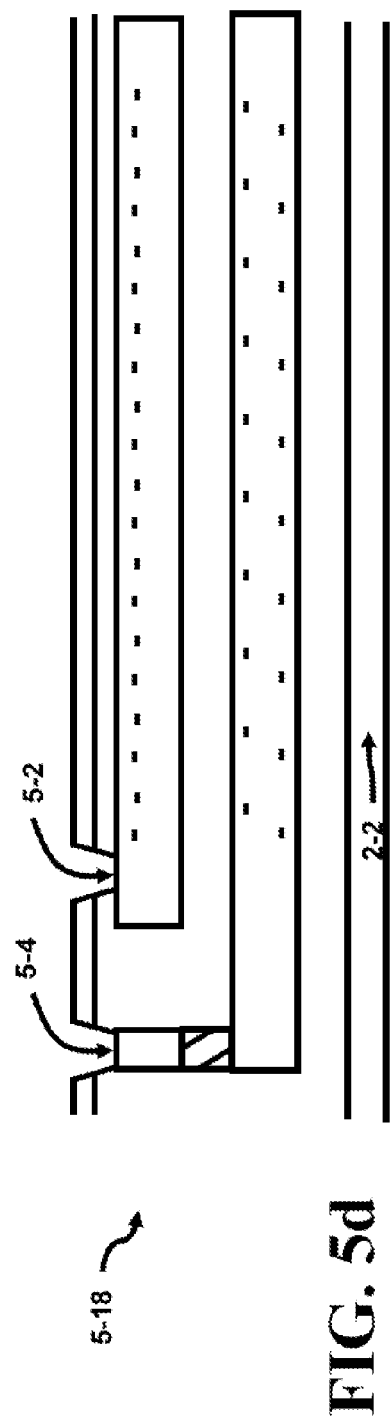

FIG. 5*c* shows a cross sectional view 5-15 of a probe 5-10 applying the negative voltage 4-4 to the Faraday shield 5-7 through the opening 5-4. The potential can be adjusted to form negative sheets of charge 5-16 and 5-12 on the surface of the shield 5-7 and a negative sheet of charge 5-17 on the surface of the island 5-8. FIG. 5*d* illustrates the final cross section view 5-18 once the probe is removed. The Faraday shield 5-7 can be used to shield the Coulomb island 5-8 from the remaining substrate beneath the shield.

FIG. 5*e* shows a cross sectional view 5-19 of a negative voltage supply 4-4 applying the negative voltage 44 through the switch 4-5. The potential can be adjusted to form negative sheets of charge 5-13 and 5-14 on the surface of the island 5-8. An induced positive charge 5-11 is formed on the surface of the shield 5-7 and a corresponding negative charge 5-12 on the opposite side. As in FIG. 4*a*, a metal trace/via stack is formed on the right top side of the shield. FIG. 5*f* illustrates the final cross section view 5-20 once the shield is has a negative potential 4-4*b* applied through the switch 4-5*a*. The Faraday shield 5-7 is charged negatively as indicated by the two sheets of charge 5-12 and 5-16. The Faraday shield 5-7 shields the Coulomb island 5-8 from the remaining substrate beneath the shield.

Since the island and shield in FIG. 5*f* are connected to switches and power supplies, there will be a parasitic leakage path through the circuitry to slowly reduce the charge that is stored on the shield and island. This charging is volatile and will always require that the charge is replenished at periodic intervals. Power dissipation occurs when the shields and islands are charged; however, the performance of this charging circuit can be quite fast since active drivers with low impedance can charge and discharge the shields and islands in nanoseconds. The non-volatile islands/shields, those fully surrounded by a dielectric layer, can retain the charge for years and can maintain a substrate levitated during this time period. A combination of volatile and non-volatile charged islands/shields can be used to move substrates during a reconfiguration of a system; the determination of which one to use will depend on the requirements given in a specification of the design.

FIG. 6*a* illustrates a prior art FAMOS (Floating Gate Avalanche-injection MOS Memory) device 6-1. The foundation portion 2-2 supporting the component portion 2-4 is shown. The foundation portion holds the source 6-3/drain 6-5 and the channel of the device (not shown). The component portion 24 has the oxide layers with thicknesses 6-7 and 6-4 that isolate the floating gate 6-6 with a height 6-8. A view from the top is indicated by the arrow 6-2.

FIG. 6*b* depicts the top view 6-2 of the source 6-3 and drain 6-5 along with the floating gate 6-6. The floating gate 6-6 in this device is completely surrounded by oxide; thus, the gate is isolated from the remainder of the device 6-1. The opening to the source/drain regions are formed by the contact openings 6-9. F-N (Fowler-Nordheim) tunneling is used to charge the floating gate 6-6 and since the floating gate 6-6 is insulated, the charge can be held indefinitely. This is known as a non-volatile device since the charge can be held even after the power is removed from the substrate. This is another way of charging the insulated sheet; however, the sheet or the floating gate 6-6, in this case, is close to the substrate and can have a large area. Thus, the electric field intensity would mostly exist mostly in the gap between the floating gate 6-6 and the channel of the device (within the thickness 6-7).

Figure 6C:
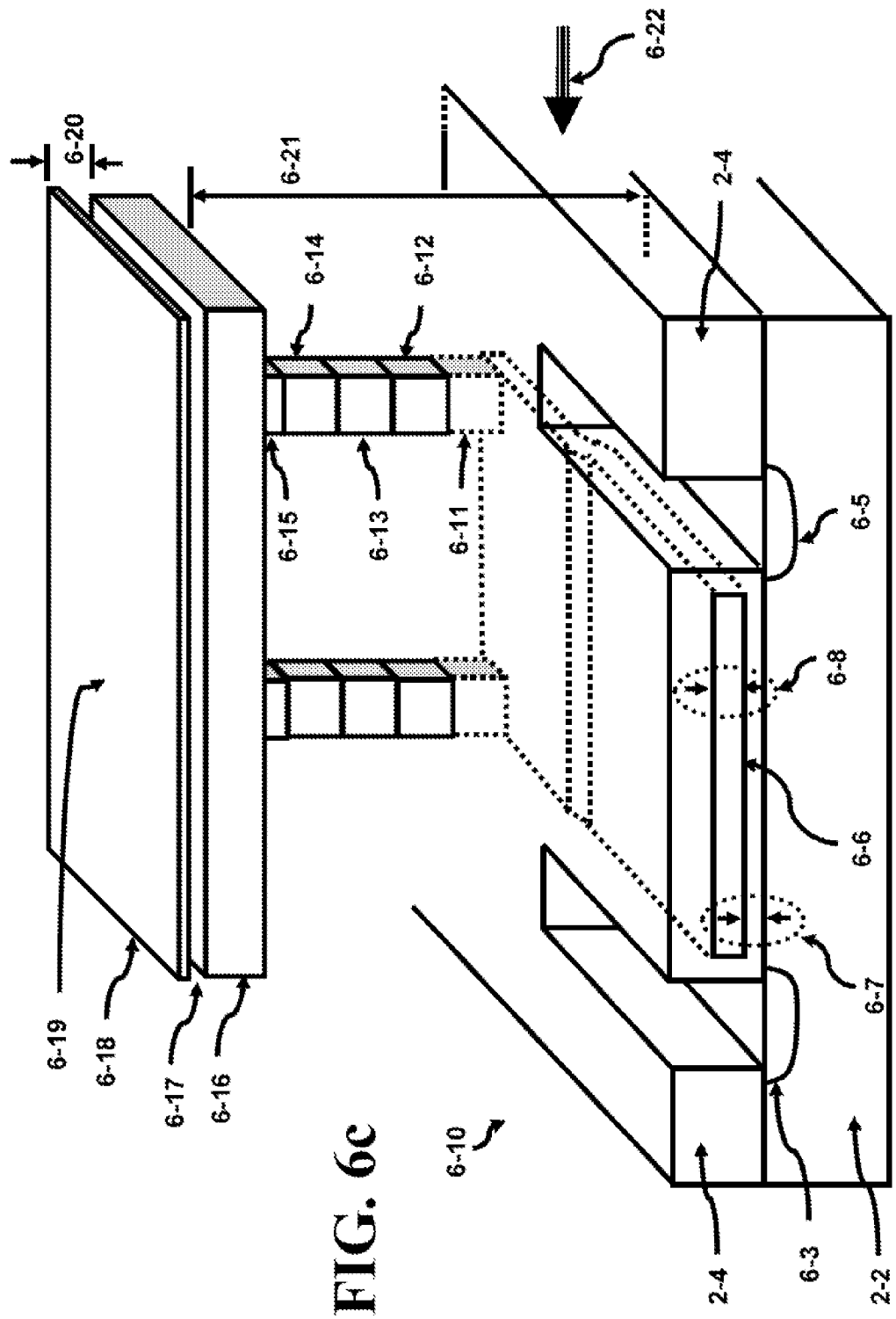
FIG. 6c shows the 2-D with perspective of a chargeable plate connected by metallic stacks to the gate of the FAMOS device in accordance with the present invention.

As shown in FIG. 6c, the 2-D view with perspective 6-10, shows the FAMOS device connected through a series connection of vias and metal plugs (6-11, 6-13, 6-15 and 6-12, 6-14) to the Coulomb island 6-16 which is located close to the surface 6-19 of the substrate. The component region 2-4 includes all components between the foundation portion 2-2 and the surface 6-19. This region is used to form the components such as the oxides, vias, metal plugs, metal wires, Coulomb island, pacification layer, etc. The pacification layer is the oxide 6-17 and 6-18 layers. The distance of the Coulomb island 6-16 from the surface 6-19 is shown as 6-20 while the distance to region 2-2 is 6-21. F-N tunneling of the floating gate 6-6 can be used to charge the Coulomb island 6-16. Particularly since the floating gate 6-6 is now resistively connected to the Coulomb island 6-16 through the vias and metal plugs. The area ratio of the floating gate 6-6 to the Coulomb island 6-16 is a variable and can be controlled to achieve the desired charging rate of the island 6-16. Note that the entire stricture comprising the poly floating gate 6-6, the vias/plug stack and the Coulomb island 6-16 are isolated from the remainder of the substrate by an oxide barrier. The arrow 6-22 indicates the cross sectional view given in the next Figure.

Figure 6D:
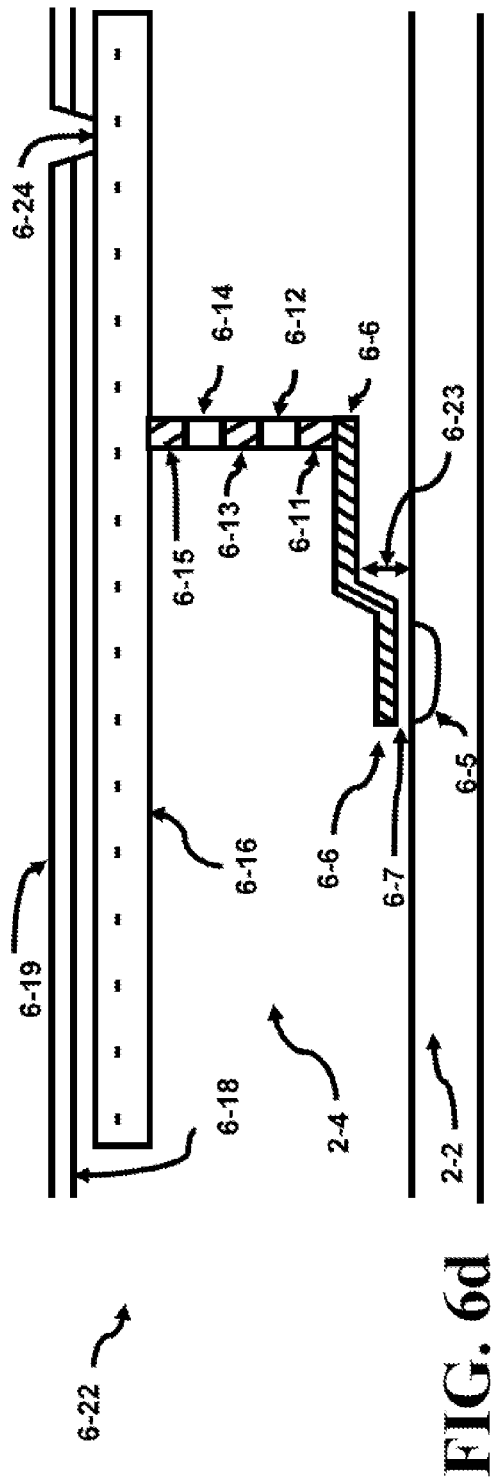
FIG. 6d) presents the cross sectional view 6-22 of FIGS. 6c and e) reveals a Faraday Shield formed beneath the chargeable plate in accordance with the present invention.

A cross sectional view 6-22 of the 2-D view with perspective 6-10 is illustrated in FIG. 6d. All similar numbered items correspond to the same definition as given earlier. The floating gate 6-6 is shown to step up due to the field oxide with a height of 6-23. The drain 6-5 of the FAMOS device is shown and is superimposed over the source 6-3 preventing its view. An optional opening 6-24 allows a probe to charge the island 6-16 and the elements that are ohmic connected to the islands.

Figure 6E:
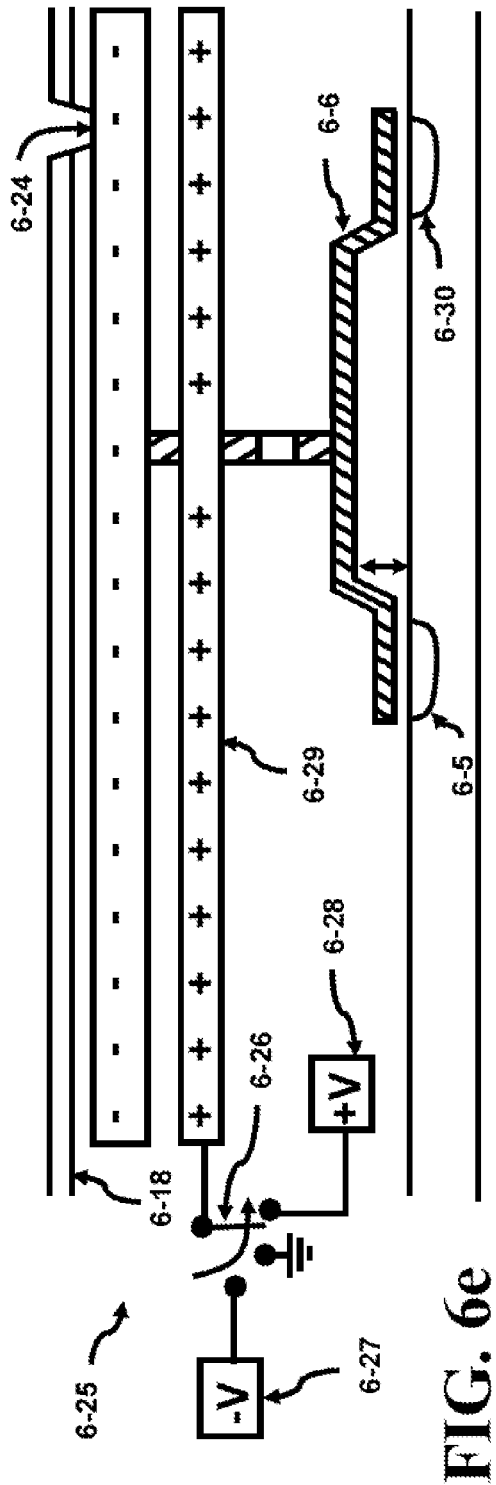
FIG. 6a) illustrates a cross sectional view and b) reveals the top view of the FAMOS device illustrating the source, drain, gate and contact window.

The Faraday shield 6-29 has been added in the cross sectional view 6-25 as indicated in FIG. 6e. The benefits of the Faraday shield 6-29 were described earlier and do not require further explanation. The shield 6-29 can be grounded or switched through switch 6-26 to either a positive 6-28 or negative 6-27 potential. The via/plug stack passes through the Faraday shield 6-29 without making contact to the shield. In addition, the Coulomb plate can be connected to other non-volatile devices simultaneously as illustrated by the partial view of the device having the drain 6-30. The FAMOS device with the drain 6-5 can be used to charge the island 6-16 to a negative potential while the additional non-volatile device with the drain 6-30 depending on its design can be used to remove the negative charge, inject (positive charges) holes or remove holes. Thus, several non-volatile devices can be connected to the Coulomb island 6-16 simultaneously where each non-volatile device can perform a different functional procedure of charging/discharging the Coulomb island.

Figure 7A:
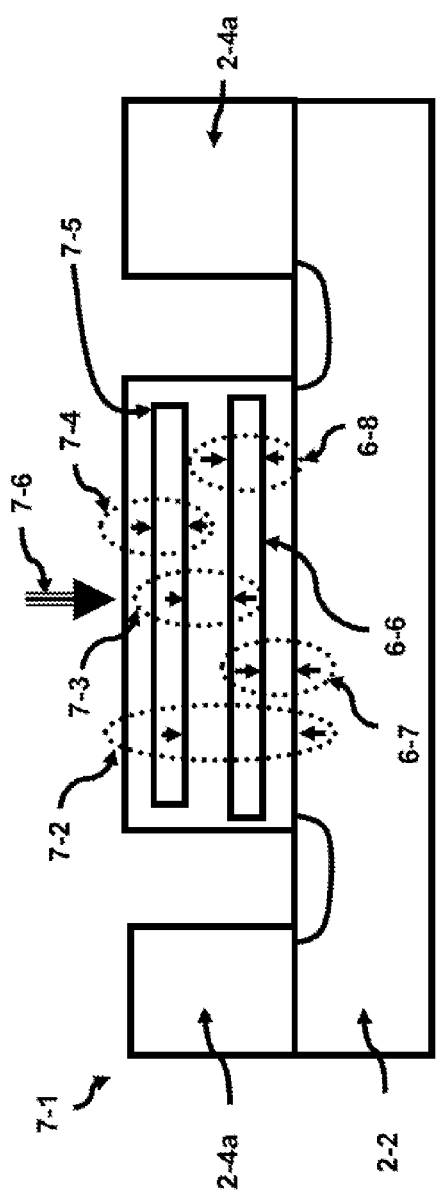
FIG. 7a) illustrates a cross sectional view and b) reveals the top view of the SAMOS device illustrating the source, drain, gates and contact window.
Figure 7B:
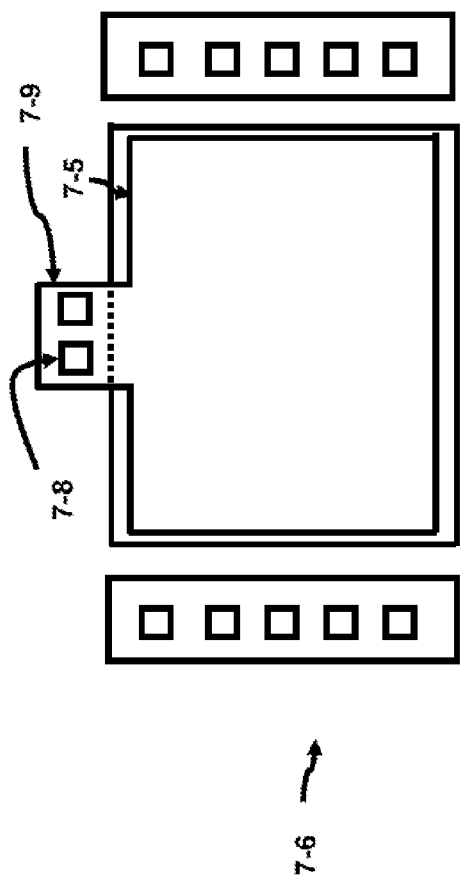
FIG. 7c) presents the cross sectional view of a chargeable plate connected by a metallic stack to the gate of the SAMOS device, d) reveals a Faraday Shield formed beneath the chargeable plate, e) shows the chargeable plate having a positive charge formed either by induced charging or probing and f) presents a voltage adjustable Faraday Shield beneath the chargeable plate in accordance with the present invention.

FIG. 7a depicts a prior art SAMOS device 7-1. This is very similar to the FAMOS device with the exception that an additional gate 7-5 has been stacked over the floating gate 6-6. These devices are also known as a EEPROM (Electrically Erasable Programmable Read Only Memory). The gate 7-5 is called the control gate and is used to enable the erasure and programming of the non-volatile device. The control gate is connected to a voltage source and is separated from the lower gate by the distance 7-3 and is separated from the foundation by the distance 7-2. The thickness 7-4 of the control gate 7-5 is shown. The arrow 7-6 indicates the view given in FIG. 7b. The top view 7-6 illustrates the control gate 7-5 with an overlap area 7-9 that contains two contacts 7-8.

Figure 7C:
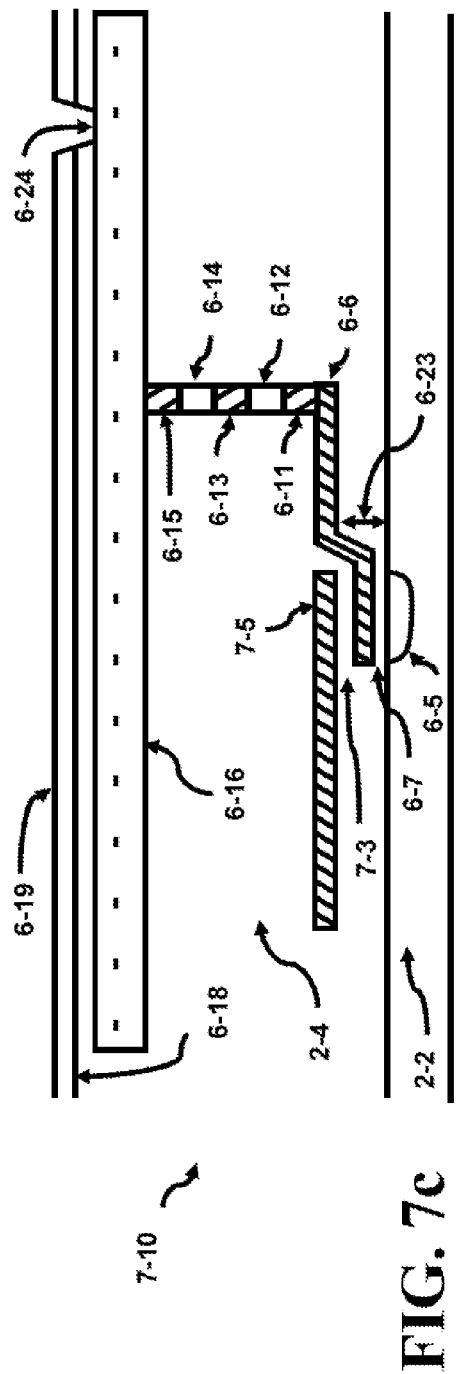

A cross sectional view of the SAMOS device is given in FIG. 7c along with the inventive Coulomb island 6-16 which is charged negatively (either by the non-volatile device with the drain 6-5 or by probing the optional opening 6-24) and is connected to the floating gate 6-6 by the stacked via/plug structure 6-11 through 6-15. The via/plug structure shows that the substrate uses three levels of metal; the invention is not limited to this but can be used in any multi-metal layered substrate. Although, the non-volatile device has been shown to be under the island 6-16, the non-volatile device can also be located in areas where there is no island overhead. The numerical identifiers that match the identifiers mentioned earlier are similar in nature.

Figure 7D:
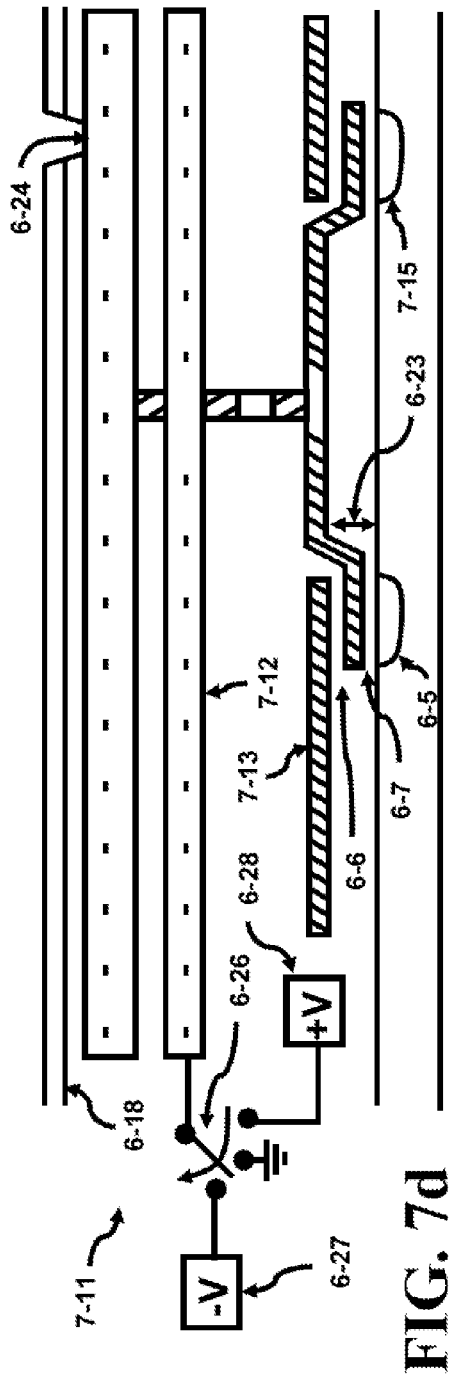

In the cross sectional view 7-11 given in FIG. 7d, a Faraday shield 7-12 has been added below the island 6-16 and can be connected to a variable power supply. The switch can be mechanical (MEMS) or formed from active devices.

FIG. 7e illustrates the cross sectional view 7-14 where the Coulomb island being charged positively by the device with the drain 7-15 which energizes holes in the channel and injects them into the floating gate 6-6. Finally, the cross sectional view 7-16 shows the introduction of a Faraday shield 7-12 that is charged positively by the potential supply 6-28. As before, the device associated with the drains 6-5 and 7-15 can be different devices that perform different F-N tunneling capabilities (i.e., electron charging, hole charging, discharging electrons, discharging holes).

Wafer bonding can be used to create various substrate structures. FIG. 8a shows a cross sectional view 8-1 showing two substrates 8-2 and 8-4 that are part of their respective wafers. The substrate 8-2 can be comprised of a component layer 8-3, while the other substrate can have a blanket coverage 8-5 of electrons 8-6 that were injected using an electron gun (for example, see U.S. Pat. No. 7,217,582). The two substrates can be wafer bonded together to form the final substrate as illustrated in FIG. 8b. The interface 8-8 joins the two substrates 8-2 and 8-4 into the final substrate 8-7.

The cross section view 9-1 in FIG. 9a illustrates two substrates 9-2 and 9-3 forced or held together by the Coulomb force generated by the negative charged island 9-7 and the positive charged island 9-8 which are separated from each other by the distance 9-6. The opposite charge on each island causes an attractive force to develop. Their common surface is 9-4 and the electric field intensity 9-5 starts on a positive charge and terminates on a negative charge. Note that the conventional CMOS process can be used to form these charged islands; thus, for some of the inventions presented in this specification MEMS processing is not used. This cuts down the mask count to perform the processing of the substrate and decreases the cost.

FIG. 9b illustrates the cross sectional view 9-9 where the charge of the top island 9-8 has been changed to a negative charge. Now the two islands repel one another as depicted by the increased displacement of the distance 9-10. In addition, the electric field intensity 9-12 lines terminate on the negative charge in both islands and arrive from outside both substrates 9-2 and 9-3. An assumption is made here that the remaining portions of the substrate do not contain charges. This is an over simplification, since the substrates as shown would contain some positive charges such that some of the lines of the electric field intensity would start from them and terminate on some of the negative charges within either island. The displacement 9-11 between the substrates in that case would be less than what is illustrated. A way of recovering some of the displacement 9-11 would be to introduce Faraday shields into each substrate.

FIG. 10a illustrates the cross section image 10-1 of two substrates (10-17 and 10-18). The top substrate 10-17 has multiple Coulomb islands 10-2 through 10-8 while the lower substrate 10-18 has the Coulomb islands 10-9 through 10-15.

This is the first presentation of multiple islands on one substrate. These islands help to explain how the substrates can be repelled from one another yet remain in levitation state. For example, the islands 10-2, 10-3 10-7 and 10-8 from the top substrate 10-17 are repelled from the underlying islands 10-9, 10-10, 10-14 and 10-15 within the lower substrate 10-18, respectively, since they have a like charge. However, the inner islands 10-4 through 10-6 of substrate 10-17 attract the islands 10-11 through 10-13 of substrate 10-18 since their charges are opposite. The charges on the islands 10-4 through 10-6 have an increased positive charge as indicated by the double "plus" signs. These charge distributions on the islands causes the two substrates to be separated by the distance 10-16.

In FIG. 10b, 10-19 illustrates the situation where the increased charge on the islands 10-4 through 10-6 has been reduced from the initial value. The charge can be altered by using one of the earlier techniques given; such as, F-N tunneling or Faraday shield potential variation, for example. Thus, the attractive force decreases and causes the distance 10-20 between the two substrates to increase which adjusts the height of the daughter substrate.

What has not been shown is how the substrates remain in a stable position once they are separated and levitated. There are sensors on the substrates that can measure their distance at several points of the surface of the substrate and provide feedback information to a control unit that can use this information to adjust the amount of charge in the islands. Doing so allows the substrate to remain levitated and in equilibrium. This daughter substrate control unit can be located either in the daughter substrate, in the mother substrate, or distributed between both. This forms a feedback system which dynamically corrects for and adjusts the position of the two substrates to each other. The sensors can be capacitive in nature and can be used to measure distance, acceleration, velocity, position or identity of each substrate. An additional control unit that orchestrates the movement of all daughter substrates with respect to one another can also be used. The additional control unit can also be in communication with the daughter control unit. In addition, the sensors can also be mechanical in nature as well. A MEMS structure can be used for an accelerometer and can be mounted on a daughter substrate to monitor its acceleration.

Figure 11A:
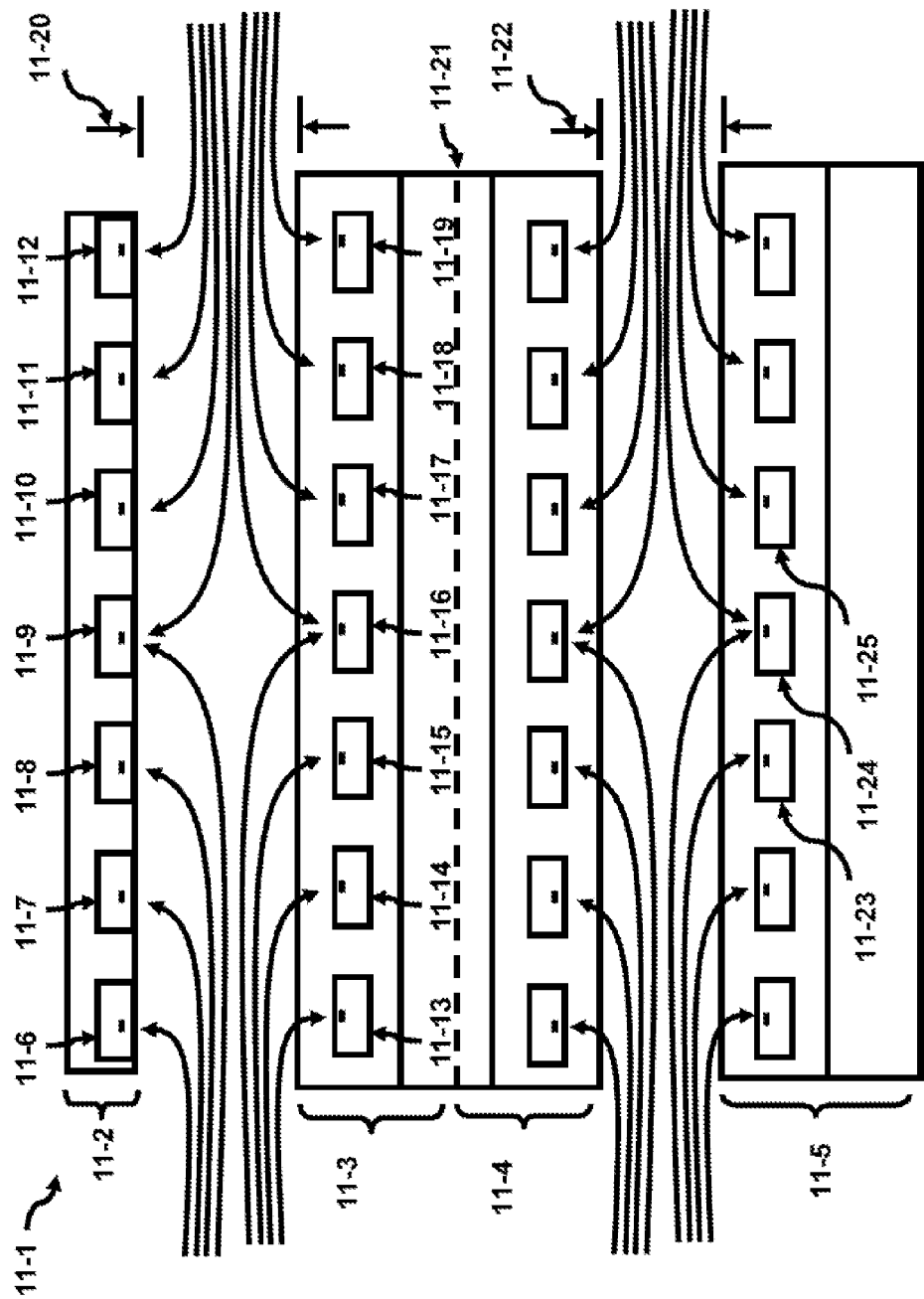
FIG. 11a) illustrates a region bounded by negative charged substrates where a central wafer bonded substrate levitates within the channel region due to the repelling Coulomb force, b) reveals a second central wafer bonded substrate in a channel and c) presents yet a third embodiment of the central wafer bonded substrate in a channel in accordance with the present invention.

The cross section 11-1 illustrated in FIG. 11a illustrates using only repulsive force to maintain a substrate levitated. The system consists of an upper mother substrate 11-2 and a lower mother substrate 11-5 that are firmly held in position. These two substrates can be held in place with respect to each other by being supported inside of a package as will be shown later. The inner daughter substrate consists of two back to back substrates 11-3 and 11-4 that were wafer bonded together along the dotted line 11-21. The Coulomb islands 11-6 through 11-12 in substrate 11-2 having the negative charges repel the Coulomb islands 11-13 through 11-19 in substrate 11-3. In addition, the Coulomb islands in the substrates 114 and 11-5 are negative. Thus, the inner daughter substrate is repelled from the bottom as well. Note in particular that the Coulomb islands 11-23 through 11-25 have a negative charge. The charge of all the Coulomb islands depicted is negative; thus, all forces are repulsive. Since the repulsive charges occur on opposing sides of the combined daughter substrate (11-3 and 11-4), the combined daughter substrate can be held in a levitated position as indicated by the two distances 11-20 and 11-22.

Figure 11B:
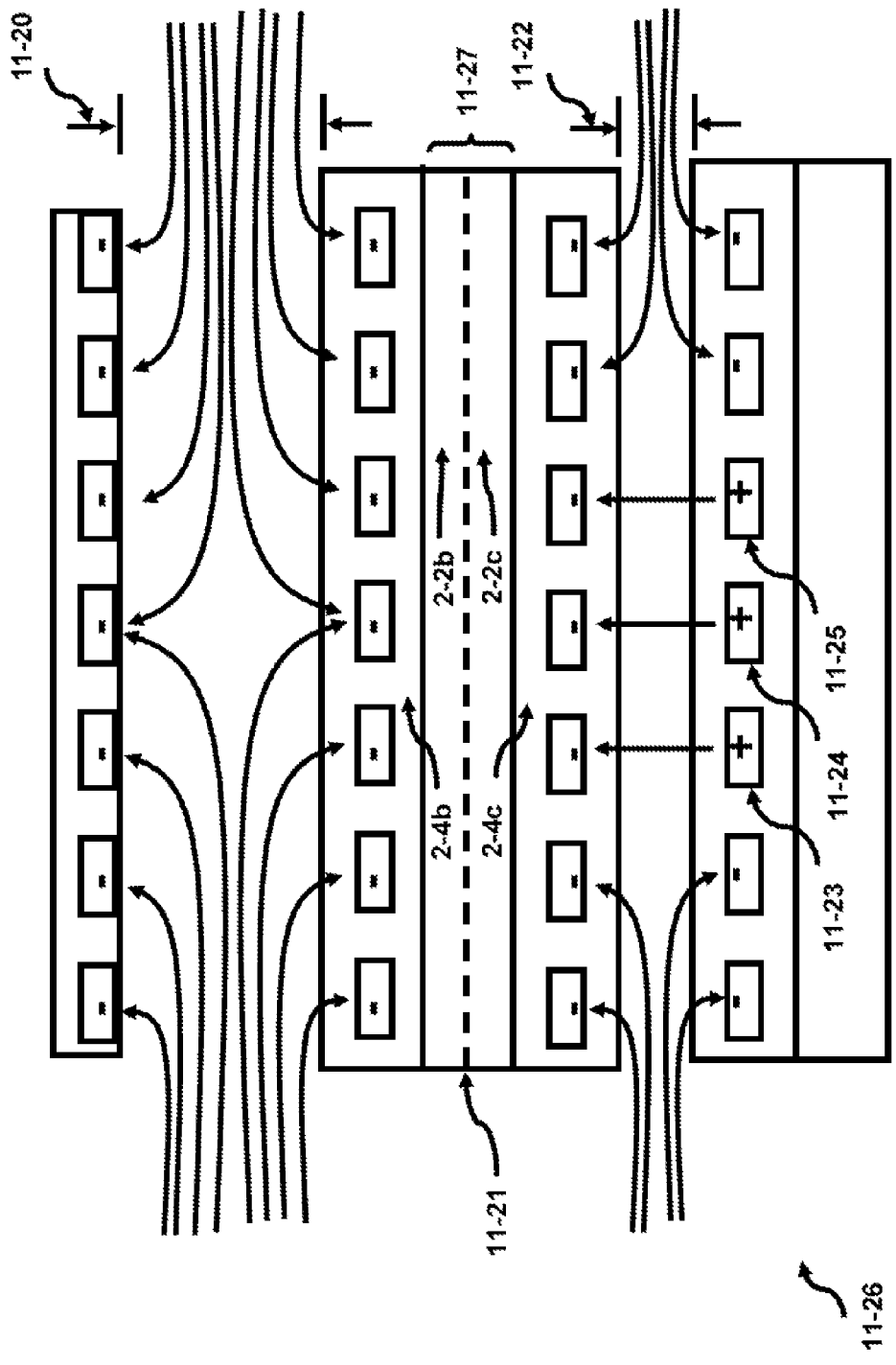

The cross section 11-26 illustrated in FIG. 11b depicts the situation when the Coulomb islands 11-23 through 11-25 are changed to a positive charge. Note that the distance 11-20 increased, while the distance 11-22 decreased due to the attractive force between the positive and negative islands. It would also be possible to decrease the distance 11-22 to zero and allow the combined daughter substrates to make contact with the lower mother substrate 11-5. Note that the region 11-27 contains both foundation portions 2-2b and 2-2c of daughter substrates 11-3 and 114, respectively. The backs can be ground before being wafer bonded to reduce the mass of the combined daughter substrates. A lower mass requires less force to position the daughter substrates and will reduce the charge that is placed on the islands requiring a simpler charging system. The Coulomb islands of the daughter substrates are located in the component portions 24b and 2-4c.

Figure 11C:
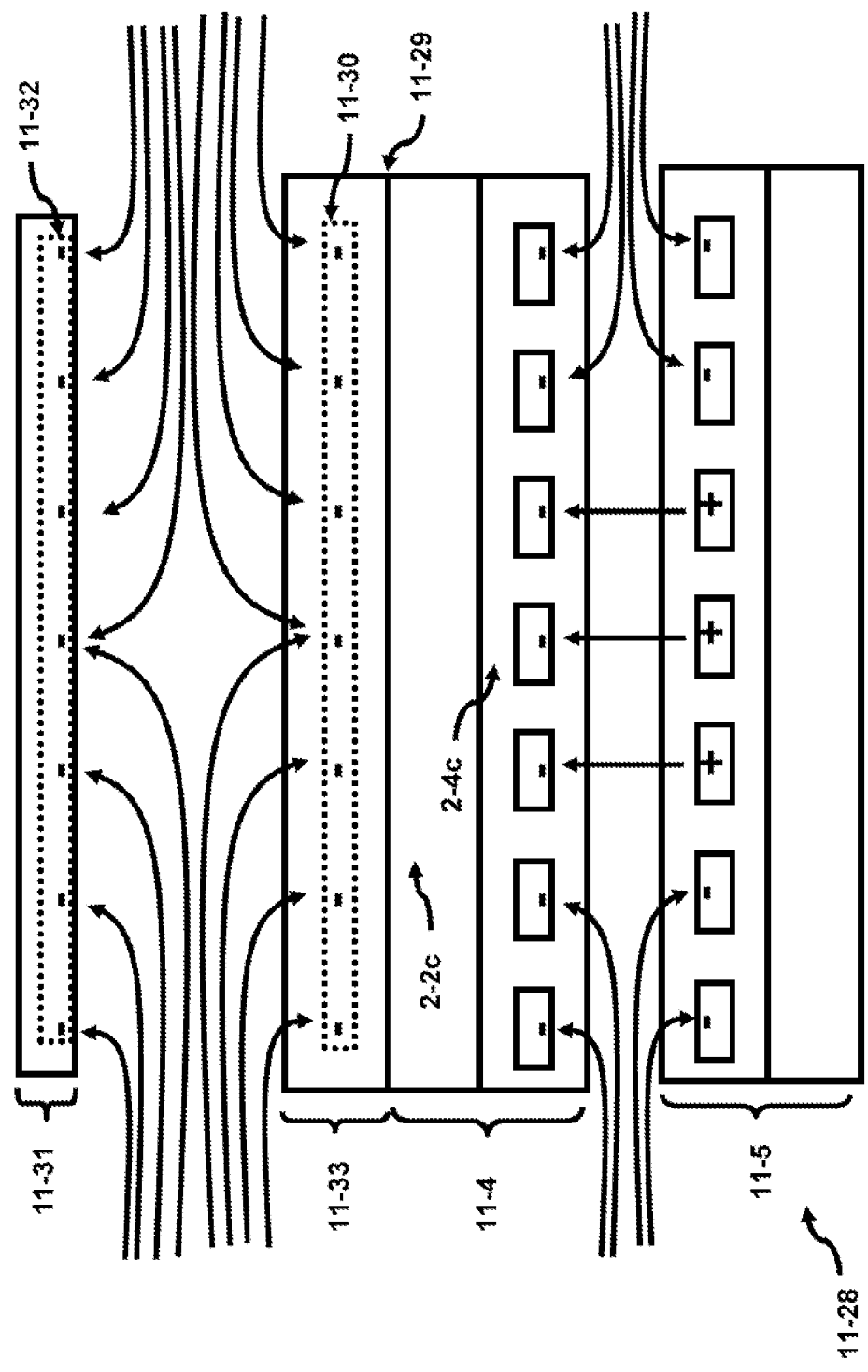

FIG. 11c shows a cross sectional view 11-28 where a third variation of using different substrates are depicted. The tipper mother substrate 11-31 and the upper daughter substrate 11-33 now has a blanket electron implantation generating negatively charged islands 11-30 and 11-32 near the surface of each substrate. The electrons are injected into an oxide layer with a low energy implant such that the charge is close to the surface. The upper daughter substrate can be an oxide and is wafer bonded to the lower daughter substrate 11-4 at the interface 11-29. It is also possible to grow an oxide onto the back side of the 11-4 substrate. In this case, the electrons can be implanted directly into this oxide layer eliminating the need for bonding the upper substrate 11-33 to the lower substrate 11-4. The inner daughter substrate can again be levitated.

FIG. 12 illustrates several possible ways to electrically connect substrates together. In FIG. 12a, the cross sectional view 12-1 shows an upper substrate 12-2 and a lower substrate 12-6, where the Coulomb islands 12-3, 12-5, 12-7 and 12-9 are each charged positive; thus, the substrates repel. Each substrate has a metallic region 12-4 and 12-8 in their component section. These regions can be formed using surface interconnect and via metal segments. In FIG. 12b, as 12-10 depicts, the charge on the Coulomb islands 12-7 and 12-9 have been made negative. Now, the substrates attract and connect to one another along the interface 2-11. The doffed circle 12-12 is the view illustrated in FIG. 12c. Note that the metallic regions have a post within the dotted ellipse 12-13 so that electrical conductive (or heat conduction) path can be formed between the upper and lower metallic segments. The final magnified view 12-13 given in FIG. 12d further highlights the posts 12-15 and 12-14. These posts are metallic and can be formed either by etching back the oxide to expose the highest layer metal, or additional processing steps can be performed to deposit the posts over the metallic regions 12-4 and 12-8. A processing step of wet or dry etching can be used to remove the oxide to expose the metallic traces. If the foundation portion has a non-oxide material, an additional etching step may be required. On the other hand, a deposition technique such as sputtering can be used to add material to the exposed metal surface to create a post.

The Coulomb forces, holding the two substrates together at the posts, can be varied according to a program stored in a control unit that can be located in one or more of the substrates. A sequence can cause the Coulomb force to force a lateral movement (shearing force) of one of the substrates. This will cause the surface of the connected metal posts to rub each other so that any oxide layer formed on the connected surfaces of the posts undergoes abrasion and/or scraping which exposes the underlying metal. An improved metallic connection can then be formed between the two adjoining posts once the underlying metal is exposed. The shearing force can also be used to disconnect the substrates from each other. In addition, a MEMS ultrasonic transducer can be enabled to introduce vibrations to aid the shearing force being applied to the posts.

Figure 12F:
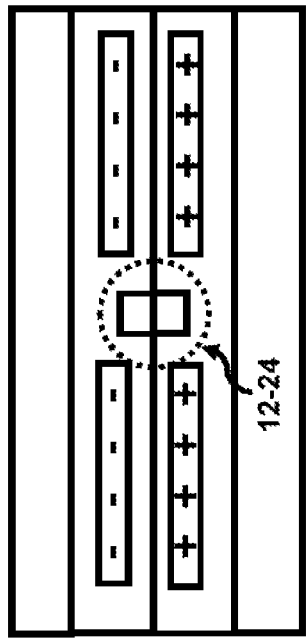
FIG. 12a) depicts two face-to-face positively charged substrates each having posts, b) illustrates the two face-to-face oppositely charged substrates held together by an attractive Coulomb Force, c) reveals a close up of the connected post elements and d) shows yet a further close up of the connected post elements showing the landing areas in accordance with the present invention.
FIG. 12e) depicts two face-to-face positively charged substrates each having a moveable contact post, f) illustrates the two face-to-face oppositely charged substrates held together by an attractive Coulomb force, g) reveals a close up of the un-connected post elements and h) shows a close up of the post elements when connected in accordance with the present invention.
FIG. 12i) presents substrates each having punch-through substrate vias, j) depicts the substrates connected by a solder bump, k) illustrates a close up of the solder bump and l) reveals yet a further close up of the solder bump illustrating the dam structure in accordance with the present invention.
Figure 12H:
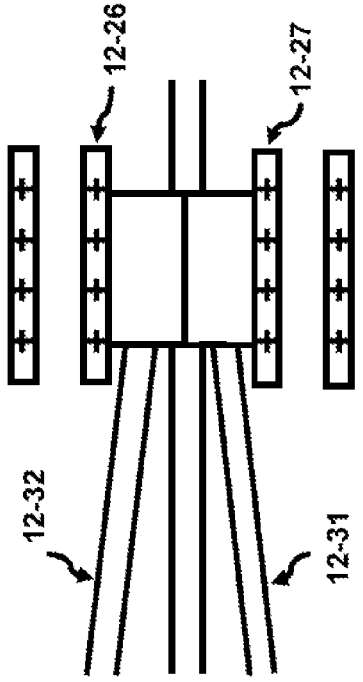
Figure 12E:
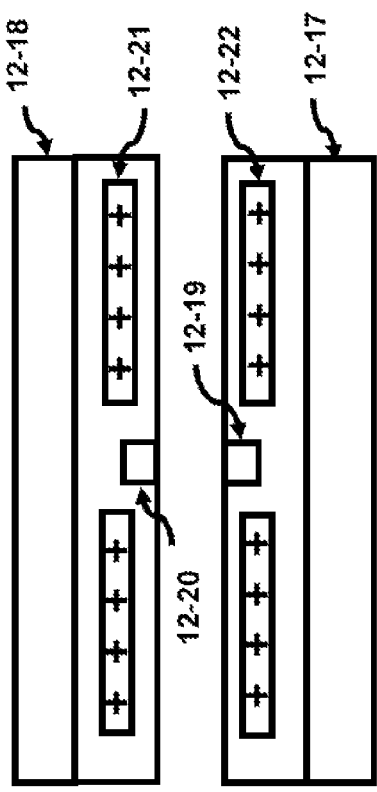
Figure 12G:
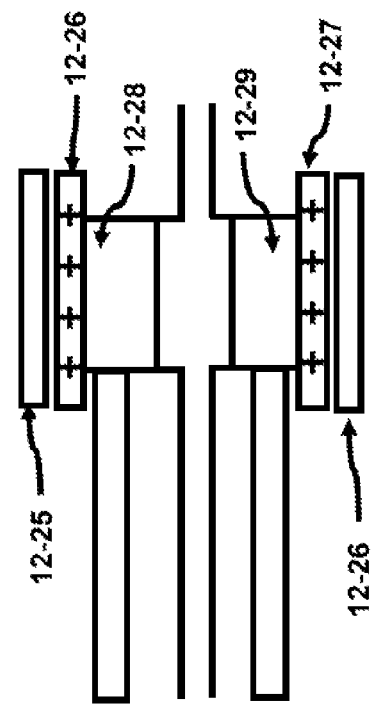

FIG. 12e illustrates another cross section view 2-16 which contains MEMS devices 12-20 and 12-19 in the upper substrate 12-18 and the lower substrate 12-17, respectively. Two of the Coulomb islands 12-21 and 12-22 are shown to be positive. In FIG. 12f, the view 12-23 illustrates the two MEMS devices close to one another within the dotted circle 12-24, since opposing Coulomb islands have opposite charges. The close up view 12-24 in FIG. 12g further illustrates the MEMS device comprising a movable metal shaft 12-28 connected to a positively charged plate 12-26. The shaft can be moved by applying a charge to the juxtaposed Coulomb island 12-25. The lower substrate contains the movable metal shaft 12-29 connected to a positively charged plate 12-27. The shaft can be moved by applying a charge to the juxtaposed Coulomb island 12-26. FIG. 12h applies a positive charge to the islands 12-25 and 12-24 thereby forcing the two movable shafts to approach and connect each other. The cantilevered arms 12-32 and 12-31 connect to the metal shafts and can provide electrical connectivity to the rest of their substrate. Note that the lower MEMS metal shaft can be replaced by the metallic regions mentioned in FIG. 12a having a post allowing the formation of a hybrid connection. The top electrical contact is formed using a MEMS device while the lower contact has an extended post. The travel distance for the MEMS device may need to be increased to achieve an electrical contact.

Figure 12I:
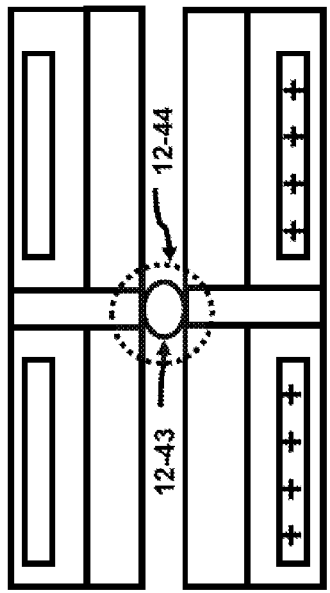
Figure 12J:
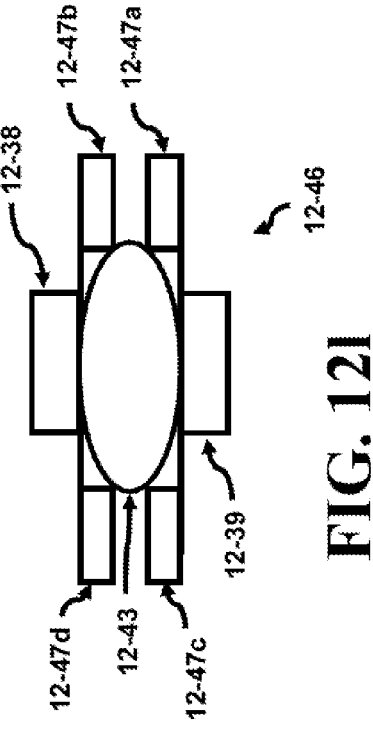
Figure 12L:
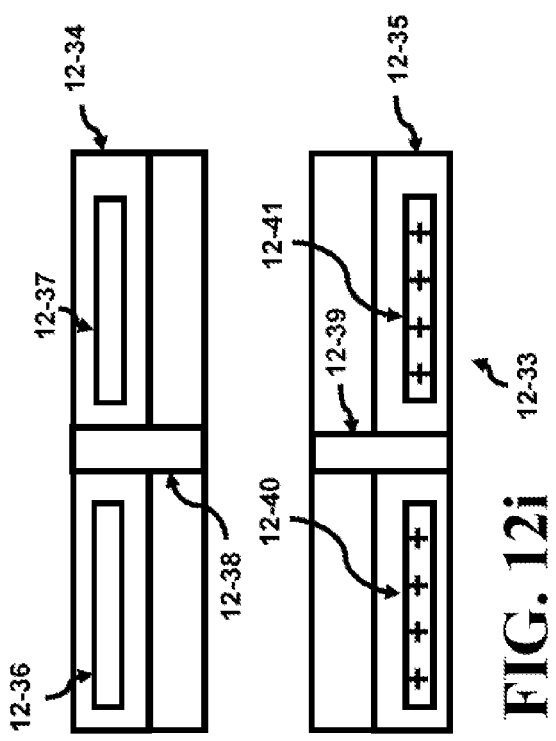
Figure 12K:
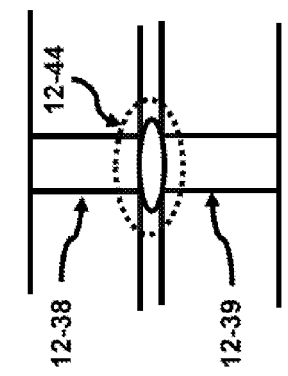

A solder bump connection is also depicted in FIG. 12i. In the view 12-33 two substrates 12-34 and 12-35 are back to back. A metallic through vias through the substrate are illustrated in both substrates 12-38 and 12-39. This forms a metallic conductor between the front and back sides of a substrate. A via can be used to carry electrical power, signals or heat. The Coulomb islands 12-36, 12-37, 12-40 and 12-41 are indicated. However, the force generated by these islands on each other has been reduced since they are on opposing sides of the substrates thereby increasing the distance between them. When solder bumps and through vias are used in substrates, the connection will become more permanent since the solder bump is melted and solidified. FIG. 12j shows the dotted circle 12-44 which identifies the bump 12-43 in the view 12-42. The view 12-45 and 12-46 in FIG. 12k and FIG. 12l indicate the solder bump details. A solder dam formed by 12-47a-12-47d confines the melted solder to remain near the two through vias 12-38 and 12-39 and electrically connect the vias together.

Of course, vias that penetrate the entire substrate can be used in the first two examples. In addition, for the solder bump case, the substrates could also be arranged top to back as well.

A cross sectional view 13-1 of a packaged levitating device is illustrated in FIG. 13a. The top 13-2 of the package can hold a substrate having an electron charge 13-3 embedded near the surface. The base 13-7 of the package mounts the substrate 13-6 while two substrates 13-5 and 13-8 are shown levitating between the two mother substrates 13-2 and 13-6. The top substrate of the daughter substrates are illustrated with an electron implanted island 13-4. All island charges are negative and adjusted in magnitude; thus, the daughter substrates are in a levitated position. Connecting the package to the substrate 13-6 can be done using solder bumps, through substrate vias, or bonding wires. Finally, solder balls 13-7a form the electrical, heat and mechanical connection between the substrates and the PWB board.

In the view 13-9 given in FIG. 13b, the set of coulomb islands 13-11, 13-12 and 13-13 help to levitate the daughter substrates as mentioned earlier. However, RF energy 13-10 is applied to the daughter substrates so that they can receive external power when in the levitation state. For low power applications, the heat dissipation generated within the daughter substrates may not be an issue and the heat may be radiated to the inside walls of the package; however, as the power dissipation within the daughter substrates increases other means may be required to eliminate heat from the substrates.

FIG. 14a illustrates a package 14-1 that contains an adjustable capacitor formed between two substrates. The top of the package 14-2 does not contain any islands. The daughter substrate 14-6 is levitated using both like (14-7 and 14-12) and opposing (14-8 and 14-13) charged islands. Similar conditions hold for the remaining islands. The first repels while the second attracts; if the force can be balanced then the substrate 14-6 can be held in a levitated state. The distance of separation 14-3 is indicated. In addition, a bonding wire is shown to connect an I/O pad to the package pad.

The capacitor consists of parallel metallic plates 14-9, 14-14 and 14-15. The metallic plate 14-9 located in the daughter substrate has a larger area and overlaps the areas of the metal plates 14-14 and 14-15 which are located in the mother substrate 14-4. A signal can be applied to the plate 14-14 then capacitively coupled to the plate 14-9. This signal then returns capacitively to the lower plate 14-15. Thus, this path consists of two capacitors in series and the value of these capacitors depends on the distance of separation 14-3. Such a capacitor can be used to measure the distance using electrical circuit techniques. For example, a capacitive bridge circuit can be formed using the series capacitors as one of the bridge elements. By measuring the output of the comparator connected to the bridge circuit, the relative change in distance can be measured. Furthermore, the plate 14-9 can be tapped electrically and either extract the signal at this point on the substance 14-6 or inject a signal into the plate. This capacitor exists when the daughter is in contact with or being levitated above the substrate. As the daughter substrate moves away from the mother substrate the capacitance would decrease in magnitude.

Another possible use for these capacitors is to create an adjustable LC tank circuit 14-16. Such a circuit is illustrated in FIG. 14b. The numerical identifiers are the same as in FIG. 14a except that their circuit equivalents are given. One lead of the inductor 14-17 is connected to the lower plate 14-14, while the second lead of the inductor is connected to the lower plate 14-15. The metallic plate 14-9 completes the LC circuit. Furthermore, the capacitors are adjustable by altering the distance of separation 14-3 using the Coulomb force. Note that the dotted lines show the surfaces of the two juxtaposed substrates. As the distance is modified, the frequency of operation of the tank circuit is altered. The regenerative circuit is not illustrated to simplify the diagram. (See for example US app 20070018739).

Another use is to measure the frequency of operation of the tank circuit 14-16, use a lookup table, match the measured frequency to an entry in the table, and extract the value of the distance of separation. Such a circuit can be used to measure this distance and be used to apply corrective adjustments to the Coulomb islands so that the separation is controlled. This is another way of measuring the separation so that the daughter substrate can be maintained in a controlled state of levitation.

In the package 14-18 of FIG. 14c, similar numbered items as previously discussed are the same. Two new plates 14-20 and 14-21 are illustrated in the substrate 14-19. Each of these plates overlaps the plates 14-14 and 14-15 on the lower substrate 14-4, respectively. Each pair of plates 14-20 with 14-14 and 14-21 with 14-15 creates two capacitors. These capacitors can be used individually or as a balance pair. For example, FIG. 14*d* illustrates a balanced interface circuit 14-22. The block 14-24 can be a balanced I/O driver which applies two signals out of phase with each other to the lower plates 14-14 and 14-15. These signals are then capacitively coupled to the upper plates 14-20 and 14-19 and then applied to a balanced receiver 14-23 (For example, see U.S. Pat. No. 5,708,389). As the distance of separation 14-3 changes, the transfer of data from the lower substrate 14-4 to the upper substrate 14-19 is being captured using digital signals. Because of the larger noise margin of digital signals compared to analog signals, varying the amplitude of the received digital signal within a specified range may not effect the interpretation of the signal. Thus, the digital signals can be captured and used to provide control, movement, adjustment and identification commands to the upper substrate while the daughter substrate is in the levitation position. Similar circuits can be used to transfer data from the upper to lower substrates.

FIG. 15*a* illustrates a cross sectional view 15-1 of a package where the daughter substrate 15-2 contains an inductor 15-4. If the foundation portion is composed of any low resistivity material (e.g., p+-epi, highly doped materials, metallic structures, etc.), the substrate can be preferably etched to remove this section as indicated by the cut 15-5. In SOI (Silicon On Insulator), the loss is less severe since the foundation portion is an oxide. The removal of this material decreases the losses of the inductor and improves the "Q" of the inductor. The daughter substrate is separated by the distance 14-3. The volume around the inductor 15-4 is air which would reduce the eddy current loss in the substrate that is typically associated with this volume (for example see U.S. Pat. No. 7,250,826 and U.S. Appl. 2007018739). The self-eddy current loss occurring within the inductor itself can be decreased in one example as indicated in U.S. Appl. 20070176704. As before, a bonding wire 14-11 (only one is shown) is used to connect the I/O pads of the mother substrate 15-3 to the a bonding pad of the package. A top view 15-4*a* of one type of inductor layout is illustrates in FIG. 15*b*. The leads of the inductor are 15-6 and 15-7 and the inductor is typically fabricated from a metallic sheet. Finally, the electrical symbol 15-4*b* for the inductor without parasitics is depicted in FIG. 15*c*. Although the cut is used to remove conductive material from regions around the region perpendicular to the coil's plane, the cut can also be used preferentially to remove conductive material from regions perpendicular to the Coulomb island's surface to improve the operation of the Coulomb island.

Figure 16A:
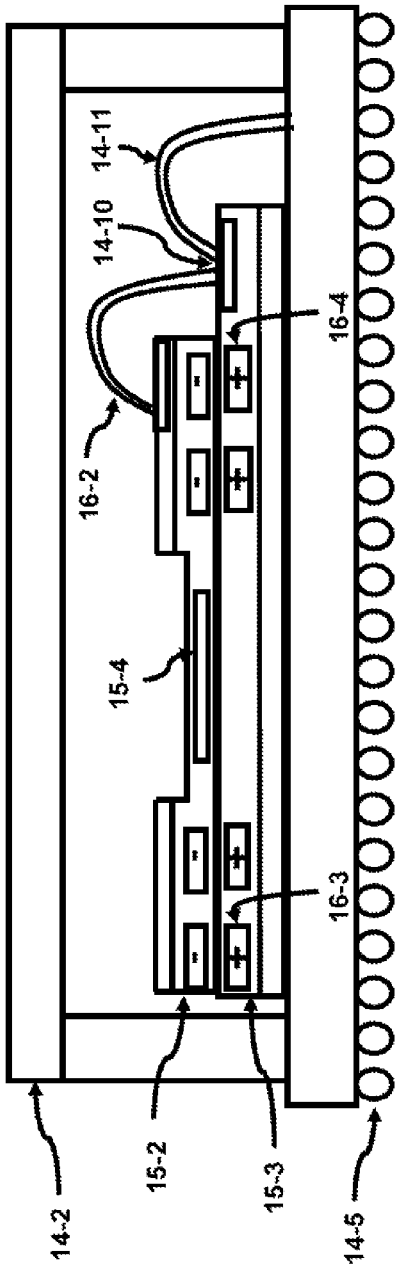
FIG. 16 reveals a packaged system incorporating a) a Coulomb force device that contains an inductor and is wire bonded to the lower substrate and b) a levitating Coulomb force device which is attached to the bond wire providing an electrical connection to the tipper substrate in accordance with the present invention.

In FIG. 16*a* the cross sectional view 16-1 shows a daughter substrate 15-2 being held to the mother substrate 15-3 by Coulomb forces. However, just before these two substrates made contact due to the Coulomb force, the substrates, while existing in a wafer form were tested at the wafer level. During this test, Coulomb islands were probed and charged to a given magnitude and polarity. The wafers containing the daughter substrates were sawn apart and cleaned in a non-conducting environment so that the probe points do not offer a discharge path. Then, the daughter substrates can be positioned on the wafer using a pick and place tool. Once the daughter substrate comes close to the mother substrate, the pick and place tool can release the daughter substrate. The electrostatic forces will help snap the daughter substrates into position while making physical and electrical contact with the mother substrate in wafer form. Different daughter substrates can have different patterns of Coulomb islands enabled. This offers a "key" to only allow those daughters with a matching charge pattern to "fit" the mother substrate at these points. Otherwise, the daughter substrate is not connected. The physical contact is mechanical in nature in that the portions of the surfaces are in contact to one another and heat flow can occur between the substrates. The electrical contact is allowing electrical signals (power, signals or both) to flow between the two juxtaposed substrates. The mating surfaces of the substrates are planar since CMP (Chemical-Mechanical Planarization) is used to maintain a flat surface. Once all of the daughter substrates are placed on the wafer containing the mother substrate, the wafer can then be cut. Note that the daughter substrates are physically in contact with the mother substrate; therefore, contaminants will have a difficult time entering the mating interface formed between the surfaces of the daughter and mother substrates. Once the mated substrates are packaged, they can then be wire bonded to transfer signals and power. Another option is to assemble the daughter substrates after cutting the mother substrate from the wafer. Another of connecting the substrates to each other and to the package includes the use of solder bumping.

Figure 16B:
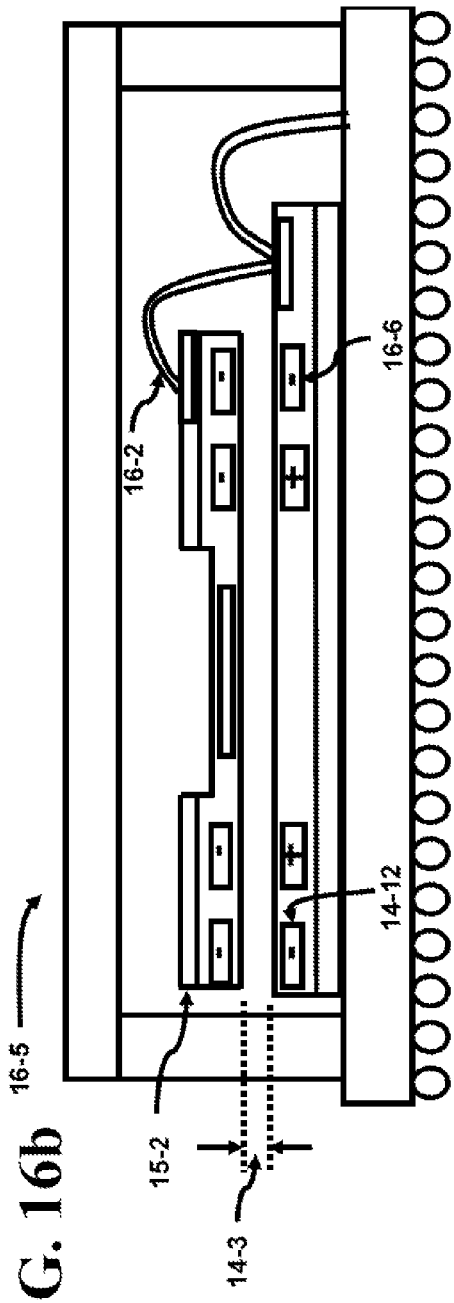

One example of wire bonding is illustrated in FIG. 16*a*. A bonding wire 162 makes contact between an I/O pad of a daughter substrate 15-2 and the mother substrate 15-3 at the I/O pad 14-10. A second bonding wire 14-11 is formed between the I/O pad 14-10 and the package pad. Such a structure would be used to provide power to the daughter substrate. Other possibilities include wire bonding the daughter substrate directly to the package pad. The inductor 15-4 is close to the surface of the mother substrate 15-3. FIG. 16*b* illustrates the use of repelling Coulomb forces to lift the daughter substrate 15-2 while still being tethered by the bonding wire 16-2 to the I/O pad 14-10. The inductor 15-4 is now surrounded by air increasing its Q. In addition, power, signal or both leads can be attached to the levitated substrate. The bonding wires tethered the levitating substrates which can hold oscillators, lasers and other circuits. These wires can help conduct heat as well.

The way the daughter substrate is moved across the surface is provided in the following figures. A 2-D representation will be used to describe the basic concepts of lifting, moving, and dropping while a 2-D with perspective will be used to give a better understanding by visualizing how the substrates slide over the mother substrate. The Coulomb islands are shown to be in a regular or arrayed pattern; however, this is not a requirement. For instance, instead of covering the entire substrate with an array of islands, strips of islands can be formed that bear a relationship to the size of the daughter substrates (either directly or in multiples). Doing so would free up the remaining area for signal, clock and power bussing.

One example of strips of islands is given in FIG. 17*a* with the cross sectional view 17-1. Shown is a mother substrate 17-3 with a daughter substrate 17-2 that are Coulomb attached to each other by the charges on the islands 17-4, 17-5, 17-7 and 17-10. The remaining islands 17-6, 17-8, 17-9, 17-11 and 17-12 are all located in the substrate 17-3. Note that the upper substrate 17-2 does not have matching islands at the locations opposite the islands 17-8 and 17-9. The elimination of these islands allows for an easier explanation but is not an indication that their absence is the only way to build these systems. The locations of the islands are left flexible to allow for a variety of possible island placements for a given application since these needs for a different application may require a different island placement. In addition, the shape of the Coulomb islands was introduced as being circular; however, the islands can be oval, rectangular, or any geometrical shape. In addition, an island will be introduced that has its surface perpendicular to the top surface of the mother substrate. Note the marker 17-13 which indicates the initial location of the right edge of the substrate 17-2. Finally, the drawings are not necessarily drawn to scale as pointed out earlier.

Figures 17C, 17D:
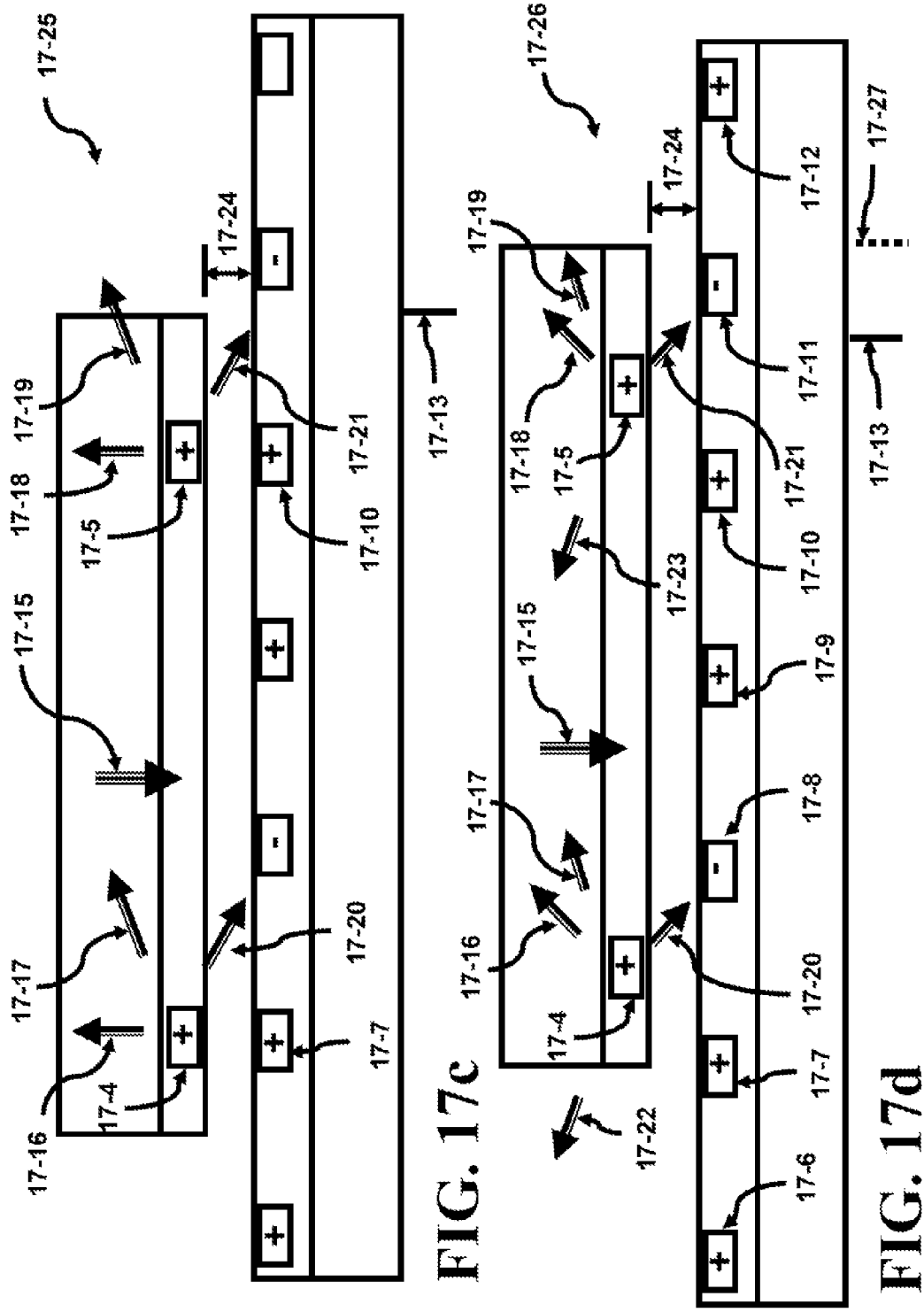
FIG. 17c) illustrates the first post-stage charging of islands and their unit vector forces to move the top substrate upward and d) illustrates the first post-stage charging of islands and their unit vector forces as the top substrate moves right in the direction of minimum energy in accordance with the present invention.

FIG. 17b illustrates the view 17-14 where the islands 17-8 and 17-9 have been given a charge. The right edge of the daughter substrate is marked by the line 17-13 and the substrates are still in contact. The substrate 17-2 has a gravitational force 17-15 and the unit vector forces 17-16 through 17-21 are indicated. The magnitude of these forces are not shown but can be determined by knowing the size of the islands, their distances, and their charges. Equ. 2 can be used to estimate the unit vector forces and components. The forces 17-16 and 17-18 are downward since each pair of Coulomb islands: 17-4 and 17-7, 17-5 and 17-10 have an attractive force and hold the two substrates together. The forces 17-17 and 17-19 are repulsive and are due to the two pairs of same charged islands: 17-6 and 17-4, 17-9 and 17-5. In addition, the forces 17-20 and 17-21 are attractive and are due to the two pairs of oppositely charged islands: 17-4 and 17-8, 17-5 and 17-11. Note that the summation of the unit force vectors indicate that there will be a net force in the positive x-direction FIG. 17c illustrated the cross sectional view 17-25 where the islands 17-7 and 17-10 flip their charge from a negative to a positive value. The vector 17-16 and 17-18 have changed direction by 180°. The positive y-component forces of the Coulomb forces should add up to be greater than the gravitational force 17-15 in magnitude. An extra force may be needed to overcome the stiction forces between the two substrates. Stiction is a force where the surfaces that are in contact develop an attractive force due to Van der Wall forces for example and an additional force in the y-direction may be needed to overpower this force. In addition, an x-direction force can apply shear force between the two substrates. Once the daughter substrate disconnects, it moves upwards as shown by the displacement 17-24. The daughter substrate also slides in the positive x direction as shown in FIG. 17d since this is in the direction of minimum energy. As the daughter substrate moves in the positive x-direction, the distance between the similarly charged pairs of islands (174 and 17-9; 17-5 and 17-12) decreases such that the repelling force increases in magnitude. This acts as a stop for the daughter substrate. The net movement of the daughter substrate in the positive x-direction is indicated by the dotted line 17-27.

Figure 17E:
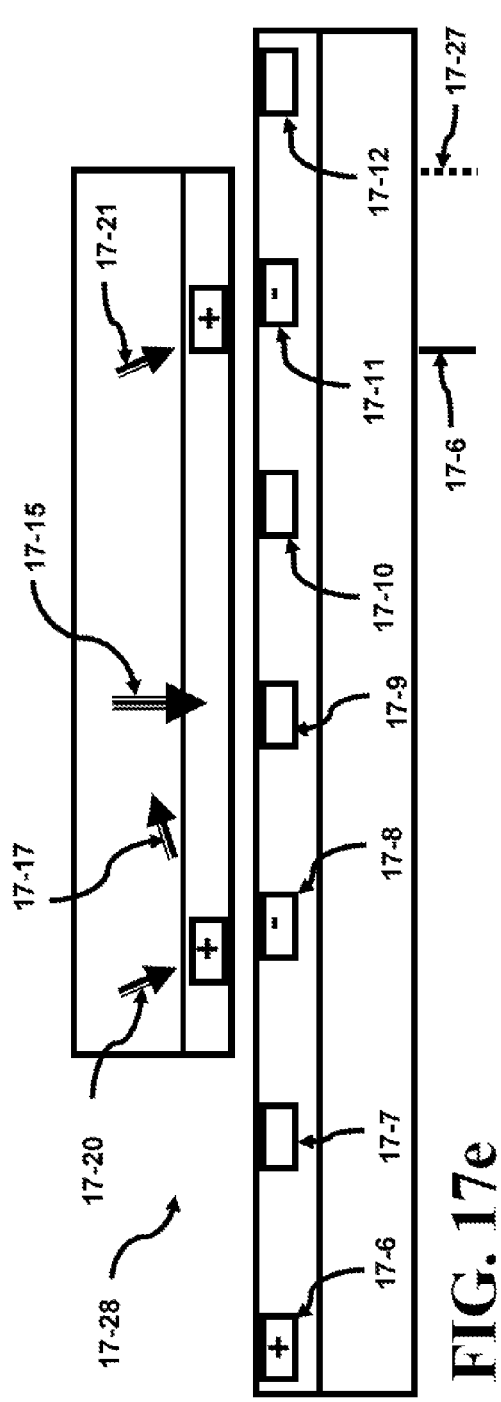
FIG. 17e reveals the second post-stage charging of islands and their unit vector forces to move the top substrate further to the right, f) shows the third post-stage charging of islands and their unit vector forces to position the top substrate to contact the mother substrate and g) presents the timing waveforms of the charges applied to the islands in accordance with the present invention.
Figure 17F:
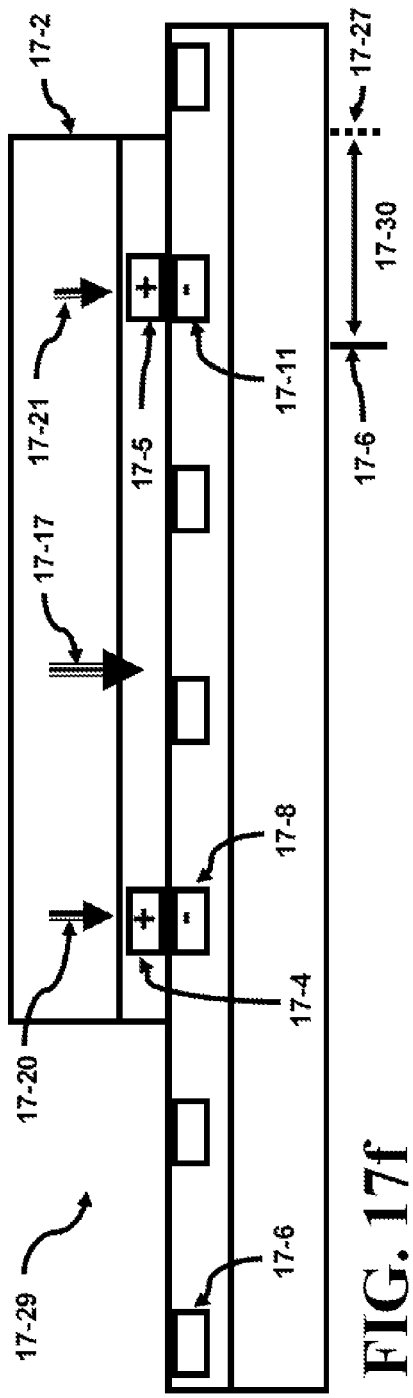
FIG. 17a) presents Coulomb islands that are oppositely charged on two juxtaposed substrates causing them to be held together by an attractive Coulomb force and b) depicts the pre-stage charging of islands and their unit vector forces in preparation for moving the top substrate in accordance with the present invention.

FIG. 17e shows the charge on the islands 17-7, 17-9, 17-10 and 17-12 being neutralized. The only forces are the attractive forces 17-20 and 17-21 and the repelling force 17-17. These forces continue moving the substrate in the x-direction and prepare the positioning of the daughter substrate over the mother substrate. Finally, the cross section view 17-29 in FIG. 17f depicts the daughter substrate in the new position and being displaced by the distance 17-30. The system is ready to repeat the same movement or introduce a movement into or out of the page. There are many ways to perform the charging operation of the islands to control the movement of the daughter substrates. It is easy to see that the charge on island 17-7 could have been positive in FIG. 17e and still provide the same net result. Another aspect is that the description of movement indicates a lift, move, and drop sequence. This is not always required. For instance, suppose the daughter was to slide over several islands, then the movement should be lift and move over all islands, then drop to place the daughter substrate into position.

Figure 17G:
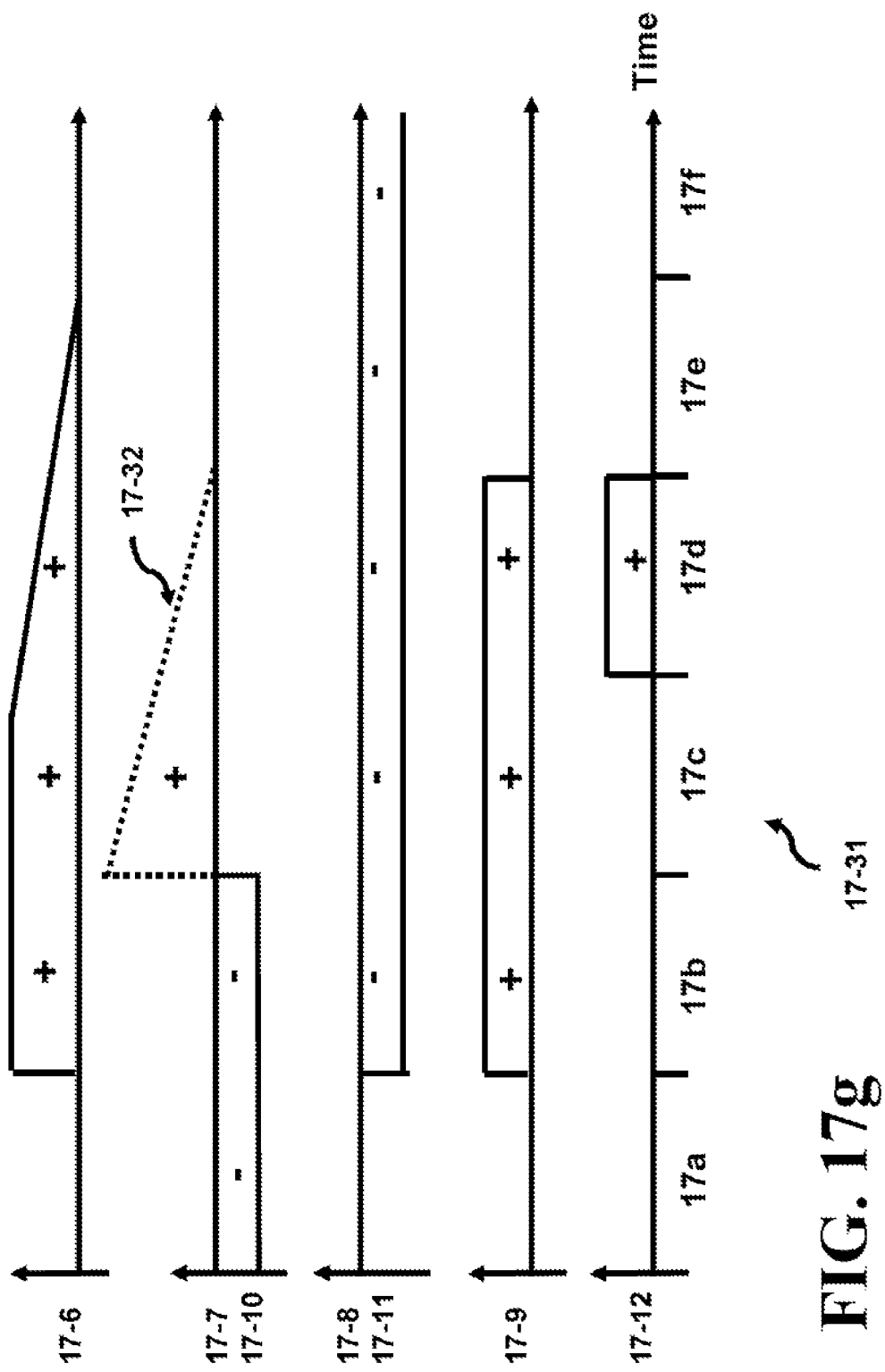

The timing diagrams 17-31 to make the daughter substrate move in the positive x-direction are given in FIG. 17g. The magnitudes of the charge distribution in each island are not drawn to scale. Note that the magnitudes can also vary linearly 17-32 as a function of time. The set of waveforms shown are one possible combination to move the substrate in the positive x-direction but others are possible. The y-axis provides the potentials of several Coulomb islands and how these potentials vary over the x-axis that is segmented according to the figures. Note that the positive charge of the coulomb islands 17-4 and 17-5 located in the daughter substrate remained constant. In this case, the power dissipation of the daughter substrate can be reduced to a very low value. The next step is to move a substrate vertically against gravity; this issue is covered in the next set of figures.

Figure 18B:
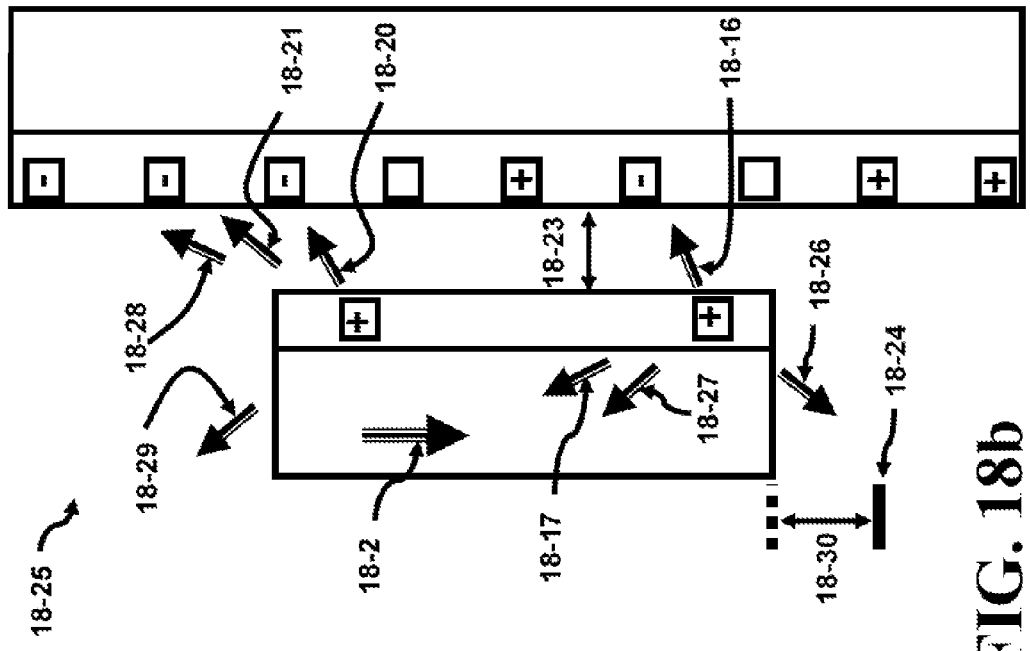
FIG. 18a) depicts the post-stage charging of islands and their unit vector forces to move the levitating substrate vertically and b) illustrates a second post-stage charging of islands and their unit vector forces to move the levitating substrate vertically in accordance with the present invention.
Figure 18A:
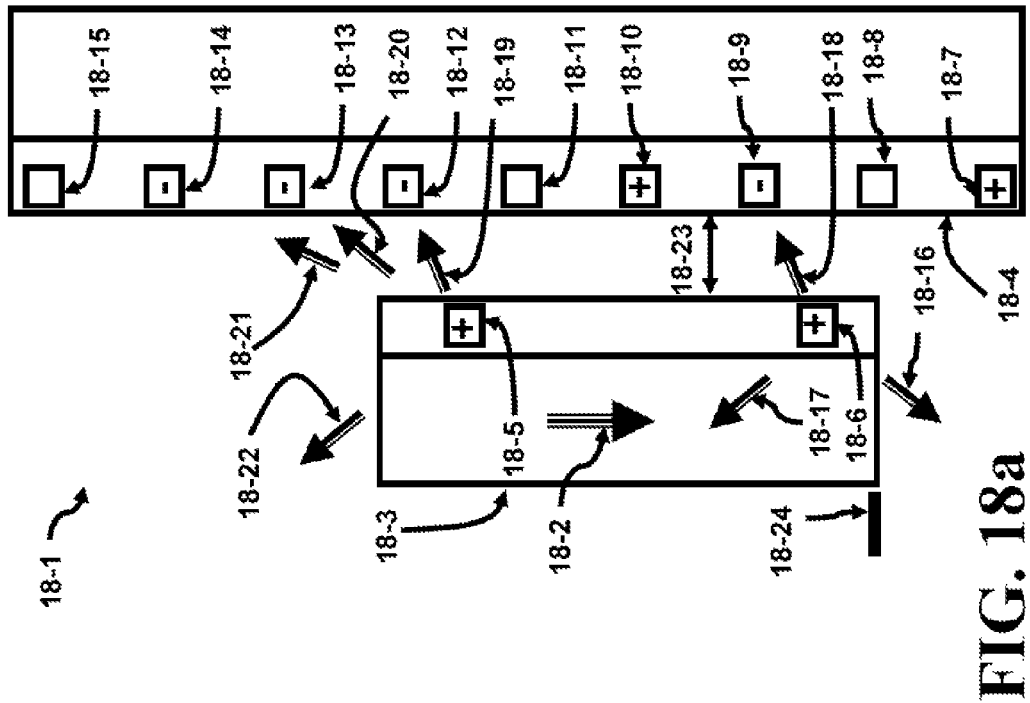

FIG. 18a illustrates the cross sectional view 18-1 of the case when the daughter substrate 18-3 is moving in the positive y-direction against gravity 18-2. One can appreciate that wafer thinning (such as back grinding) is very beneficial to ease the movement of the daughter substrates since their mass can be reduced. This reduction in mass also can reduce the magnitude of the required voltages necessary to activate the forces associated with the coulomb islands. Thus, the power dissipation of the system can be reduced if the daughter substrates are thinned to reduce their mass, In the example given, the mother substrate 184 generates the forces necessary to move the daughter substrate 18-3 against the force of gravity 18-2. Although there are only two Coulomb islands, 18-5 and 18-6, on the daughter substrate 18-3, the additional placement of islands would offer a benefit in that the movement becomes performed in smaller movements and thereby providing better control. However, only two islands will be used in this description. The mother substrate 18-4 has the Coulomb islands 18-7 through 18-15. The islands 18-7 and 18-10 are positively charged. The island 18-7 generates a repulsive force 18-17, while the island 18-10 generates the repulsive forces 18-16 and 18-22. The arrows indicate the unit vector components of the force. The magnitudes of these forces are not shown. The islands 18-9 and 18-12 through 18-14 are negatively charged. They generate the attractive forces 18-18, and 18-19 through 18-21, respectively. The summation of all the positive y-component forces must exceed the force of gravity 18-2. Also there should be a negative x-component of force that overcomes the stiction force and displaces the substrate by the distance 18-23. Once the substrate moves upwards a vertical distance 18-30, FIG. 18b shows the cross sectional view 18-25 and the charged islands 18-8 and 18-11 that changed their charge from neutral to a positive charge, the islands 18-9 and 18-12 were negative and were changed to a neutral charge, the island 18-10 which altered the polarity of charge from positive to negative, and the island 18-15 which went from neutral to a negative charge. The diagram indicates that the direction of the force 18-16 flipped in direction to help the substrate move vertically. Force 18-17 is still there but has a smaller magnitude since the distance between the two charges increased. Forces 18-20 and 18-21 increase in magnitude to help move the substrate vertically since the distance between these respective islands decrease. The components of the forces 18-26, 18-27 and 18-29.help to move the substrate in the negative x-direction, while other components of the forces 18-27 through 18-29 help to compensate for the force of gravity 18-2. The net movement of the substrate shows a vertical displacement 18-30 equal to the "distance between the islands" on the mother substrate. Observing the pattern of the charged islands on the mother substrate and their relative placement to the daughter substrate in FIG. 18b illustrates that the pattern is similar to that shown in FIG. 18a except the daughter substrate has been shifted one "island distance" upwards. Thus, to continue the movement upwards, the same procedure is repeated over and over again. The control unit identifies the daughter substrate, the direction of movement, the direction of gravity and issues appropriate commands to generate the necessary charges applied to the Coulomb islands to perform the movement.

Figure 19B:
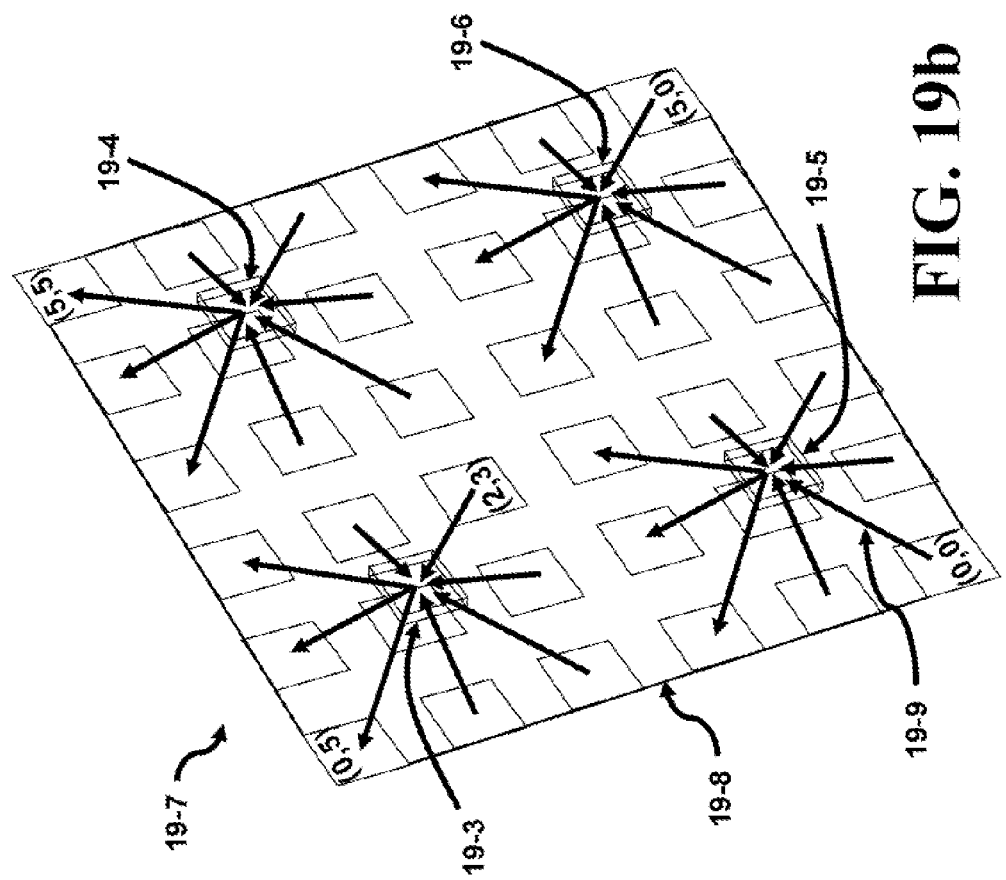
FIG. 19) reveals a 3-D substrate containing 4 Coulomb islands and b) shows the 3-D substrate containing the 4 Coulomb islands (structural outline hidden) superimposed over the mother substrate indicating the unit vectors of force applied to the 4 Coulomb islands in accordance with the present invention.
Figure 19A:
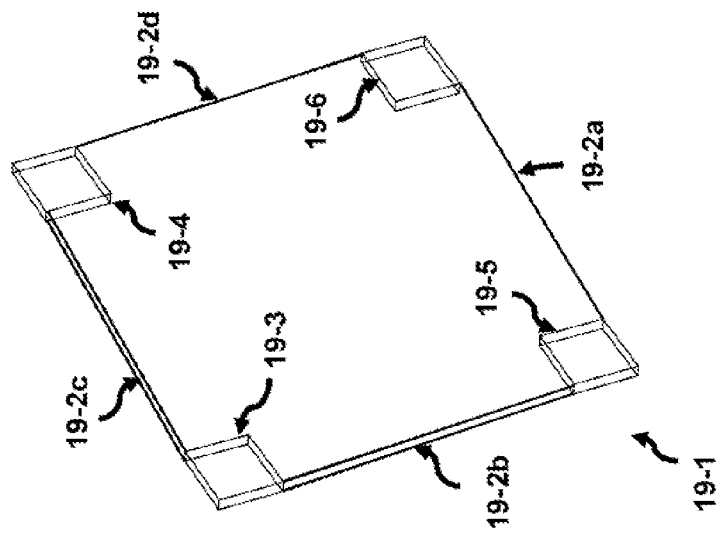

A simplified version of a daughter substrate 19-1 is illustrated in FIG. 19*a*. The sides of the daughter substrate are 19-2*a* through 19-2*d*. At the corners of the substrate are coulomb islands 19-3 through 19-6. A 2-D view with depth perspective 19-7 is depicted in FIG. 19*b*. The daughter substrates is placed over the mother substrate 19-8 and the sides of the daughter substrate (19-2*a* through 19-2*d*) are made transparent so that only the coulomb islands 19-3, 19-4, 19-5 and 19-6 are visible. The mother substrate has an array of islands located at Cartesian coordinates. The lower left shows the (0, 0) coordinate, while the (5, 5) location corresponds to the island in the upper right corner. The daughter substrate is placed over the array of the mother substrate such that the island 19-3 is over the island at (1, 4), 19-4 is over the island at (4, 4), 19-5 is over the island at (1, 1) and 19-6 is over the island at (4, 1).

A minimum energy surface is made by applying potentials in certain sequences to the Coulomb islands. Suppose the daughter substrate is to move in the positive y-direction, then the energy surface surrounding each of the islands on the daughter substrate need to have a minimum energy barrier in the positive y-direction and a larger energy barrier in the three directions of negative y-direction, positive x-direction and negative x-direction. Assume that the islands of the daughter substrate are charged positively. In addition, the islands directly under these islands on the mother substrate (1, 4), (4, 4), (1, 1) and (4, 1) are also charged positively. Thus the daughter is repelled from the surface of the mother substrate. A unit force vector would point from the island of the mother substrate to the juxtaposed island of the daughter substrate (but is not shown). The remaining unit force vectors on the island 19-3 due to the adjacent islands are indicated. Whatever is done in the vicinity of one of the islands of the daughter substrate on the mother substrate is repeated at the other three islands as well; thus, the formation of the minimum energy surface can be made for one of the daughter islands which can then be repeated at the three other islands. The island at (1, 1) is used as the example. The next step is to place a positive charge at the islands forming a semi-circle shape surrounding the island located at (1, 1). These include the islands located at the coordinates (0, 1), (0, 0), (1, 0), (2, 0) and (2, 1). The forces that the island 19-5 would experience are indicated by the direction of the corresponding unit vector forces. In other words, as an example, the force 19-9 on the island 19-5 is shown to exist from the island at (0, 0) of the mother substrate to the island at 19-5 of the daughter substrate. Thus, the semi-circle formed earlier acts as a barrier to prevent the island 19-5 from moving in the negative y-direction and either of the positive or negative x-directions. Thus, this energy barrier is not at a minimum in these directions. However, in the positive y-direction the barrier is less if the charge of the islands at (0, 2), (1, 2) and (2, 2) are set to a neutral charge. To enhance the reduction of the barrier further, the islands at (0, 2), (1, 2) and (2, 2) can be set to have a negative charge. Now, a force exists to move the island 19-5 in the positive y-direction. Thus, a minimum energy barrier in the positive y-direction was created around the island 19-5 of the daughter substrate 19-1. These forces allow the island 19-5 to be levitated and slide in the positive y-direction. By symmetry, each of the remaining islands of the daughter substrate have a similar energy barrier allowing the entire daughter substrate 19-1 to be easily moved in the positive y-direction. The net force required would be evenly divided between the four islands of the daughter substrate. Each island only has to generate ¼ of the overall force. This can reduce the voltage necessary to charge the islands and can reduce the power dissipation of the system.

Figure 20B:
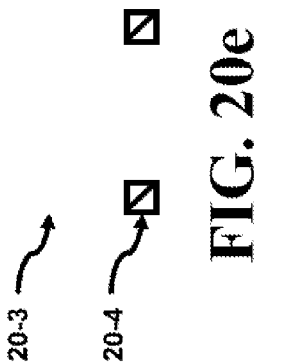
FIG. 20a) presents single symbols indicating the condition of the charge of the islands, b) depicts the combined symbols created by overlapping the single symbols and c) illustrates several cases of overlapping the single symbols to form the combined symbols in accordance with the present invention.
FIG. 20d) reveals the 2-D surface view of the mother substrate containing a matrix of islands where the islands located at (2, 1), (5, 1), (2, 4) and (5, 4) are charged positive and e) shows the 2-D structural view of the daughter substrate containing the 4 Coulomb islands which are negatively charged in accordance with the present invention.
Figures 20A, 20C, 20D, 20E:
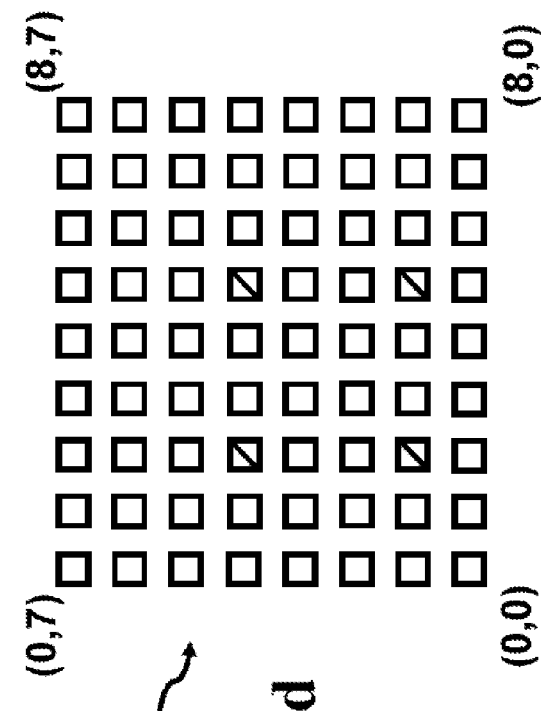

To help explain the next figure, some symbols need to be introduced. FIG. 20*a* a single island symbol where the island can be neutral, positive or negative. FIG. 20*b* illustrates the final symbol when two islands are superimposed on each other. For example, the top row shows a negative island being placed over a negative island, the arrow points to the final symbol. The next row places a positive island over a positive island generating the final symbol on the right. The third row shows a neutral island placed over a positive island which generates a positive symbol. The fifth row shows a positive island being placed over a negative island; the symbol generated is a crossed box. FIG. 20*c* illustrates those symbols which generate forces between the two islands forming the symbol. The symbols in the first two rows experience a repulsion force between the two juxtaposed islands while the symbol in the third row experiences an attractive force between the two juxtaposed islands.

FIG. 20*d* illustrates the placement of the coulomb islands in the mother substrate 20-1. The islands at (2, 1), (5, 1), (5, 4) and (2, 4) are charged positively as indicated by the symbol. A daughter substrate 20-2 is shown in FIG. 20*e* with sides 20-3 and Coulomb islands 20-4 at the corners of the substrate. The daughter substrate has negatively charged islands.

The process of moving the daughter substrate in the y-direction which was shown earlier is repeated in FIG. 21 to illustrate how these symbols can be used to modify the energy barrier to impose a linear movement on the daughter substrate. The system 22-1 in FIG. 21*a* illustrates the placement of the daughter substrate 20-3 over the mother substrate 20-1 introduced in the last paragraph. Note the symbol indicates an attractive force being formed between the islands. In FIG. 21*b* the top view 21-2 of the adjacent islands are being prepared to modify the energy barrier. The islands at (1, 2), (2, 2) and (3, 2) are made positive. The islands at (1, 1), (3, 1) and (2, 0) are charged negative. Note that semi-circle is charged differently when compared to FIG. 19*b*. For example, the islands at (1, 0) and (3, 0) are not charged at all. However, there is enough of a repulsion barrier formed by the three charged islands to push the daughter substrate in the y-direction. This also shows that other charge configurations are possible.

The next step is illustrated in the top view 21-3 shown in FIG. 22-1*c*. The islands at (2, 1), (5, 1), (5, 4) and (2, 4) are charged negatively as indicated by the symbol and repels the daughter substrate. The attractive force of the positively charged islands on the mother substrate which are located in the next row above each of the islands on the daughter substrate reduces the energy barrier and forces the daughter substrate to move in the y-direction. The daughter drops into place at the next set of islands located at (2, 2), (5, 2), (5, 5) and (2, 5) as indicated in the top view 21-9 of FIG. 21*d*.

A daughter substrate may need to be rotated in place. FIGS. 22 illustrate how the energy barrier can be altered to impose a rotational movement on the daughter substrate 22-3. In FIG. 22*a* the top view 22-1 shows that the daughter substrate has internal Coulomb islands 22-2*a* and 22-2*b* that are charged positively. The corner islands, for instance 22-4*c* and 22-4*b*, are charged negatively. The top view 22-6 depicts the mother substrate 20-1 in FIG. 22*b* with the daughter substrate 22-1 juxtaposed. The Coulomb islands on the mother substrate are at (2, 2), (5, 2), (5, 5) and (2, 5) and are charged positively. The forces at these juxtaposed charged islands are attractive; thus, the daughter substrate is connected to the mother substrate. Finally, an identification pin 22-5 is placed on the daughter substrate to help identify the amount of rotation.

FIG. 22c illustrates the top view 22-7 of the charging of the adjacent islands to create the energy barriers appropriate to perform a rotation. By symmetry, as before, only the forces with one corner are explained since the remaining corners are similar in structure, would be charged the same and would therefore behave similarly. The corner associated with the Coulomb island 22-4b that is charged negatively is used to explain the rotation. As mentioned earlier, the island at (5, 5) on the mother substrate is charged positively. The islands at (5, 4) and (6, 5) are charged negatively. The islands at (4, 5), (4, 6) and (5, 6) are charged positively. In addition, the island at (3, 4) is charged negatively to help attract the inner island 22-2b on the daughter substrate. The top view 22-8 in FIG. 22d shows that the island at (5, 5) of the mother substrate flipped the charge from positive to negative. By symmetry, the three other islands have flipped their charge also. The daughter substrate is raised over the mother substrate. The two islands at (5, 4) and (6, 5) repel the island 22-4b on the daughter substrate. However, the islands at (4, 5), (4, 6) and (5, 6) attract the island 22-4b. By symmetry, the energy barrier surrounding all the corners islands of the daughter substrate are similar in form and cause the daughter substrate to start to rotate in the counter-clockwise direction 22-9.

FIG. 22e illustrates the top view 22-10 with the daughter substrate rotated 45° as indicated by the current location of island 22-4b. The symbols used on the daughter substrate are changing their relative orientation due to the rotation of the daughter substrate. Corrections for the symbols within the daughter substrate are made in FIG. 22f. The island at (3, 6) is charged positively and is used to help position the island at 22-4b after the daughter substrate partially rotates Once the island 22-4b passes the midpoint of a line drawn between the islands of (3, 5) and (3, 6), the polarity of the charge placed on the island (3, 6) is flipped to be negative as shown in FIG. 22f. This helps to continue the movement of the island 22-4b towards its destination. In addition, the charge on the island at (2, 5) is flipped from a negative to a positive charge; thereby, further encouraging the rotation of the daughter substrate since an attractive force is formed between the islands 22-4b and the island at (2, 5). Furthermore, an additional force is helping to position and rotate the daughter substrate by the positive charge of the internal island 22-2b and the negative charge of the island at (3, 4).

Figure 23A:
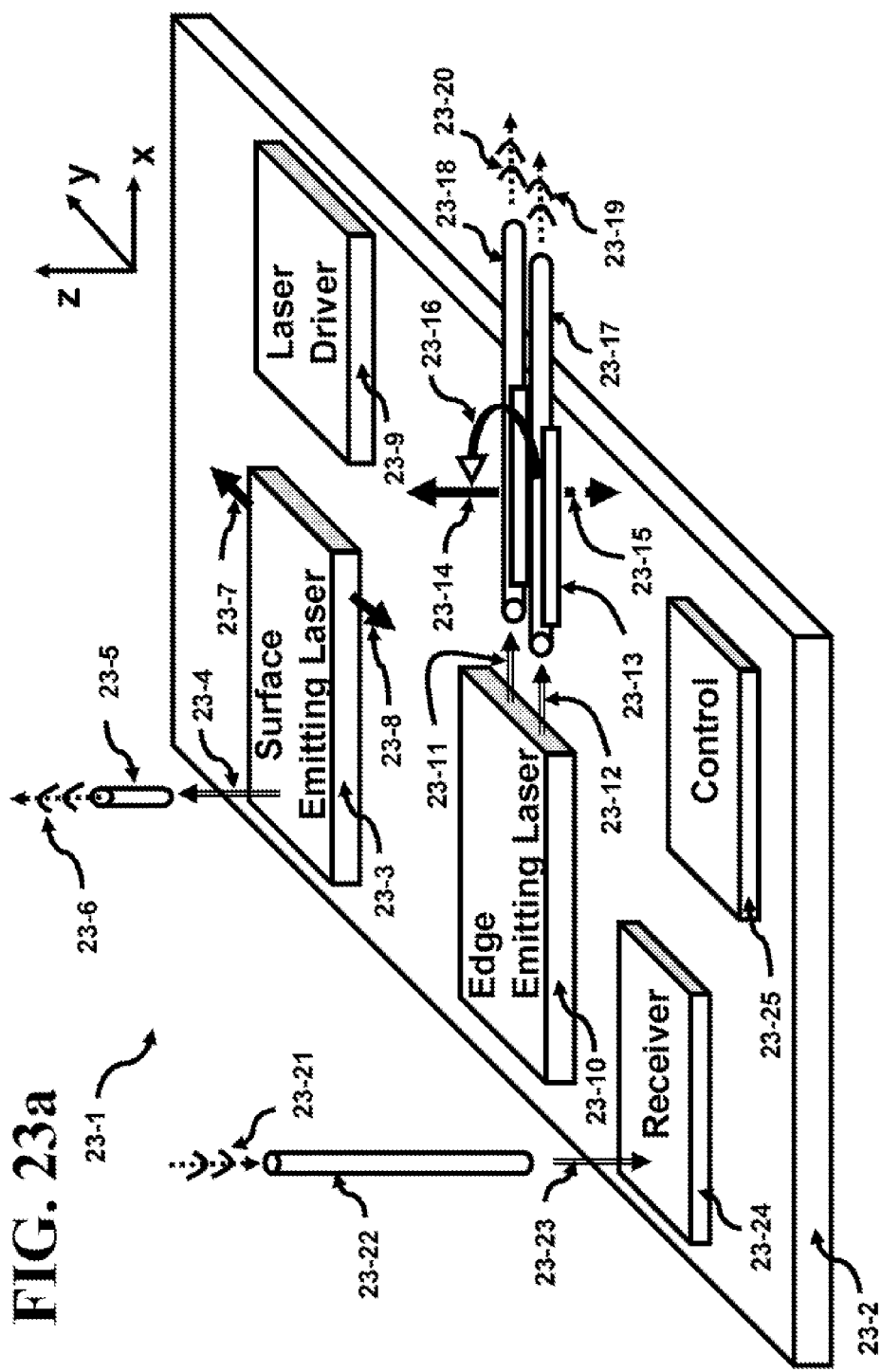
FIG. 23a) depicts a reconfigurable system consisting of multiple daughter substrates on a mother substrate to receive and transmit laser radiation, b) illustrates a flowchart to position the receiver to the laser radiation and c) reveals a flowchart to position the V-Groove holding fibers to the edge laser in accordance with the present invention.

FIG. 22g depicts the top view 22-11 of the position of the daughter substrate after being rotated 90°. The optional step can be used to discharge the islands that are not responsible for holding the two substrates together. The final top level view 22-12 is illustrated in FIG. 22h and an attractive force is formed at all charged islands that are juxtaposed to one another. Thus, Coulomb islands if sequenced to be charged properly can be used to lift, rotate, move and drop daughter substrates on a mother substrate A Laser Interface System 23-1 (LIS) is illustrated in FIG. 23a. The system has a mother substrate 23-2 with several daughter substrates on its surface. The list of substrates includes a receiver 23-24, control unit 23-25, edge emitting laser 23-10, V-groove fiber holders 23-13, laser driver 23-9 and a surface emitting laser 23-3. The control 23-25 determines the current positions of the movable substrates, calculates the require sequence of movements required to achieve the final substrate configuration, performs the fine tuning the alignment of the fibers to the substrates, and connects the substrates to the mother substrate if required. Note that the control unit can also be combined with other circuits inside the mother substrate 23-2. Some of the signals transferring to and from the LIS are optical in nature. The receiver 23-24, edge emitting laser 23-10, V-groove fiber holders 23-13, and a surface emitting laser 23-3 are called optical components. For instance, 23-21 is an input laser signal for the fiber 23-22 and provides an optical signal 23-23 to the receiver 23-24, while the output laser signal 23-4 emitted from the surface emitting laser 23-3 passes into the fiber 23-5 and passes the signal 23-6 in the fiber to another location. The edge emitting laser generates two laser signals 23-11 and 23-12 which enter the fibers 23-17 and 23-18, respectively. These two fibers send the signal 23-19 and 23-20 to other locations. Alignment between the core of the optical fiber and the sensor or laser output is required to insure maximum power transfer between the two components. The conventional process of making the alignment is complex and may require operator assistance. This is a costly issue and ways of reducing the cost would be beneficial. Note that due to Coulomb islands and forces the alignment can be done electronically by using control techniques such as feedback correction using a closed loop. A closed loop feedback system as described in U.S. Pat. No. 5,298,800 can be used. The reason an alignment can be made is because the components can be positioned by using Coulomb forces. For instance, the moveable components such as the surface emitting laser 23-3 can move laterally as indicated by the two directions 23-7 and 23-8. The orthogonal movement, although not shown, an also occur. Vertical movement such as 23-14 and 23-15 are illustrated for the V-groove holder 23-13. In addition, rotational movement is also possible as indicated by the arrow 23-16 associated with the V-groove holder. The steps required to perform these movements have been described in detail earlier. It is also possible to use MEMS mirrors and place these mirrors between the lasers and the fiber to adjust the laser beam into the fiber.

Figure 23B:
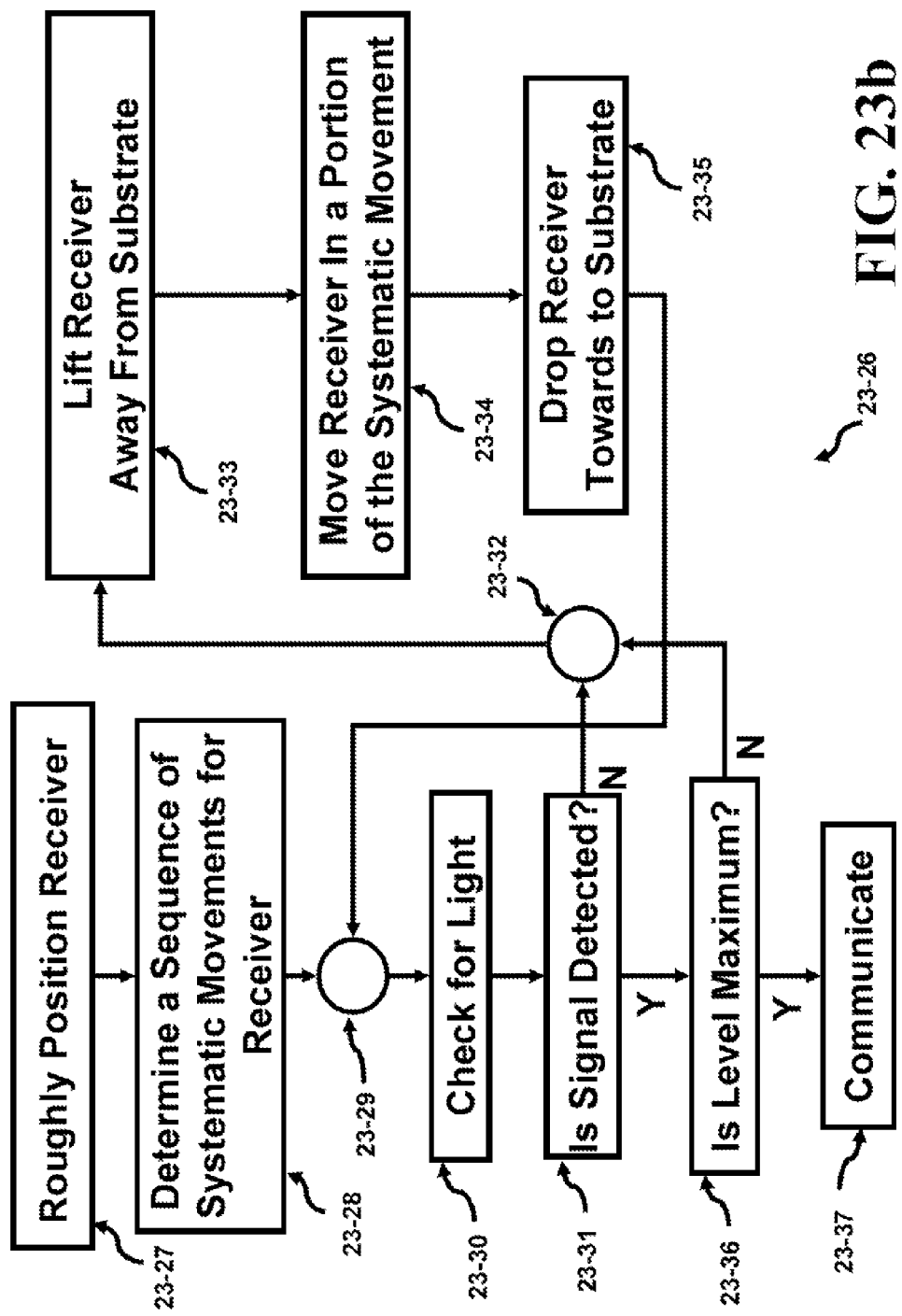

FIG. 23b illustrates a flowchart 23-26 to position the laser receiver. The positioning of all the components at a global level was covered in the flowchart 1-25 shown in FIG. 1k. The receiver is positioned roughly as indicated by 23-27. The remaining portion of the flowchart 23-26 performs a fine adjustment of the receiver's position to align the fiber to the laser. The sequence of systematic movements is calculated by a control chip 23-25 that uses a Finite State Machine (FSM). This sequence could be as simple as an x-y scan; that is, scan in the positive x-direction, move in the y-direction, scan in the negative x-direction, etc. Check the light in 23-30 and determine if the signal is detected in 23-31. If the signal is not detected, lift receiver away from the mother substrate 23-33 and move the receiver in one of the portions of the pre-calculated movements 23-34. Drop the receiver to the substrate 23-35 and check for light 23-34. If signal is detected, see if signal is at a maximum 23-36. If not, then proceed through the steps 23-33, 23-34, 23-35 and determine if level is a maximum. The determination can be done by matching the position of the receiver with the signal level in a memory, and then the maximum level can be determined by a search of the memory. These positions are applied to the receiver and communication 23-37 can occur.

FIG. 23c depicts another flowchart 23-38 of a control unit that addresses aligning the V-groove unit to the edge laser. The determination of sequence of movements 23-39 is calculated. For instance, movement in the y-z plane can be calculated. Z is perpendicular to the surface of the substrate. Prepare the feedback system to respond to the changes being made 2340. This requires the reception of a signal from the fiber which is then send back to the control unit to determine optimum operation. Roughly position the edge laser (flowchart of FIG. 1k) and turn on laser and emit light 22-42. The fiber is checked for light 23-44, if none found, move the V-groove in one of the sequence steps 22-46. The V-groove is being moved instead of the laser so the laser can have a solid thermal and electrical contact with the mother substrate. However, the laser can be moved instead if a good source of electrical power contacts can be provided and the heat dissipation issue was not a significant problem. An example given previously described the levitation of a daughter substrate with bonding wires attached. Such an arrangement would be able to provide an electrical power contact for the laser. Once light is detected, the next step is to determine if the intensity is at a maximum 23-47. If not, then a systematic movement of steps 22-46 can be performed to maximize the light. The systematic movement can also comprise steps to tilt or angle the V-groove to improve the intensity. The feedback values are stored in memory along with the physical attributes (x, z, and angle). Once the maximum is located, the attributes can be applied to the V-groove apparatus to position it to the attributes. Then, communication 23-48 can occur.

Figure 24A:
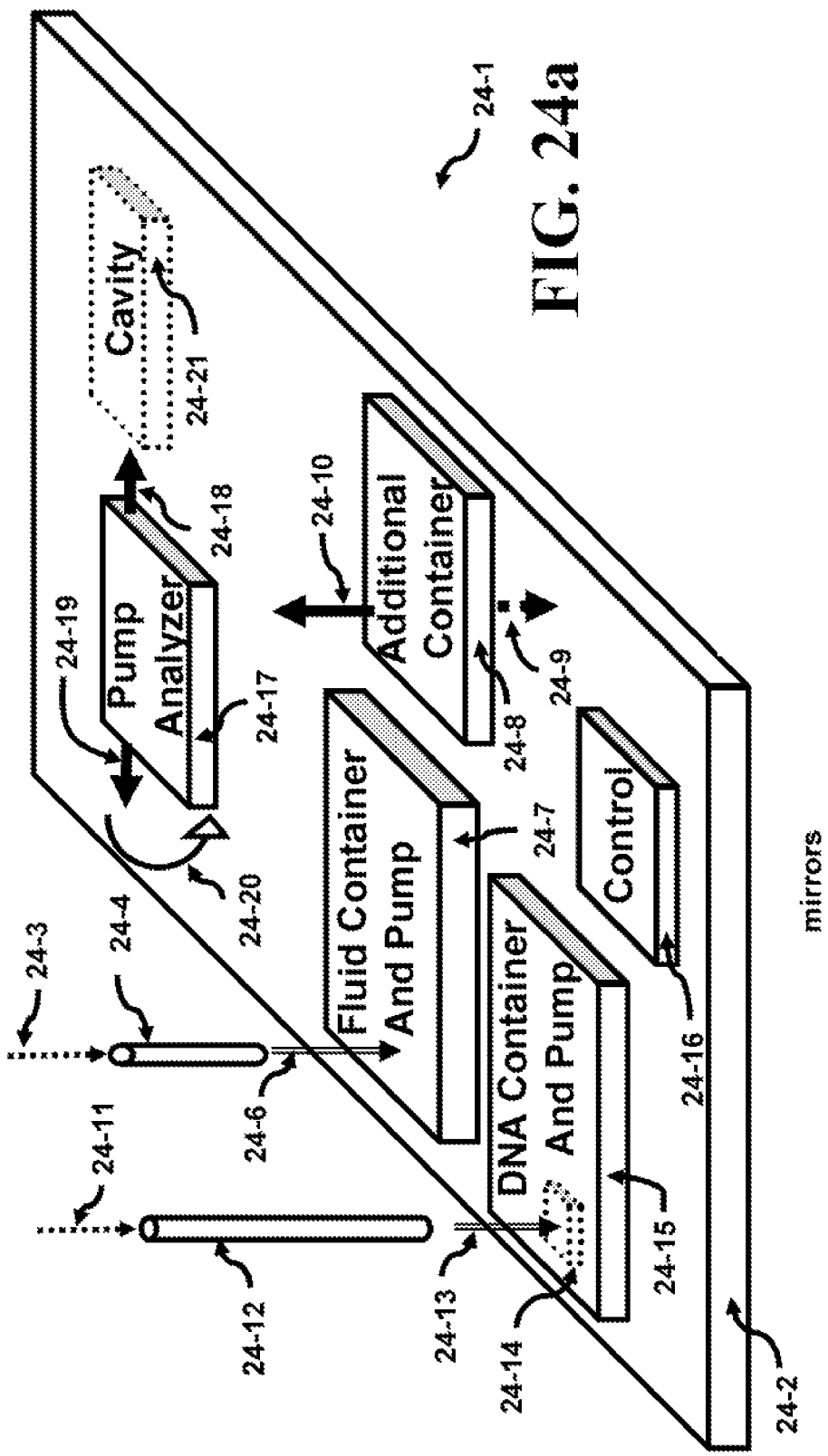
FIG. 24a) shows a reconfigurable Lab On a Chip (LOC) System consisting of multiple daughter substrates on a mother substrate to receive, mix and analyze biological components, b) defines the contact angle of drops and c-d) illustrates movements of the daughter substrates with drops having large contact angles to make contact with other drops in accordance with the present invention.

A LoC (Lab on a Chip) 24-1 is illustrated in FIG. 24*a*. Fluids 24-11 and 24-3 are pushed through pipettes 24-12 and 24-4 to deposit samples 24-13 and 24-6. The mother substrate 24-2 can hold several daughter substrates, cavities or both. In addition, the daughter substrate can have cavities, for example, the daughter substrate 24-15 DNA container and MEMS pump can have at least one cavity 24-14 formed in it. MEMS pumps are used to pump contents between cavities located on the same daughter substrate or between the daughter, and another daughter or the mother substrate. The pumps can extract a certain volume of fluid from a cavity or insert a volume of fluid into the cavity. The egress and exit openings can be fabricated in the daughter substrate and can be located on a surface of the daughter substrates, on their edge, or their bottom surface. The cavity 24-14 can be moved under either pipette 24-12 and 24-4 to collect the samples 24-13 or 24-6. Fluids such as; proteins, blood samples, buffers, reagents, and living organisms in liquids in additional containers or cavities can also be located on different substrates 24-7 and 24-8. For instance, a reagent can be used to determine protein concentration while buffers can be used to extract DNA from whole cells. The pump analyzer 24-17 can rotate 24-20, move laterally (24-19 and 24-18) and pump contents either from/to a cavity. The analyzer 24-17 can also analyze the fluid for concentrations and other properties. Finally, the vertical motions (24-10 and 24-9) of the daughter substrate 24-8 can provide additional movements to perform surface properties characteristics and studies. Although not indicated, the 24-8 substrate can contain a pump. The control 24-16 is shown on the surface of the mother substrate, but can be completely incorporated in the mother substrate, shared between the mother substrate and each of the daughter substrates, shared between a control unit 24-16 and the mother substrate or any combination of these. The control unit can receive its direction from external signals (for instance, passed from the PWB (Printed Circuit Board) through the package to the substrates) that exist in external memory or can be calculated on the fly by an internal/external processor.

Figure 24B:
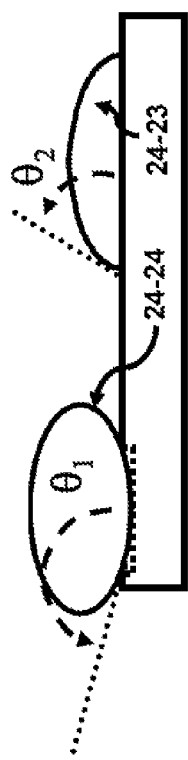
FIG. 24e) presents a flowchart to position the cavities to receive samples from a pipette and f) depicts a flowchart to position the containers to deposit reagents into carriers to perform operations and analysis in accordance with the present invention.
Figure 24C:
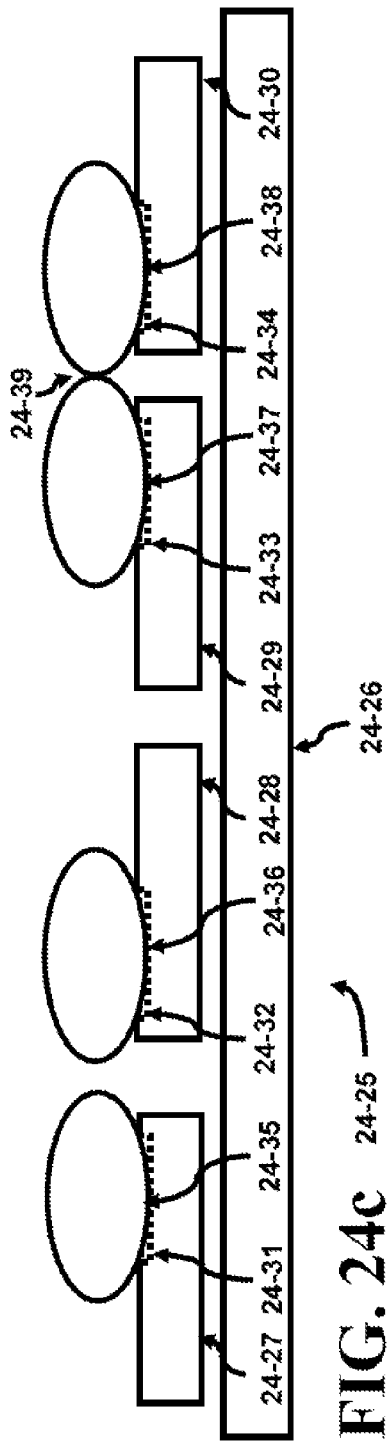

A cavity is filled with a fluid when the forces due to the mass of the fluid just equal the forces holding the surface together. In this condition, the surface tension can generate two different contact angles ($\theta_1$ and $\theta_2$) as depicted in FIG. 24*b*. Once the contact angle is greater than 90°, the fluid can overhang the substrate as illustrated by the drop 24-24 where the contact angle is $\theta_1$ in FIG. 24*b*. The shape of the drop for a contact angle less than 90° is shown by the drop 24-23 with an angle of $\theta_2$. FIG. 24*c* illustrating a cross sectional view 24-25 of a LoC system. Some of the cavities on the daughter substrates can be filled with fluids and form a variety of contact angles with the substrate. These cavities can be formed near the edge of the substrate such that the contact angle is greater than 90° and causes the liquid to overhang the substrate. The mother substrate 24-26 is under the levitated daughter substrates 24-27 through 24-30, each having at least one cavity 24-31 through 24-34, and each having a drop of fluid 24-35 through 24-38, respectively. All of the drops have a contact angle greater than 90°.

In FIG. 24*c* the daughter substrates 24-29 and 24-30 are moved close to each other using the Coulomb force due to the Coulomb islands until the overhangs touch each other 24-39. Note that the daughter substrate 24-29 is not in contact with the daughter substrate 24-30. The control unit (not shown) determines the procedure of charging the Coulomb islands to move the daughter substrates so the daughter substrates perform the required moving actions. In addition, the control unit may perform additional steps; applying voltage potentials across the common surface, measuring the current that flows between fluids, adjusting the concentration of the fluids, etc.

Figure 24D:
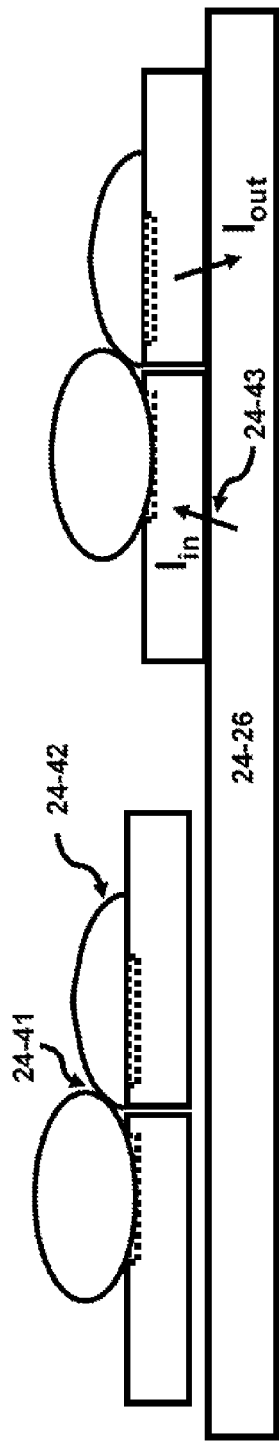

Once the contact is made several studies can be carried out. The surfaces of the liquids are now in contact and studies may be conducted on the surface properties of these two liquids to determine if diffusion between the fluids occurs even if the surfaces are not broken. This substrate arrangement offers the ability to study the characteristics of: 1) surface features of the same or different fluids whose surfaces are placed in contact with one another; 2) potentials can be applied to each fluid to study the transfer of charged ion components between the fluids; 3) using a pump, some of the fluid can be extracted then additives can be added to either fluid to see how changing the characteristics of the fluid affects either the solution or the surface properties; 4) using the pump, samples of the fluid can be extracted and analyzed to determine its properties; 5) one substrate can be moved laterally to rub the surfaces together to determine a "coefficient of friction"; and 6) to determine when and if the surfaces breaks and under what force was required to do so. FIG. 24*d* illustrates another cross sectional view 24-40 where a drop with a contact angle greater than 90° can be placed in contact with a drop having a contact angle less than 90° as shown by the contact point 24-41. The substrates can be connected to the mother substrate and a current 24-43 can be forced to flow from one drop to another. Another test is just applying a potential difference between the two drops in contact. Some of these tests require a microscope and human observations while others can be performed entirely by the control unit.

Figure 24E:
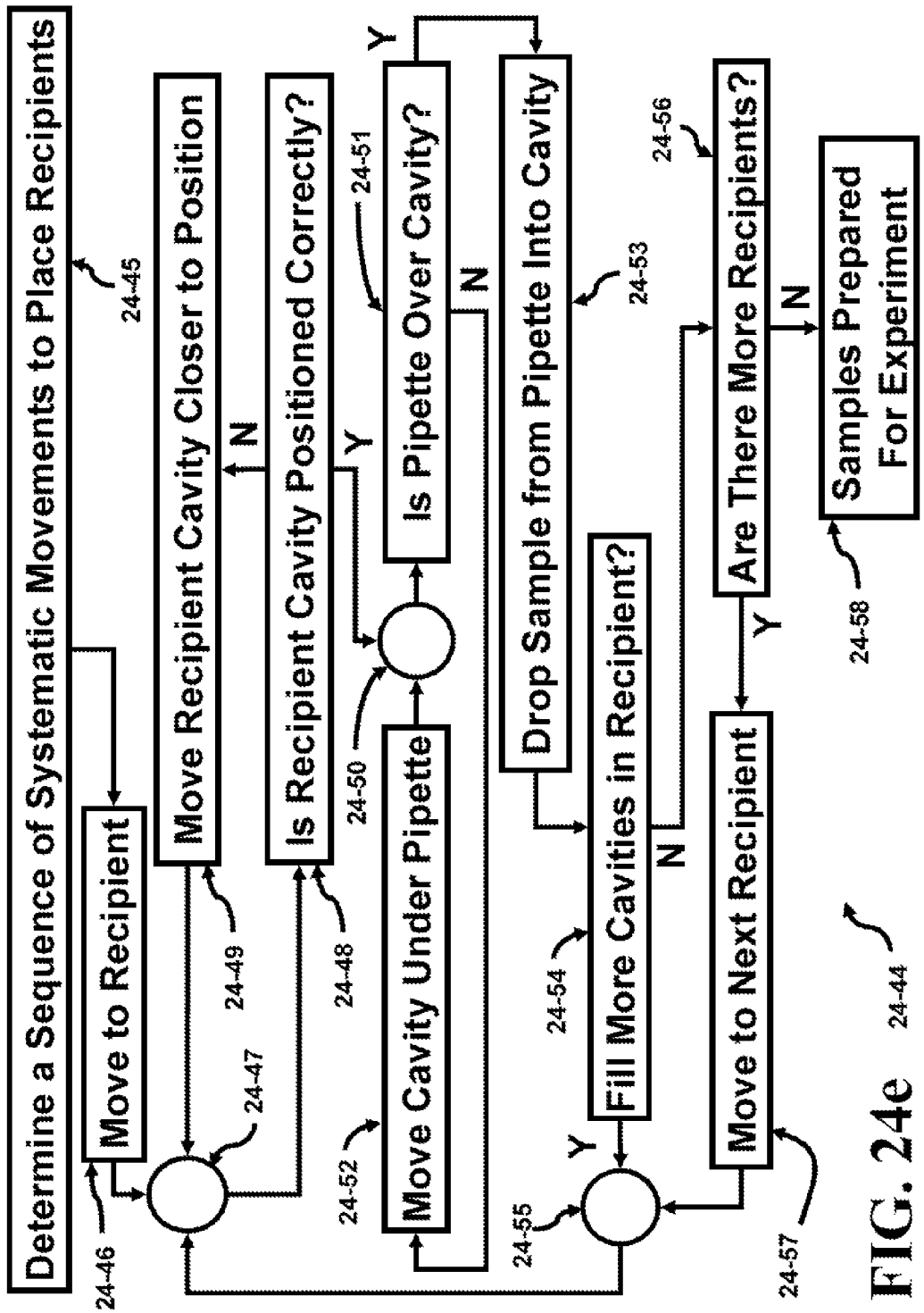

FIG. 24*e* provides a flowchart 24-44 for positioning the pipette and dropping samples into cavities. As the pipette gets close to a substrate, capacitances are used to determine their distance and position. The capacitor can be formed between the tip of the pipette and the cavity. The first step is to determine a sequence of movements to place cavities under the pipettes 24-45. Pick the first recipient 24-46 and determine if recipient is in the right position 24-48. Move recipient until it is positioned correctly 24-49. Determine if the pipette is over the cavity 24-51, if not, position the cavity better 24-52. Otherwise, drop a sample from the pipette into the cavity 24-53. Determine if there are more cavities in recipient 24-54, if there are determine next cavity and go to 24-48 and repeat previous steps, otherwise determine if there are more recipients 24-56, if there are move to next recipient 24-57 and select cavity, place cavity in position 24-48 and repeat previous instructions, otherwise samples are prepared for experiment 24-58.

Figure 24F:
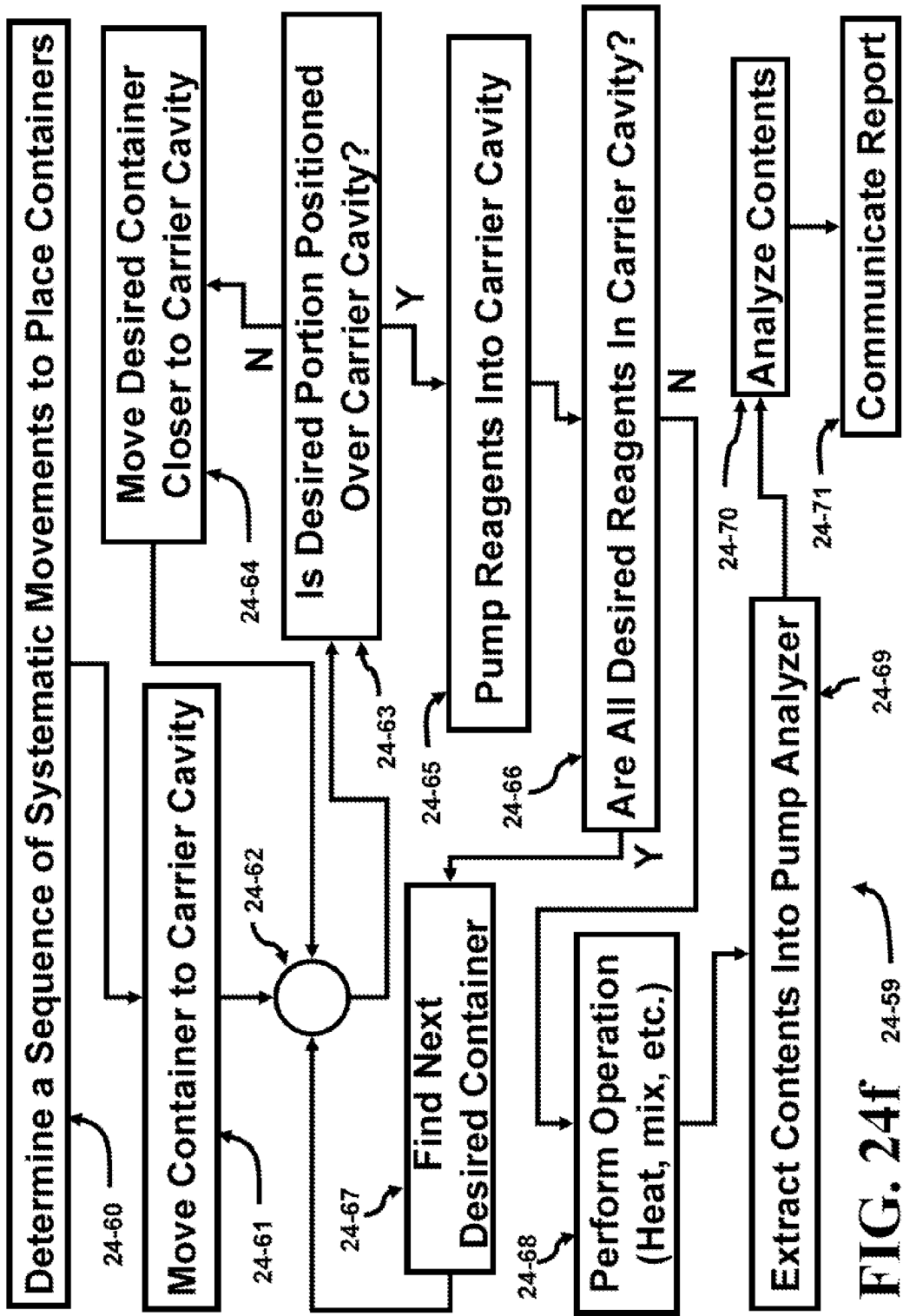

As the containers are moved, capacitances are used to determine their distance and position. FIG. 24*f* provides a flowchart 24-59 for positioning the container and pumping samples into/out-of cavities in the mother substrate. A sequence of moves 24-60 is determined by a control unit.

Note that another possibility is to calculate a portion of the steps required to position the containers and determine the rest of the movements on the fly. Then the first step is to move a container to the carrier cavity 24-61. Is the desired portion of the container over the cavity 24-63? If not, move the container until it is closer. 24-64. The desired portion of the container can have a hole drilled through the daughter substrate such that the hole overlays the cavity. Then a pump can force the reagents/buffer/fluids into the cavity 24-65 through the hole in the substrate. Check to see if there are other fluids/reagents/buffers that need to be added 24-66, if so, go to next container 24-67 and repeat steps for pumping. Otherwise, perform operation 24-68 which may include heating, mixing, vibrating, etc., then pump contents into the analyzer 24-69, analyze the contents 24-70 and communicate results to user 24-71.

FIG. 25 illustrates the movement of a grand daughter inductor that can move over daughter substrates. The first position of the substrates 25-1 are shown in FIG. 25a. The mother substrate 25-2 has three substrates directly on it: memory 25-10, microprocessor 25-6 and an auxiliary substrate 25-5. Then, two grand daughters 25-3 and 254 are place on the daughter substrates 25-6 and 25-5. The grand daughters are inductors and can be used by the microprocessor 25-6 in a PPL (Phase Lock Loop) or LC tank circuit to generate a clock signal. Changing the inductors changes the frequency range of oscillations of the PLL. Note that a grand daughter substrate can span over two daughters simultaneously as shown in FIGS. 25a and 25d. One possible advantage is that the microprocessor 25-6 may not require the Coulomb islands at all if most of the inductor overlaps the other daughter substrate 25-5. The substrates 25-5 and 25-4 would have the coulomb islands and they would be designed to support the entire inductor substrate 25-4 even if a portion of the inductor substrate is overhanging. This overhang portion would have at least two electrical contacts for each lead of the inductor substrate 25-4 and would overlap the microprocessor 25-6 to mate with its exposed electrical posts to complete the PLL circuit. If the second inductor is desired to change a frequency of operation, the remaining Figures depict how the two inductor substrates can be swapped. The first step is to lift and move the first inductor substrate 25-4 in the direction 25-7 to the location shown in 25-8, then as illustrated in FIG. 25b move 25-4 in the direction 25-9. Once the first inductor substrate 25-4 provides an opening for the second inductor substrate 25-3 as shown in 25-11, move 25-3 in the direction 25-12 until the inductor substrate 25-3 arrives in the position shown in 25-13 of FIG. 25d. Once the inductor substrate has its electrical contacts aligned over the posts, the inductor is dropped to make electrical contact. Note that the substrates 25-5 and 25-6 remained stationary when the inductor was exchanged.

In some cases of exchange, both the daughter and grand daughter substrates can move simultaneously to make exchanges. This adds complexity to the control of the system since the grand daughter substrate moves with respect to the daughter substrate while the daughter substrate moves with respect to the mother substrate. The path that the grand daughter sweeps out with respect to the mother substrate can be quite complex. However, in some cases, such a path can provide quicker reassembly, lower power dissipation, construction of an unusual design, or some other cost function. The control unit can be programmed to select the appropriate algorithm to perform the required moves for the given cost function.

FIG. 26a depicts an accelerometer 26-1 that can detect a lateral and vertical acceleration or deceleration. The structure comprises a mother substrate 264 with capacitor plates (26-5 and 26-6) while the remaining components shown are charged Coulomb islands. The daughter substrate 26-3 with capacitor plates (26-7 and 26-8) while the remaining components shown are charged Coulomb islands. Note that the lower Coulomb islands in 26-4 can have a different width than those found in 26-3. This will offer the movement of the daughter substrate with: 1) a more controlled height vs. displacement; and 2) offer more elasticity to the movement of the upper substrate since the forces from the lower substrate are spread out over a larger area thereby equalizing the force between the two juxtaposed islands over short distances. A top view 26-9 of the metallic capacitor is depicted in FIG. 26b which is the view from 26-2 of FIG. 26a. The letter endings of M and D correspond to the Mother and Daughter substrates, respectively. The first capacitance between the capacitor plates 26-5M and 26-7D can be measured and compared with the second capacitance of the capacitor plates 26-8D and 26-6M. In addition, these values can be compared with the system at rest or at the equilibrium position. The first and second capacitance should approximately be equal at the equilibrium position.

In FIG. 26c, the upper Coulomb islands 26-11 and 26-12 are negatively charged, while the lower islands 26-13 and 26-14 are charged positively and negatively, respectively. The islands 26-11 and 26-13 attract while the island 26-12 and 26-14 repel. The widths of the islands were discussed previously. Now assume that the system 26-10 is quickly accelerated to the right. This causes the daughter substrate to lag the mother substrate as shown in FIG. 26c. The lag 26-15 causes the upper capacitor plates to shift with respect to the lower capacitor plates. For example, the distance 26-16 is less than the distance 26-17; thus, the capacitance of the two pair of capacitors (26-7 and 26-5; 26-8 and 26-6) can be calculated to determine the direction and acceleration of the system. The top view 26-9 of the capacitor plates are illustrated in FIG. 26d. One can visually see displacement. By measuring the time and lag (by capacitive techniques) between the two sets of capacitor plates, and knowing the mass of 26-3, all Coulomb forces, distance of substrate separation, mass of daughter substrate, the velocity and acceleration can be determined.

The accelerometer 26-1 in FIG. 26a can optimally detect lateral motion in one direction of the two orthogonal directions. FIG. 27a reveals the previous plate structure to detect motion in either/or both orthogonal directions. The detection of movement in the orthogonal direction requires the use of additional capacitors plates that are orthogonal to the first set. These additional capacitor plates are labeled in the top view 27-2 of FIG. 27b. The capacitor plate pairs are: 27-5D and 27-3M, 27-6D and 27-4M. Note that when the daughter substrate moves to the left, the capacitance of these two pairs of capacitor change in the same way. Thus, the electrical measurement of all four capacitors can be determined and applied to a FSM to calculate which direction the de/acceleration is occurring. Note also that accelerations in the vertical direction can also be determined since the capacitance of the capacitors will decrease/increase as the daughter substrate moves away/towards the mother substrate.

Other forms of capacitors that are useful to detect acceleration are illustrated in FIG. 27c and 27d. A single lead-multi lead capacitor 27-7 shows the circle 27-8 on the top substrate while the individual metal strips 27-9, 27-10, 27-11, 27-12, 27-13, and the remaining strips around the circumference of the circle are on the lower substrate. However, the positions can be flipped and the circle would then be in the lower substrate. The decision will depend on the location of the FSM and the location of the multi lead capacitor. If the FSM (Finite State Machine) and the multi lead are on different substrates, then additional hardware will be required to bring the signal at the leads of the multi lead capacitor back to the FSM. Thus, it would be would be more efficient to have the FSM on the same substrate as multi lead of the capacitor. As the distance 27-13 decreases due to acceleration, the capacitance between the lead 27-8 and 27-10 would increase the most. By monitoring the capacitance of these strips and applying the data to the FSM, the determination of the acceleration/deceleration can be made. In FIG. 27*d* is a triangular shaped capacitor 27-14 that can be used to determine the acceleration/deceleration. For instance, the inner triangle containing 27-15D can be on the upper substrate, while the outer triangle containing 27-16M is on the lower substrate. As the upper triangle moves the capacitance of the three closest capacitors can be measured and used to determine the direction.

Figures 28A, 28B:
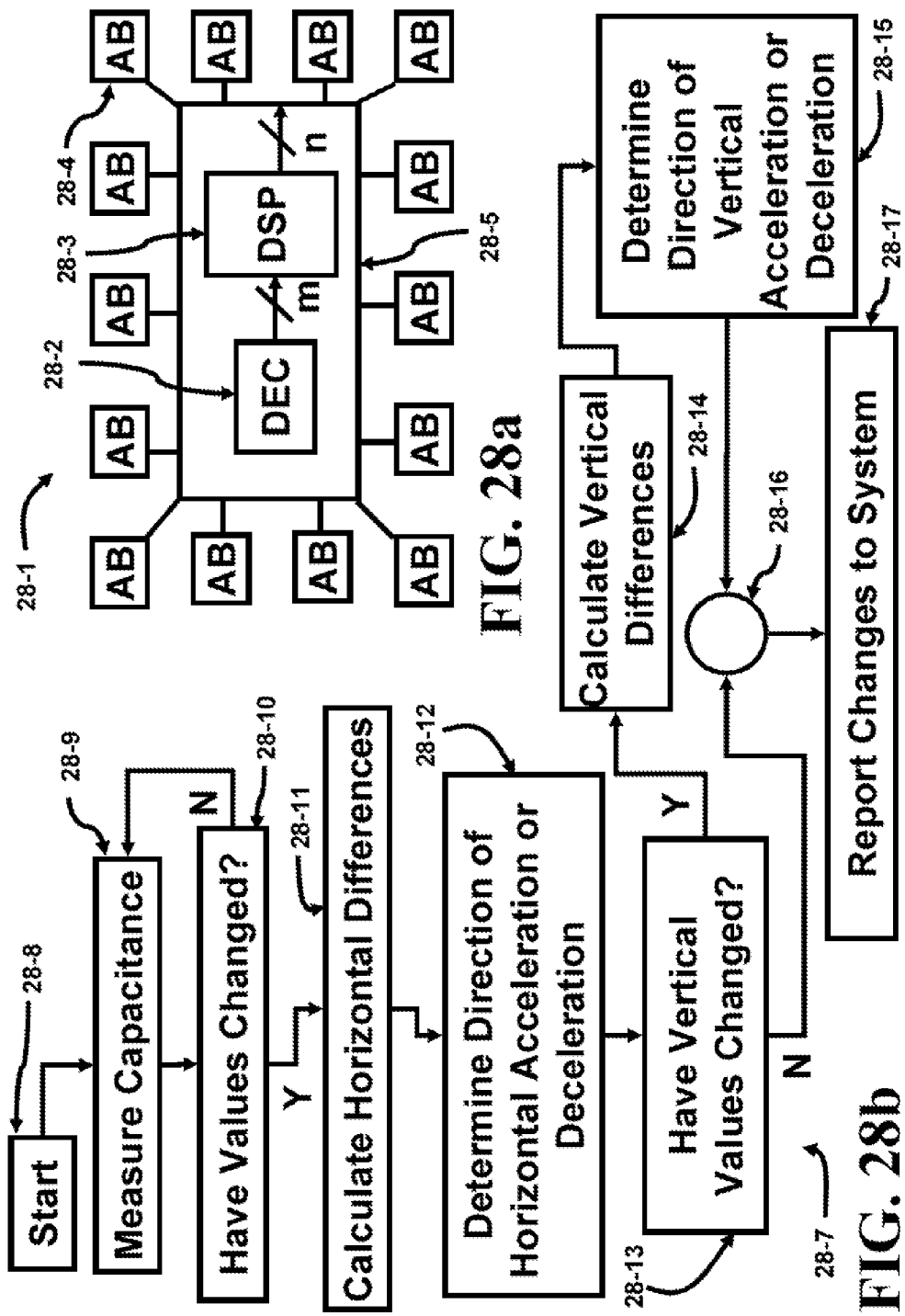
FIG. 28a) shows a block diagram of an automotive safety system using a computation unit (DSP) to determine which air bags (AB) should be enabled and b) presents a flowchart measuring the capacitance of the offset capacitors in accordance with the present invention.

FIG. 28*a* depicts a block diagram 28-1 of a movable system (e.g. automobile) with a deceleration device 28-2 which feeds information to a FSM (a DSP 28-3 is shown, but it could be a microcontroller, ASIC, FPGA, microprocessor. etc.) to be processed. The result is applied to the bus 28-5 and is applied to the airbags (AB) 284 and determines the appropriate AB's to fire and their firing sequence to minimize bodily injury due to the impact of the crash.

FIG. 28*b* illustrates the flowchart for an accelerometer which uses the levitated substrate and Coulomb islands as described earlier. Such an accelerometer may be useful in any moving vehicle. Assume the system is at rest, then go to start 28-8, measure the capacitance 28-9 (for example, the capacitance 26-5M and 26-7D) and in a loop continue measuring the capacitance until a change is noted. From the displacement of the daughter substrate determine the lateral (or horizontal) movement 28-11, then determine the direction of the acceleration or deceleration 28-12. Next check if the vertical capacitors have changed 28-13, if so, measure the vertical distances 28-14, then use these values to determine the vertical acceleration or deceleration 28-15, once all data is available report or store the information to the system 28-17.

FIG. 29*a* depicts a view 29-1 of a two layered system on mother substrate 29-2 containing a daughter and grand daughter layer. The daughter layer comprises: the FPGA 29-14, Microprocessor 29-12, DSP 29-5 and Video Accelerator 29-8; and memory substrates 29-6, 29-16, 29-10 and 29-3. The grand daughter layer comprise: the connect substrates 29-13, 29-11, 29-9, 29-4 and 29-17; and the capacitance substrates 29-15 and 29-7. The connect substrates can have many uses; one is to bypass the output/input buffers of a path connecting the core of one substrate with another, another is to electrically connect metal segments of adjacent substrates together. FIG. 29*b* illustrates a cross sectional view 29-18 of how the bypass is made, see U.S. Pat. Nos. 6,465,336 and 6,281,590. The cross section is that of the video accelerator 29-8, the connect substrate 29-9 and the memory 29-3. The video accelerator has a core and would conventionally receive data received from the I/O pad 29-20 after passing through the input buffer 29-23. The I/O pad can be wire bonded or solder bumped. The input buffer has a delay or consumes time. The memory substrate 29-3 has the M-core and conventionally applies data to the output buffer 29-19 which drives the I/O pad 29-20 and drives a low impedance environment (50Ω) of the package and PWB boards. This requires a large width transistor to apply a signal into this environment and can generate a large amount of switching noise due to the parasitic element environment. The output buffer also consumes time. To overcome the delay and noise issues, the connect substrate 29-9 can be used to tap into the internal path between the core and the I/O. These internal tap points are connected to the posts 29-21 and 29-22 and are called as I/O ports. The connect substrate 29-9 has post 29-21*a* and 29-22*a* that are shorted by a metallic path. The posts 29-21*a* and 29-22*a* make contact with the posts 29-21 and 29-22, respectively. Thus, the I/O components 29-23, 29-20 and 29-19 are bypassed eliminating their delay, noise and power dissipation. FIG. 29*c* depicts a cross sectional view 29-24 of a capacitor substrate 29-26 that connects to a lower substrate chip 29-25 which is being moved across the substrate 29-25 over the surface of a mother substrate. The capacitor substrate has been charged to the power supply, connects to the daughter substrate and can serve as an auxiliary power supply while the daughter substrate is activating its Coulomb islands to perform movements on the mother substrate. Because the charging and discharging of the Coulomb islands could use power, a capacitor substrate 29-26 rides on the daughter substrate and acts as a temporary power supply as the energy in the charged capacitor 29-27 is used, for example, see US app 20060122504. One side of the capacitor is connected to the power supply of the lower substrate through the posts 29-28 and 29-29. Similarly the other side is also connected by connected posts. The energy stored in the capacitor 29-27 can be used to allow the lower substrate 29-25 to levitate for a longer time period. Although not shown, a DC voltage regulator may be requires to maintain a constant voltage applied to the daughter substrate. When the capacitor is not used, it can be charged by being connected to a substrate that is in its final contact position and has via or similar connection through the substrate to power supplies that are accessible on the mother substrate.

As RF frequencies continue to increase in carrier frequency, the wavelength continues to decrease. The antenna used to capture this signal is of finite size and has a relationship to the wavelength. When the antenna dimensions are as follows:

$$ka<1 \tag{7}$$

where $$k = \frac{2\pi}{\lambda},$$

"a" is the radius a sphere enclosing the antenna, and λ is the wavelength. Then, the antenna is an Electrically Small Antenna (ESA) if the condition in Equ. 7 is satisfied. The ESA determines the impedance bandwidth of an antenna and the Q of the antenna. These antennas will have a lower Q.

Various frequencies are allowed for communications. The Personal Communication System (PCS) operates at 1900 MHz, Global Positioning Satellite (GPS) is at 1,500 MHz, and GSM (Global System for Mobile communications) at 900 MHz. The wavelength ranges from 16 to 33 centimeters. Forming an antenna on a substrate with a side dimension of 1 cm and using Equ. 7 would indicate that the antenna would be an ESA.

The FCC (Federal Communications Commission) has adopted rules for 71-76 GHz, 81-86 GHz and 92-95 GHz bands. The wavelength of the carrier would be approximately range from 3000 to 4000 micrometers. Depending on the final antenna design and layout, the ESA conditions are not as prevalent as they were for the PCS, GPS and GSM systems. An antenna has an optimal performance when the antenna is designed for a given frequency. As the carrier frequency changes, the transfer power of the captured signal in the antenna to the RF frond end decreases. An ideal way of overcoming this issue is to reconfigure the dimensions of the antenna so that they operate as a function of the carrier frequency. Another way is to reconfigure the dimensions of the antenna so that they operate within the center of each of the three FCC bands. The dimensions of the antenna can be redesigned on the fly using Coulomb islands. For instance, FIG. 30a illustrates a block diagram 30-1 of an RF front end 30-4 driving a dipole antenna composed of two legs 30-2 and 30-3. The length of each leg is related to the carrier frequency given earlier. Since these dimensions are in the range of thousands of micrometers, the adjustments to the length of the antenna can be done on a conventional CMOS substrate.

Figure 30B:
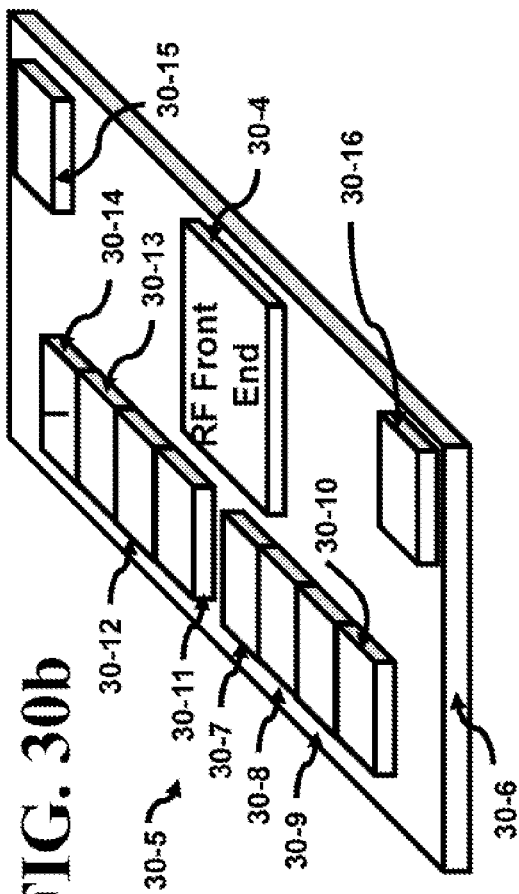
FIG. 30a) shows an RF front end connected to a dipole antenna, b) presents the construction of a dipole antenna, c) depicts an RF front end connected to a dipole antenna for higher frequencies and d) illustrates the construction of a dipole antenna for higher frequencies in accordance with the present invention.

FIG. 30b illustrates a Reconfigurable Antenna on a Substrate (RAS) 30-5. The mother substrate 30-6 carries a portion of the radio circuitry (RF Front End 30-4) closest to the antenna that is concerned with receiving/transmitting signals from/to the antenna, respectively. In addition, there are a multitude of substrates with a variety of shapes in the metallic layers that can be reconfigured as antennas. The individual antenna substrates currently appear to be similar but can be of any required size and shape to satisfy the designs goals. Although, a dipole will be described, this invention can be used to modify the dimensions of a) a patch antenna to $\lambda/2$ and control the height of the patch above a ground plane on the mother substrate, b) MIMO (Multiple-input Multiple-output) antennas, c) Yagi antenna, and 4) reflector based antennas to name a few. The RF Front End 30-4 can be connected through the mother substrate 30-6 to the antenna substrates 30-7 and 30-11 which form one end of the dipole antennas 30-2 and 30-3. The antenna substrates 30-7 through 30-10 are connected to each other to form the leg 30-2 of the dipole, while the antenna substrates 30-11 through 30-14 form the leg 30-3 of the dipole.

The antenna substrate can be: 1) connected to the adjacent antenna substrate by using the "connect substrate" discussed in FIG. 29b; 2) dropped and connected to the mother substrate and the mother substrate completes the connection; and 3) physically abutting the exposed metal features along an edge of both antenna substrates together, allowing a horizontal connection to be made between the two antenna substrates (this will be covered in detail shortly). With regards to the third point, Coulomb islands can be formed in the edge of the substrate as will be described shortly. The Coulomb forces can be used to hold the antenna substrates together.

Figure 30D:
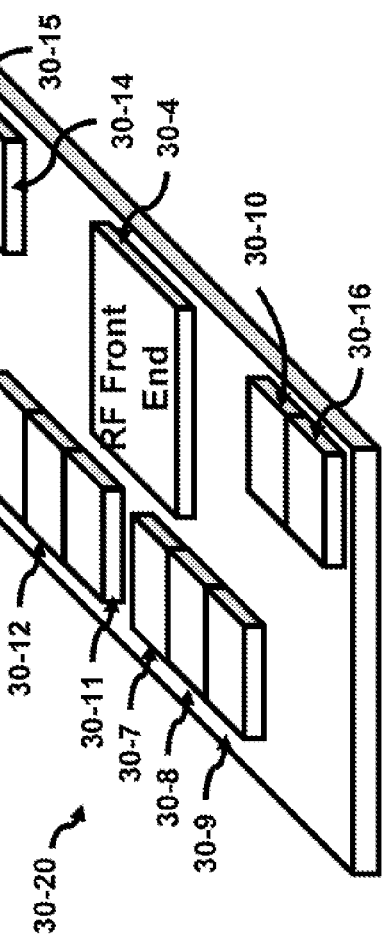
Figure 30A:
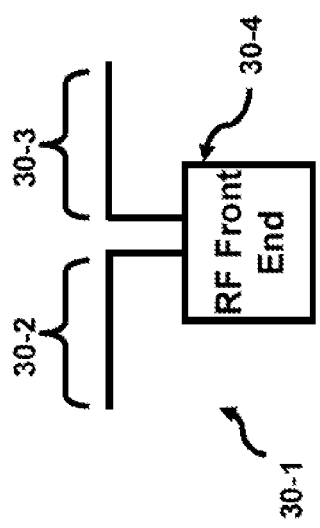
Figure 30C:
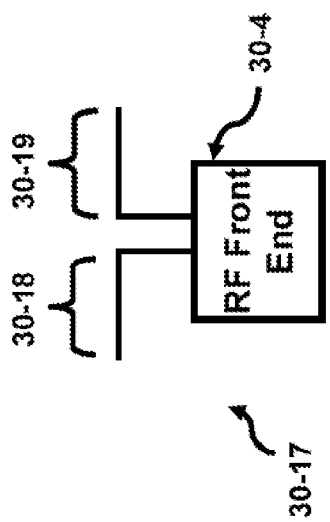

FIG. 30c illustrates the case where the carrier frequency has increased thereby requiring the dipole to be shortened. Both legs of the dipole 30-18 and 30-19 need to be decreased in length. FIG. 30d illustrates the final placement of the antenna substrates 30-10 and 30-14 after they were moved into their final position. Thus, the length of the legs of the dipoles 30-18 and 30-19 were decreased by moving the antenna substrates 30-10 and 30-14 away from the active dipole. These substrates were moved using Coulomb forces and placed next to the antenna substrates 30-16 and 30-15 respectively. Note that these extra antenna substrates can be re-positioned to make a reflector branch in the overall antenna if so desired. The reconfigurabilty of the system allows the antennas to adjust themselves as the conditions applied to the system vary. This allows radiation patterns, impedance bandwidths, operating frequency and power transfer conditions to be controlled and adjusted whenever required.

FIG. 31a reveals a Yagi antenna 31-1 connected to the RF front end 31-4. The Yagi antenna has a pair of reflectors 31-2, the active dipole antenna pair 31-3, and the directive antenna 31-5. This antenna system has been re-configured and optimized to operate at a given carrier frequency in FIG. 31b where the groupings of the metallic substrates have the same identification number as given in FIG. 31a. Several rows of metallic strips are illustrated on the mother substrate 31-7 of the antenna system 31-6. The director 31-5 is comprised of 9 metallic substrates connected together, the dipole is comprised of the set of 4 metallic substrates connected together 31-3 on each side and the reflector is formed by the pair of grouping 3-2. The extra metallic substrates are in the groupings 31-8 and 3-9. The Yagi antenna can be reconfigured as a function of carrier frequency, increasing the number of director and/or reflectors.

A patch antenna 31-11 connected to an RF front end 31-4 is shown in the block diagram 31-10 in FIG. 31c. The physical realization 31-12 is given in FIG. 31d. The patch antenna is comprised the 4×4 metallic substrate array 31-11. This array can be moved up 31-13 and down 31-14 to space the array from the ground plane to help match the impedance bandwidth. The length of the array 31-17 reconfigured to be set to be approximately $\lambda/2$. The extra metallic substrates are in the groupings 31-15 and 31-16. Note that this substrate could be used to create MIMO antennas by insuring that the front end 31-4 can accept several input/output antenna ports. Further more, depending on the size of the mother substrate 31-7 and the total number of metallic daughter substrates, separate antennas designed for outgoing frequencies can be reconfigured at the same time other separate antenna are being reconfigured for different incoming frequencies. Thus, this reconfigurable antenna system can be very diverse and offers great flexibility to the system designer by offering on the fly antenna adjustment capabilities.

An issue important to communications is the interception of orthogonal signals. Typically, orthogonal surface planes containing the antenna are beneficial. Reconfigurable techniques can be use to implement antenna on surfaces which are orthogonal to each other. The following diagram helps explain the inventive technique to achieve this capability. FIG. 32a depicts a cross sectional view 32-1 of three substrates; 32-2, 32-3 and 32-4. The substrates 32-2 and 32-3 are connected together by wafer bonding, for example, to form the 32-5 substrate. Assume that the substrate 32-5 is firmly attached to a stable support. Thus, Coulomb forces will be used to manipulate the substrate 32-4 and move this substrate in the 32-6 direction. Note the charges on the common juxtaposed islands can be modified to control movement as covered earlier. The cross sectional view 32-7 in FIG. 32b illustrates the substrate 32-4 moved one unit to the left and the islands charged to cause a rotation of the substrate 32-4 in the direction 32-9. The islands 32-9a and 32-9b repel one another to place a torque on the substrate 324. The islands to their immediate left are attractive to each other and in addition, the group of positive islands 32-6a generates an induced charge on the side surface of the 32-5 substrate. The induced charge 32-8 formed at the edge of the substrate 32-5 is negative and attracts the charged islands at 32-6a. These two later attractive forces prevent the substrate 32-4 from detaching and falling off the substrate 32-5 and furthermore increase the torque on the substrate 32-4.

Figure 32C:
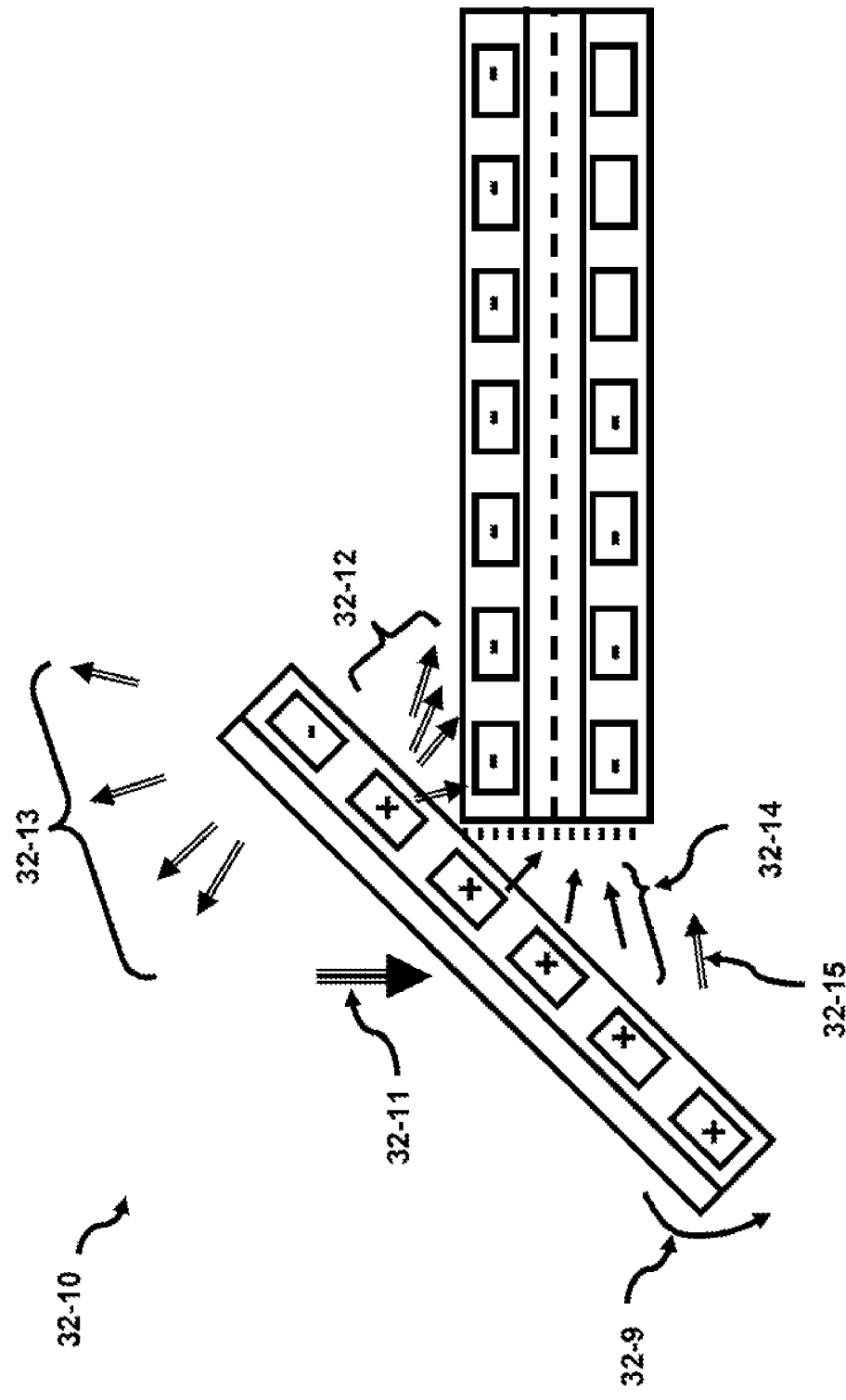
FIG. 32a-b) show the preparation stage of rotating a substrate around a corner of a second substrate, c) presents the substrate rotated less than 90°, d) depicts the substrate rotated 90° and e) illustrates the substrate rotated greater than 90° to place substrate on other side of second substrate in accordance with the present invention.

FIG. 32c reveals the net forces applied to the system 32-10 to create a rotation 32-9 of the substrate 32-4. The gravitational force 32-11 must be stabilized and overcome by the forces generated by the induced and island charges. The set of unit vectors forces 32-13 are used to provide torque to the end of the substrate. The grouping of unit vector forces 32-12 help to maintain cohesion of the substrate 32-4 to the substrate 32-5 near the pivot point. The group of unit vector forces 32-14 caused by the induced charges help to pull the substrate 32-4 towards the edge of substrate 32-5, while the vector 32-15 pulls in the same direction.

Induced charges at the edge of the substrate helps to pull the daughter substrate toward the edge of the mother substrate 32-5 as indicated by the unit vector forces 32-14. Induced charges can also be used as an attractive force while the daughter substrate moves over the surface of the mother substrate. This has not been described in detail but the basic concept of induced force can be visualized in FIG. 3c. As the negatively charged external plate 3-8 approaches the Coulomb island 3-5, the positive induced charges in the Coulomb island will attract the external plate. Thus, this Coulomb force can be used when an attractive force is desired.

Also in place of the induced charges being formed on the edge of the substrate to help attract the daughter substrate 32-4, edge Coulomb islands can be used to attract the daughter substrate. In addition, a corner substrate can be placed flush with the edge of the substrate 32-5 to provide support, additional Coulomb islands and surface area. More will be stated about the "edge Coulomb island" and the "corner substrate" shortly.

FIG. 32d shows the cross sectional view 32-16 where the substrate 32-4 is positioned orthogonal to the substrate 32-5. To lock the substrate in position, the second island from the top of substrate 32-4 should reverse the negative charge to a positive one. This would cause the unit vector force 32-19 to change from repelling to attractive which would lock the orthogonal substrate in place. The description of how a daughter substrate can be rotated around the edge of a mother substrate has been given.

However, if the substrate was desired to be moved to the bottom of the substrate 32-5 then the repelling charge that generates the unit vector forces 32-19 can be used to continue the rotation 32-9 around the substrate 32-5. FIG. 32e illustrates this rotation where only the unit vector forces 32-21 are shown. These forces enable the rotation and place the substrate 32-4 on the bottom of the substrate 32-5. The gravitational force 32-11 applied to the substrate 32-4 needs to be compensated for by the Coulomb forces. Furthermore, addition Coulomb forces are required to insure that the substrate 32-4 is pulled to the substrate 32-5. In some situations, the mass of the substrate 32-4 may need to be reduced by back grinding the foundation portion of the substrate. This can reduce the gravitational force 32-11 and allows the Coulomb forces to dominate the gravitational force. The last step of placing the substrate 32-4 on bottom of the substrate 32-5 is not shown since it is straight forward by applying the previous rules given in this specification.

An aspect that has not been used previously in the design of systems is using the edge of the substrate to perform connectivity functions. FIG. 33b reveals the cross sectional view of the edge of the substrate 33-16 before edge processing. This substrate was cut apart from the wafer using a saw. The action of the saw can chip pieces off the edge of the substrate. The edge of the substrate can be polished until the edge of the substrate appears as shown in FIG. 33b. Then further processing steps can be used to cut back the foundation and component portions 2-2, 24a and 24b of the substrate until a distance 33-17 is removed (wet etch, plasma etch, etc.). This process exposes the metal trace/via stack 33-2 where the metal stands out against the background of the oxide making this contact appears as a metallic post. However, the metal trace/via stack 33-3 is still encapsulated in oxide because this metallic stack was set back further from the edge of the substrate than the metal trace/via stack 33-2. The metal trace/via stack will be referred to a "metallic stack." FIG. 33a illustrates a cross sectional view 33-1 of a substrate 33-13 that has been processed on the edge to expose a portion of the metallic stack 33-2. The metallic stack 33-2 is exposed on its left side and a portion of the back and front of the stack 33-2 is also exposed. Note that the metallic stack 33-3 is still completely surrounded by an oxide layer. The metallic stack 33-2 comprises the metal layers 33-6 through 33-12 while the metallic stack 33-3 comprises the metal layers 33-6 through 33-10. In addition, the component portions can have Coulomb islands 33-4 and 33-6 and electrical contacts 33-5. The exposed metal trace/via stack comprising the metal layers 33-6 through 33-12 is also known as an I/O (input/Output) connection, and serves in part the same function as an I/O pad that is found on the surface of a conventional substrate which is to allow the entrance and egress of signals and power.

There are several differences between the I/O connection and the I/O pad, however: 1) the I/O pad is parallel to the surface of the substrate while the I/O connection is perpendicular to the surface; 2) a single I/O connection can have minimum dimension of in the range of one micrometer while a conventional I/O pad has a minimum dimension of 50 to 100 micrometers; thus, the packing density of the I/O connection is orders of magnitude greater than the conventional I/O pad; and 3) current can flow horizontal with respect to the substrate in I/O connection while the current flows vertically in the I/0 pad. The electrical contacts 33-5 is also known as the I/O port, and serves in part the same function as an I/O pad that is found on the surface of a conventional substrate which is to allow the entrance and egress of signals and power.

There is at least one difference between the I/O port and the I/O pad, however: a single I/O port can have minimum dimension in the range of one micrometer while a conventional I/O pad has a minimum dimension of 50 to 100 micrometers; thus, the packing density of the I/O port can be orders of magnitude greater than the conventional I/O pad. The minimum dimensions of 50 to 100 micrometers for an I/O pad is derived the mechanical tolerances of connecting the substrates in a package by using solder bumps connection or wire bonding procedures, respectively.

Note that, as done previously, any electrical connections to the metallic stacks, the Coulomb islands or the electrical contacts are not shown and have been removed to simplify the diagram. It should be understood that the electrical connections can be capacitive, resistive, inductive or any combination of these. The substrate 33-13 could be formed by wafer bonding two substrates back to back, although as described earlier, there are many equivalent alternatives possible.

The top view 33-14 indicated in FIG. 33a is shown in FIG. 33c. Note the exposed metallic stack 33-2 along with the two insulated Coulomb islands 33-3 and 33-18 on each side of the metallic 33-2 stack. The Coulomb islands 33-3 and 33-18 and the exposed metallic stack are presented in FIG. 33d from a different perspective. This figure corresponds to the view 33-15 indicated by the arrow of FIG. 33a. The two vertical metallic stacks 33-18 and 33-3 form edge Coulomb islands and can be used to create attractive Coulomb forces to hold the edge of the substrate 33-13 against a second substrate. These two vertical metallic stacks form two metallic planar surfaces, albeit these surfaces can be perforated due to the gaps between the traces. These edge Coulomb islands that are formed from the two metallic planar surfaces are perpendicular to the surface of the substrate. Meanwhile the exposed metallic stack can make an electrical connection with an exposed metallic stack on the second substrate. These stacks are composed of parallel metallic traces connected by vias also form metallic planar surfaces. The area of the exposed metal layered stricture can be proportional to the amount of current being carried.

Note several conditions with these vertical "planes": 1) the metal and via layers 33-6 through 33-12 and the metal and via layers 33-6 through 33-10 are used to form the three independent vertical planar metallic sheets (of course, it is not necessary to use all metal trace/via layers); 2) the position of the metal to the edge of the substrate is determined by the layout (positioning) of the metal layers and CAD (Computer Aided Design) layout tools can be used to automatically place these layers; 3) the connectivity can be either capacitive, resistive or inductive; and 4) they can be used as a edge Coulomb island, an edge contact or one of the plates of an edge capacitor.

FIG. 34a depicts the top view 34-1 of two substrates 34-2 and 34-3 connected at their edges. The attractive force generated by the two pair of edge Coulomb islands: 34-6 and 34-7; and 34-8 and 34-10 are used to hold the two substrates together along their edges. The metal extensions 34-4 and 34-5 or edge contacts are forced into each other at the common interface 34-15 and can be used as an electrical contact. The right substrate 34-3 has an electrical contact 34-16 that exits the bottom of the substrate 34-3. In addition, the metal trace 34-17 connects the electrical contact 34-4 to the metal extension 34-18. The regions labeled 34-9 can be used as electrical contacts or as Coulomb islands. FIG. 34b illustrates the side view along the dotted line 34-19 in FIG. 34a. The electrical contact 34-16 is connected to the metallic stack 34-21 (note that the upper portion of the stack is not partitioned into metal trace/via layers for simplicity). The substrate through via 34-23 provides an ohmic contact through the foundation portion 2-2 and allows the I/O port to connect to the metallic stack 34-21. The stack 34-21 connects to the metal trace 34-17 which then connects to the metal extension 34-5. The Coulomb force connects the two metal extensions 34-5 and 34-4 which is connected to the metal trace 34-18 within the substrate. Any metal level can be used form the metal trace within the substrate and the metal trace can be formed into various shapes using the allowable processing steps. These shapes can be used to form inductors, antenna sections, capacitors or interconnect. The Coulomb islands 34-11 through 34-14 are shown charged positively.

Orthogonal antenna configurations are an important capability for complex antenna systems. An antenna picks up signals from a transmitter typically after the signals have been reflected from various surfaces. Thus, the complete incoming signal composed of signals that are delayed, polarized in different orientations, arriving from different directions, and of course decreased in magnitude. The difficulty is the development of nulls in the radio spectrum that decreases the intensity of the information. If an antenna with a given polarization is placed right at this point then the signal intensity can be lost. The other two polarizations associated with this radio spectrum may have signal intensity at this point; but the antenna unfortunately is not equipped to capture these signals. Ideally, the complete antennas should have three antennas that are orthogonal to each other. Several reasons have prevented this from being standard equipment: 1) the cost of manufacturing the equipment; 2) the volume displaced to enable these antennas (covering three orthogonal directions); and 3) the need for three antenna ports on the front end or the ability to easily switch between the three antennas. As carrier frequencies increase, the wavelength of the carrier decreases. At 75 GHz, the wavelength of the carrier is comparable to the dimensions of the substrate allowing the formation of the antennas on the substrate. However, the invention is not limited to these high frequencies. At lower frequencies: PCS, GPS and GSM, Equ. 7 indicates that the condition will be met and the antenna would be an ESA making the design of the communication system with regards to the front end more difficult.

MIMO can benefit from this technique as well since MIMO operates on a single signal that is sent on (n) multiple antennas such that each of the (ii) signals received have traveled different paths. MIMO radio use n-antennas simultaneously to extract the n-signals and combine the n-signal energies that are related.

Figure 39:
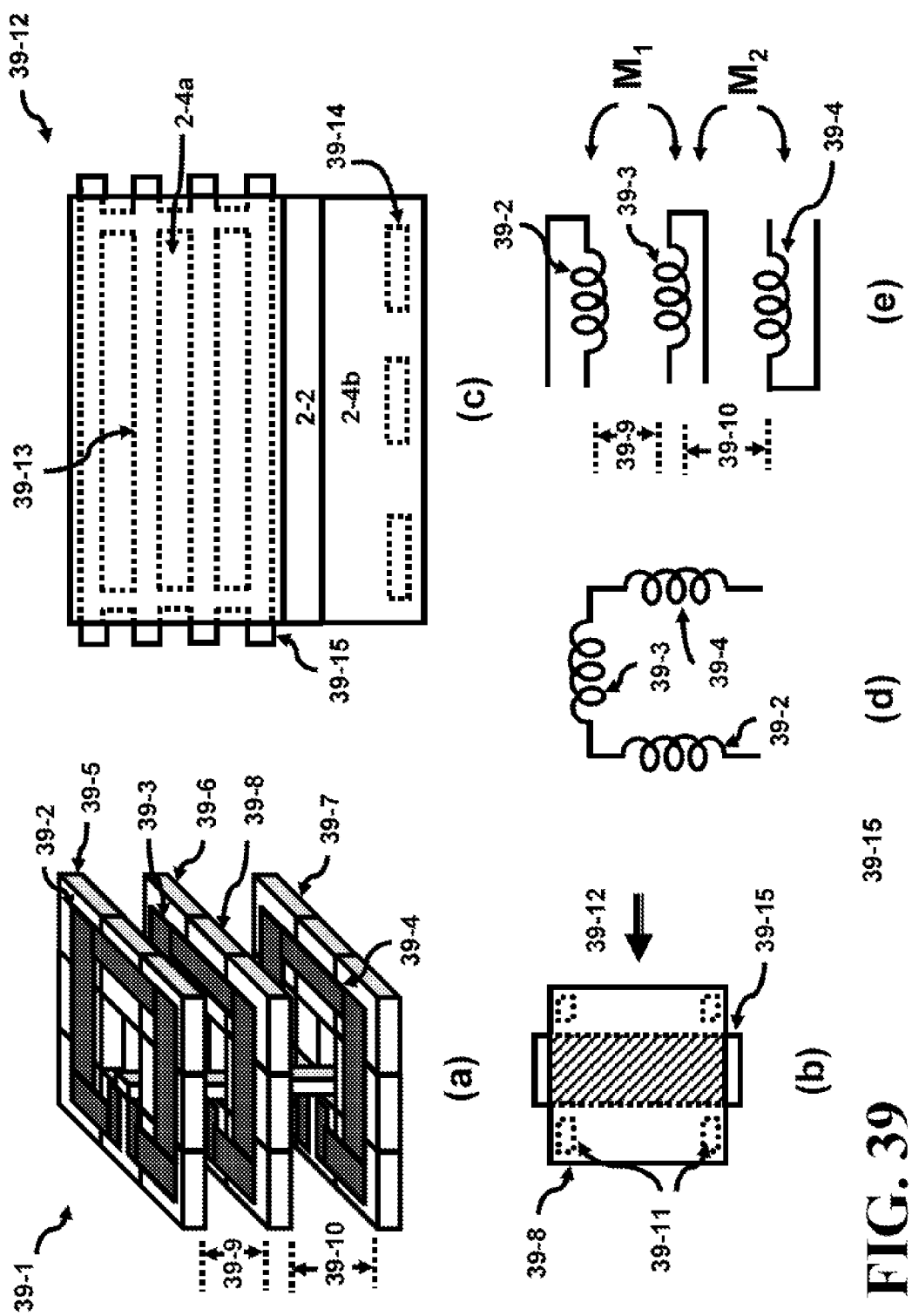
FIG. 39 depicts a) a stacked substrate forming an inductor or transformer, b) the top view of one of the individual substrates, c) the side view of the same substrate, d) series inductor and e) transformer in accordance with the present invention.

An orthogonal antenna system can intercept signals in very diverse polarizations. A three way orthogonal antenna can be designed to capture information from three different planes, which allows this technique the ability to capture more energy. FIG. 35a shows a 2D view with perspective 35-1 of a mother substrate 35-2 with a plurality of daughter substrates. The antenna substrates 35-3 through 35-8 combine several daughter substrates held together using edge Coulomb forces to generate antenna substrates that have metal patterned shapes appropriate for the formation of a variety of antennas. The entire area of the antenna substrate may be: 1) covered with metal; 2) covered with strips of metal to form a portion of a dipole, reflector or director antenna; or 3) partitioned into two or more separate antennas (for instance, the three antenna 35-16 or 35-17 shown as dotted arrows on the antenna substrates 35-7 and 35-8, respectively) where each of the separate antennas can have a separate electrical feed to the mother substrate. An example of a substrate that can be used as an antenna substrate which has a metal trace is shown in FIG. 39b. The antenna substrates can be coupled together to form metal layers that form patch, Yagi, monopole, dipole, bow-tie, meanderline, MIMO, and a variety of other antennas to be created. Many of these patterns can be reconfigured to fit different antenna specifications. Antenna substrates 35-5 through 35-8 are rotated in the direction shown until these substrates have planar surfaces perpendicular to the surface of the mother substrate 35-2.

FIG. 35b shows the system 35-10 after these antennas were rotated 90° around the edge of the mother substrate 35-2 and held in place as described in the previous diagrams given in FIG. 32. The mother substrate is held firmly in place (not shown). The three pair of antennas: 35-4 and 35-3; 35-5 and 35-6; and 35-7 and 35-8 are orthogonal to the other two pairs. Compare the orientation of the antenna substrates with the Cartesian coordinate axis shown above. Each of the pair of antennas can be configured to be one or more antennas where each one can comprise a: 1) dipole antenna; 2) patch antenna; 3) a set of MIMO antennas having the same or orthogonal orientations; or 4) any of the previous mentioned antennas. One of each pair of antennas can transmit signals at a given frequency while the other pair can receive signals at a different frequency. One of the pair of the antennas can contain several antennas at the same orientation 35-16 while the remaining pair of the antennas can have a 90° rotation orientation 35-17 as in antennas 37-7 and 35-8. In this case, a single flip around one edge of the substrate creates three antennas that are each orthogonal to the other two antennas. The transmit/receive signals are processed by the RF front end 35-9. The number of antenna/s that can be used can vary from 1 to n. The substrates 35-11 through 35-15 can be used to sent signals from either the top or bottom surface of its substrate and send these signals out of the edge of its substrate (These substrates can be called "corner substrates" since they push signals around the corner of a substrate.). The signal passes horizontally between the substrate 35-11 and the antenna substrate 35-5, for example. Vertical Coulomb islands can formed on the edges of the substrates 35-11 through 35-15. The substrate 35-11 can apply a Coulomb force to the antenna substrate 35-5 so that the substrate 35-11 can provide metallic connection to the antenna. In addition, a more rigid support is formed for the antenna substrate 35-5.

The antennas: 35-4 and 35-3; 35-5 and 35-6; and 35-7 and 35-8 can be flipped back onto the mother substrate and can be reconfigured for a different carrier frequency. Once the replaced substrates are reconfigured, the Coulomb force formed at the edge of the substrate can be used to hold these smaller substrates together to form the larger substrates: 35-4 and 35-3; 35-5 and 35-6; and 35-7 and 33-8. Then, the latter two pairs can be flipped 90° with respect to the mother substrate and mounted on the edge of the mother substrate again.

Figure 36:
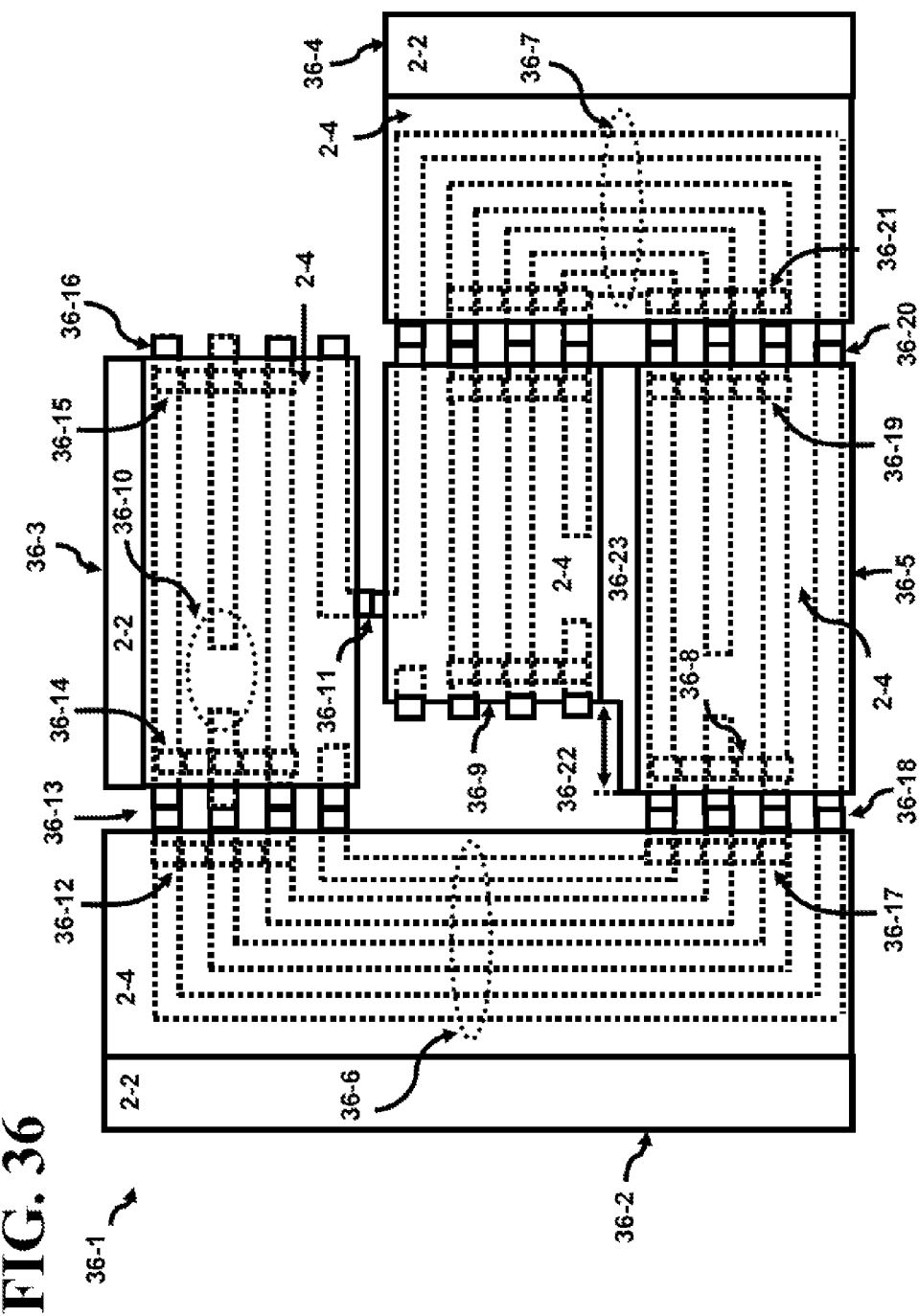
FIG. 36 illustrates the construction of a 3-dimentional substrate system in accordance with the present invention.

FIG. 36 illustrates an interconnect system 36-1 comprised of several substrate: 36-2 through 36-5. The substrates 36-2 and 364 show connections through their top surfaces only. The substrates 36-5 and 36-9 are connected together by Coulomb forces. Note that there is a gap 36-22 between the edges of the substrates 36-5 and 36-9. The region 36-23 is not shown in detail but contains a plurality of pairs of Coulomb islands that hold the two substrates together. A substrate that is normal to the page can be inserted into the gap 36-22 and connected to the contacts by the Coulomb island to the substrate 36-9 so the interconnect system can be constructed in 3-D. The substrate of 36-5 shows connections only along its edges while the substrate of 36-9 shows connections through either the edge or top surface (see I/O port 36-11) of the substrate. Substrate 36-3 shows connections through either the edge or top surfaces.

The inner substrates 36-3, 36-9 and 36-5 form several layers of substrates. One of the problems of vertical stacking of substrates is the difficulty of sending power and signals between the various layers. The two side substrates 36-2 and 36-4 illustrate how the power and signals can transfer between the various layers of the substrates. These have the metallic traces inside the component portion 2-4 of the substrate are indicated by the dotted ellipses 36-6 and 36-7. The substrate 36-2 connects the lower substrate of 36-5 to the top most substrate 36-3, while the substrate 36-4 connects the lower substrate of 36-5 to the upper substrate of 36-5.

The substrates are moved into and held in position by using Coulomb forces generated by the Coulomb islands. The process of moving and holding the substrates into position has been covered in previous paragraphs. For example, the Coulomb islands 36-12 and 36-17 attract the islands 36-14 and 36-8, respectively. Note that the Coulomb island 36-12 is parallel to the top surface of the substrate 36-2; so this island can also be called a "surface Coulomb island." The Coulomb island 36-14 is parallel to the edge of the substrate 36-3; so this island can also be called a "edge Coulomb island." Thus, a top Coulomb island 36-12 generates a top Coulomb force and is attracted to an edge Coulomb island 36-14 that generates an edge Coulomb force and the contacts 36-13 are made. The substrate 36-4 is held to the substrate 36-5 by the lower pair of Coulomb islands 36-19 and 36-21 and the upper pair (not labeled) to make the upper contact. The substrate 36-3 has the connection 36-11 to send signals between adjacent substrates in the stack. The dotted oval region 36-10 indicates that the trace on this level may have made an orthogonal turn.

Figure 37:
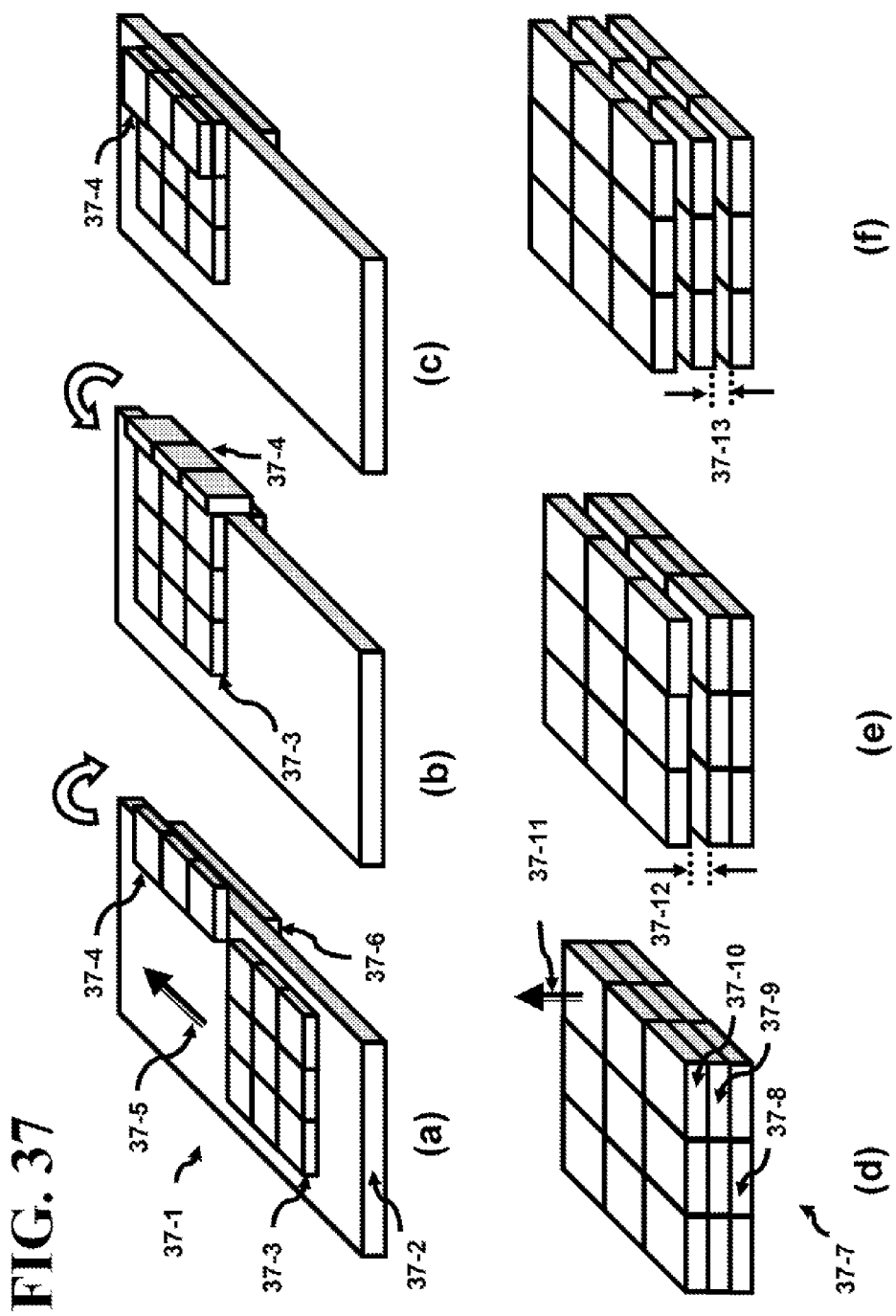
FIG. 37 depicts a) the preparation, b) the flipping, c) the stacking of one substrate on another substrate, d) a stacked substrate, e) a first levitated substrate, and f) a second levitated substrate in accordance with the present invention.

FIG. 37*a-c* reveals how daughter substrates become grand daughter substrates by using edge and surface Coulomb forces. A system 37-1 consists of a mother substrate 37-2 with two daughter substrates 37-3 and 37-4. Each of the daughter substrates can comprise one or more individual substrates. For instance, the substrate 37-3 contains 9 individual substrates while the substrate 37-4 contains three. The substrates 37-3 and 37-4 may utilize both surface and edge Coulomb islands. The individual substrates in the daughter substrate 37-3 are held together by edge Coulomb forces; the daughter substrate moves on the surface of the mother substrate by using surface Coulomb forces of at least one of the individual substrates. This is evident by observing that the movement of the daughter substrate 37-3 in the direction 37-5 requires that the moving substrate remain cohesive; the edge Coulomb forces provide this function. However, the substrate 37-3 can release the edge Coulomb forces and move each of the individual substrates separately and then reassemble them at the destination. This would be useful when the surface of the mother substrate is crowded with many substrates and only narrow passageways exist that are slightly larger than an individual substrate.

FIG. 37*b* illustrates a "corner substrate" 37-6 can be placed on the opposite surface of the mother substrate to increase the effective height of the edge. As the daughter substrate 37-3 is being moved in the direction 37-5, the substrate 37-4 is moved until it overhangs the edge of the mother substrate 37-2. When the center of mass of the substrate 37-4 passes beyond the edge of the mother substrate 37-2, the edge Coulomb forces of the mother substrate 37-2 in combination with the edge Coulomb forces of the corner substrate 37-6 and the bottom surface Coulomb forces of the substrate 37-4 attract the two substrates together. Meanwhile the bottom surface Coulomb forces of the substrate 37-4 juxtaposed to the top surface of the mother substrate 37-2 repel each other. This causes the substrate 37-4 to rotate (see arrow) clockwise around the edge of the mother substrate 37-2. After the flip, the surface of the substrate 37-4 is parallel to the edge of the mother substrate 37-2. The edge Coulomb forces of the mother substrate 37-2 in combination with the edge Coulomb forces of the corner substrate 37-6 help hold the bottom surface Coulomb forces of the substrate 37-4 in place. Then, as shown in FIG. 37*b*, the daughter substrate 37-3 is positioned with one of its edges lined up with the edge of the mother substrate 37-2 and the bottom of the substrate 37-4. Now, the substrate 37-4 is rotated counterclockwise (see arrow) until the substrate 37-4 is on the top surface of the daughter substrate 37-3 and becomes a grand daughter substrate. The top surface Coulomb forces of the daughter substrate 37-3 and the bottom surface Coulomb forces of the grand daughter substrate 37-4 are used to hold the two substrates together. This process of stacking the substrates can be continued until the structure given in FIG. 37*d* is created. Note that the structure can be deconstructed (reduced to individual substrates) in the reverse order.

In addition, more corner substrate can be stacked on the first corner substrate 37-6 to provide a wider edge. These corner substrates provide several features: 1) the area of the edge of the mother substrate is increased allowing more Coulomb islands to help stop and hold the substrate that was rotated; 2) vertical movement of the rotated substrate is improved since there are more Coulomb islands to create more Coulomb forces; 3) additional metallic contacts can become available to power up the rotated substrate; and 4) the corner substrate can move laterally to tilt the angle of the rotated substrate 37-4 away from 90°.

The stacking of the substrates of making daughter substrates into grand daughter substrates then great grand daughter substrates can continue for many levels. FIG. 37*d* illustrates a stacked substrate 37-7 which contains a daughter substrate 37-8 (the mother substrate not shown), the granddaughter substrate 37-9 and the great granddaughter substrates 37-10. Surface Coulomb forces between the upper two substrates are used to levitate the upper substrate 37-10 in the direction 37-11. FIG. 37*e* shows a separation 37-12. The separation will depend on the technology of the substrate (CMOS, SOI [Silicon on Insulator], etc.), if wafer bonding was used, on the area of the levitated substrate and if the wafer has special processing carried out on them to reduce or eliminate the formation portion to reduce the mass. Here the surface Coulomb forces are used between the substrates 37-9 and 37-10 to create the separation 37-12. FIG. 37*f* presents the system 37-7 when the daughter substrate 37-8 and the grand daughter substrate 37-9 are repelled from each other using surface Coulomb forces. The separation 37-13 is indicated. This is an interesting system in that the 37-10 substrate is levitated a separation 37-12 over the 37-9 substrate by using Coulomb forces between this first set of substrates. Then, the levitation of the 37-9 substrate over the 37-8 substrate causes a separation 37-13 that is caused by Coulomb forces between this second set of substrates. Since the 37-9 substrate is common to both the first and second set of substrates, the surface Coulomb forces between the second set of substrates must also support the gravitation force of the all substrates above it. The gravitation force of the multi-stacked substrates system will require large voltage magnitudes and large power dissipations to achieve large separations.

Figure 38:
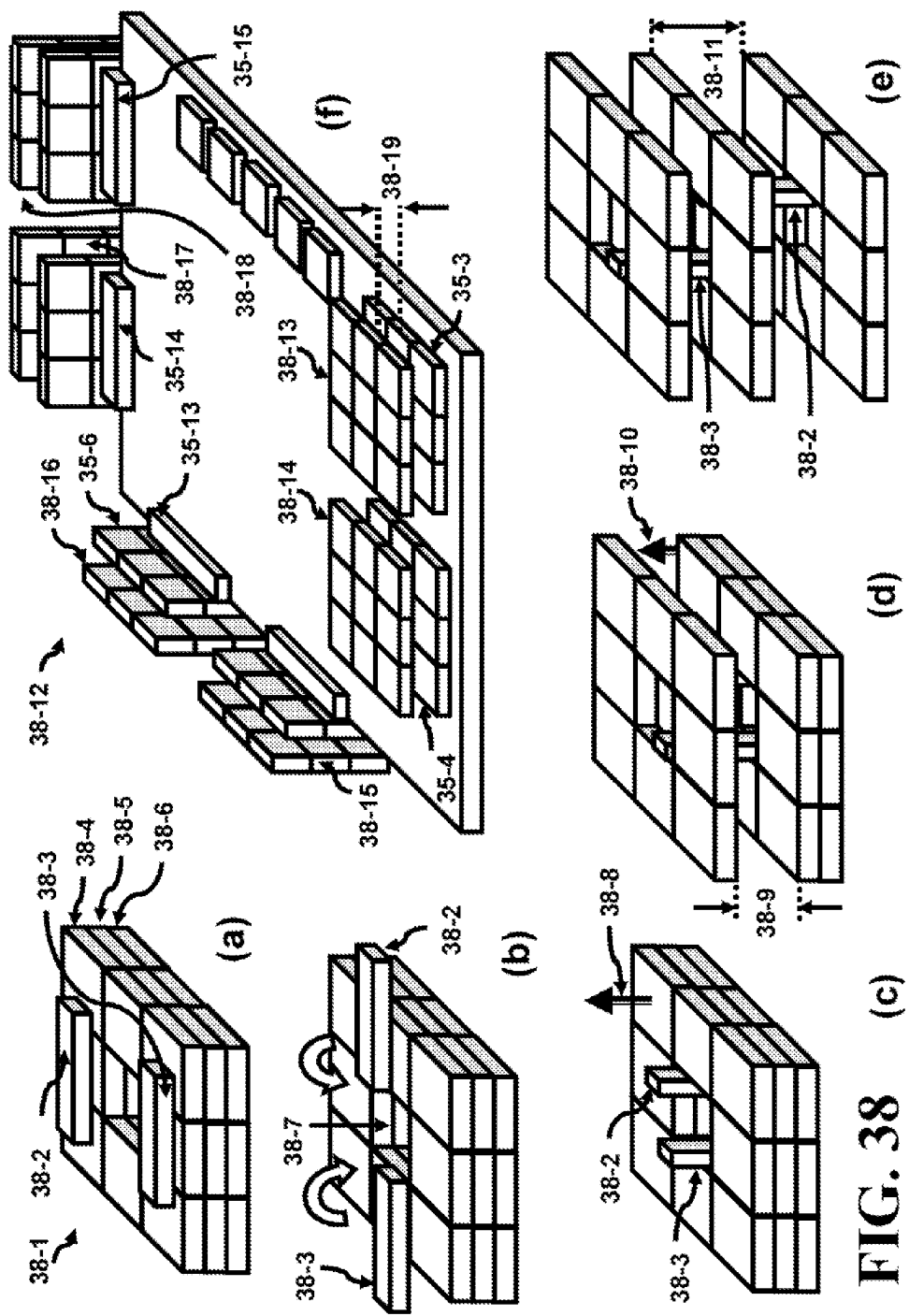
FIG. 38 reveals a) a stacked substrate, b) the preparation of flipping substrates, c) the substrates flipped into the open cavity, d) first raised substrate, e) second raised substrate and f) a 3-dimentional structure in accordance with the present invention.

The stacked substrate 38-1 is illustrated in FIG. 38*a* which consists of four layers of substrates (if these were on a mother substrate then the number of layers would be five), however, as shown: the mother substrate 38-6 is on the first layer consisting of several individual substrates held together by edge Coulomb forces; the daughter substrate is on the second layer 38-5; the grand daughter substrate 38-4 is on the third layer; and the great grand daughter substrates 38-2 and 38-3 are on the fourth layer. As indicated in FIG. 38*b*, the substrates 38-2 and 38-3 are repositioned using Coulomb forces near the opening 38-7 which exists on the three lower layers. Then these two substrates move into positions (not shown but described earlier) to prepare being rotated in the direction of the arrows into the opening 38-7. FIG. 38*c* illustrates the two substrates 38-2 and 38-3 now called "beam substrates" inside the opening 38-7. The beam substrates 38-2 and 38-3 use surface coulomb forces to rotate around the corner of the opening 38-7. The beam substrates can also have edge coulomb forces. With both beam substrates in place the grand daughter substrate 38-4 is levitated and raised upwards 38-8 using three sets of forces: 1) the surface to surface forces between the grand daughter substrate 38-4 and the daughter substrate 38-5; 2) the edge forces of the grand daughter substrate 38-4 and the surface forces of the beam substrates; and 3) the edge forces of the grand daughter substrate 38-4 and the edge forces of the beam substrates. Only two beam substrates are shown to simplify the diagram but additional ones can be used to increase the lifting ability. FIG. 38*d* illustrates the separation 38-9 which now can be increased by using the beam substrates as compared to the distance 37-12 given in FIG. 37*e*. This occurs because the beam substrates are perpendicular to the remaining substrates. In addition, the beam structures have the ability to carry signals between the separated substrates. FIG. 38*e* illustrates the daughter substrate 38-5 being raised with a separation 38-11. The beam substrates 38-2 and 38-3 are identified. Again comparing this result to FIG. 37*f*, the separation can be increased. Thus, the beam substrate help in several ways: 1) the separation between raised substrates can be increased; 2) heat planes can be inserted of between the substrates to decrease the thermal conductance; 3) the beam substrate can carry signals, power, and heat; 4) the beam substrates provide mechanical support; 5) the beam substrates can carry fluids and gases for LoC systems; 6) the beam substrate can contain Boolean and analog circuitry forming a VLSI circuit; and 7) complex 3-D structures can be built under the control of a FSM and program contained within the stacked substrate paving the way for a 3-D automaton.

A dense package or stacked substrate such as that shown in 38-1 can be assembled into a structure as shown in FIG. 38*e* or another complex structure under the control of a FSM (Finite State Machine). By way of example only three aligned substrates and two beam substrates were used, but any number may have been used. The CAD (Computer Aided Design) tools will be required to offer the full flexibility of this self assembly technique. The CAD tool provides instructions that can be stored in memory. The instructions can be stored in memory (non-volatile) and the FSM and memory can be inside the stacked substrate. The structure illustrated in FIG. 38*e* for example can be further changed in real time to adapt to changing conditions. The substrates 38-4 through 38-6 are identical to simply the discussion. Note that the substrate 38-4 consists of eight substrates that are held together by edge Coulomb forces and are identically shaped. However, these eight substrates can each have a different area. In that case, a substrate like 38-4 can have a variety of different areas. However, the stacked substrates would not necessarily be aligned on all edges as indicated in FIG. 38*a*. In addition, the beam substrates can also be assembled on the outside edges of the stacked substrates wherever the edges do line up.

FIG. 38*f* illustrates the antenna given in FIG. 35*b* with a grand daughter substrate levitated over the daughter antenna substrate. The grand daughter substrates are 38-13 through 38-17 which could be patch antennas fabricated using SOI or some other very low loss substrate. The daughter substrates 35-3 through 35-8 could be ground planes which are separated by the distance 38-19 and can be adjusted by using the beam substrates. Not illustrated are the beam substrates that can be used to transfer the signals received/sent to the patch antenna; this has been done to simply the diagram. The ground planes can have a larger area than the patch antenna. Several variations of this design are possible: each pair of the daughter substrates 35-3 and 35-4 can be combined into one ground plane and the two patch antennas 38-14 and 38-13 can sit on a larger ground plane; and the ground plane can hold additional antenna substrates so that the dipole can be reconfigured using Coulomb forces while in the orthogonal position.

FIG. 39*a* depicts a substrate stack 39-1 where each layer of the stack has an inductor 39-2 through 39-4 inside the substrate. The middle substrate 39-6 is placed in between top 39-5 and bottom 39-7 substrate. The distances 39-9 and 39-10 indicate the relative position of the middle substrate to the two other substrates. The top view of the metallic substrate 39-8 that forms part of the middle substrate 39-6 is shown in FIG. 39*b*. The I/O connection 39-15 is the metallic contact that coupled to the adjoining metallic substrate. The Coulomb islands 39-11 are used to create the edge Coulomb forces used to hold the metallic substrates together. Of course, multiple metallic contacts and Coulomb islands can be formed but are not indicated to simplify the diagram. The side view of FIG. 39*b* as indicated by the arrow 39-12 and presented in FIG. 39*c*. The metallic substrate is formed by a back to back connection holding two substrates. The component portion 24*a* and 2-4*b* contains the metallic traces 39-13 inside the substrate. Four levels of metal are used in this example, but more or less metal levels can be used. Coulomb islands 39-14 are indicated in the 24*b* portion. A technology (for example, SOI) that can minimize the loss would be beneficial in this case. Furthermore, the thickness of the foundation portion 2-2 can be reduced to help reduce the loss and mass. In addition, the placement of the Coulomb islands 39-14 should be decreased near the metal trace forming the inductor to further reduce the losses. These metallic substrates can also be used for the antenna substrates that were mentioned earlier. The I/O connection 39-15 is also shown. FIG. 39*d* indicates a series coupling of the inductors 39-2 through 39-4 that were shown in FIG. 39*a* forming a cylindrical inductor while FIG. 39*e* indicates a possible transformer circuit configuration where the upper two inductors 39-2 and 39-3 have a mutual coupling of $M_1$ and the lower two inductors 39-3 and 39-4 have a mutual coupling of $M_2$. The distances 39-9 and 39-10 can be changed by using Coulomb forces to move the middle substrate 39-6 in the vertical direction to change the distances and therefore the mutual inductance of the transformer. Many other inductor/transformer circuits can be created.

Finally, it is understood that the above description are only illustrative of the principle of the current invention. It is understood that the various embodiments of the invention, although different, are not mutually exclusive. In accordance with these principles, those skilled in the art may devise numerous modifications without departing from the spirit and scope of the invention. For example, the individual substrates held together by edge Coulomb forces may be comprised substrates using various materials fabricated in a variety of technologies. Also, the Coulomb forces can hold substrates together even after the power supply has been disconnected from the system. This occurs if the islands are the non-volatile type since these islands can hold the charge indefinitely and therefore can maintain the force indefinitely. The connect substrate can also be used as a low impedance switch when connected and offering an infinite impedance when the connect substrate is detached. The devices and circuits of a manufacturing technology can also be incorporated into all of the substrates (for example, the corner, connect, and beam substrates) although this may have not been indicated in the drawings for simplification. The various shapes of the metallic antenna on substrates for antenna formation may be, but not limited to, circular, hexagonal, stripe, rectangular or polygonal shaped. The inventive aspects that are used in the antenna formation are applicable to other system designs using other substrates. The antenna can also be designed for lower carrier frequencies than 75 GHz since Electrically Small Antenna (ESA) can be designed. Other examples of antenna, but not an exhaustive list, include omni directional and circular polarized antennas. The inductors have been shown using only one turn and the same metal level; however, the inductors can be multi-turns and can have portions of the metal layers on different levels to avid crossovers and crossunders in the metal layers. The invention can be practiced using the CMOS, MOS, BiCMOS, SOI, MCM, MEMS or BJT technology. The materials to form devices can be silicon, plastic, GaAs, SiGe and SiN.

APPENDIX TO EXAMINER

The published paper "Fundamental Limitations of Small Antennas", Proceedings of the IRE, 1947, pg. 1479-1484, by Wheeler, provides information if the dimensions of the antenna are much less than the wavelength.

In a published paper, "Computation Methods for Design and Control of MEMS Micromanipulator Arrays", Computing in Science and Eng., January-March 1997, (Vol. 4, No. 1), pp. 17-29, Bohringer et al. In pp. 20, right col., $1^{st}$ para., "The other side of the actuator consists of a denser grid above an aluminum electrode. If a voltage is applied between silicon substrate and electrode, the dense grid above the electrode is pulled downward by the resulting electrostatic force. Simultaneously the other side of the device (with the tips) is deflected out of the plane by several μm. Hence an object can be lifted and pushed sideways by the actuator." The actuator is a level with a fulcrum. Bohringer uses the lever to move a substrate on the surface of the array. An electrostatic force pulls on one end of the lever while the other end of the lever moves upwards and physically makes contact with the bottom of the substrate (see FIG. 7). The friction of the physical contact movement of the lever is transferred to the substrate and moves the substrate across the surface. Also, see FIG. 14 which uses the actuator array to move and rotate silicon chips. Our invention does not require friction to perform the movement, it avoids friction.

In a published paper, "Microassembly Technologies for MEMS", Proc. SPIE Micromaching and Microfabrication, Santa Clara, Calif. Sep. 21-22, 1998 by Cohn et al., show a process flow for dry electrostatic self-assembly in FIG. 9. The flow process is also shown in U.S. Pat. No. 5,355,577 issued Oct. 18, 1994 to Cohn. The trap voltage is applied to a single bottom plate of a base and the blocks are applied. The electric field from the bottom plate induces a charge into the blocks attracting them. The system is vibrated until the blocks stochastically move into their positions. Once in position, the blocks are solidly attached to the base by a metal deposition. Our invention, among many other things, incorporates adjustable charge plates into the blocks giving them the ability to be independently controlled to generate controlled forces that can systematically assemble and furthermore re-assemble or reconfigure a system.

In a published paper, "Novel Electrostatic Repulsive Forces in MEMS Applications by Nonvolatile Charge Injection", The $15^{th}$ IEEE hit. Conf. MEMS, 2002, pg. 598-601, by Liu et al. They propose in the lower left column of pp. 598 "using nonvolatile charge injection to realize effective electrostatic repulsion force actuation. The MEMS structures are integrated with Electrically Erasable Programmable Read Only Memory (EEPROM) cells and are connected with the floating gate of the EEPROMs." In addition, in the last paragraph in the lower left column of pp. 599 follows: "The devices for electrostatic repulsion force demonstrate consist of pairs of a parallel beams of various lengths (160-400 mm) with 1.6 mm (design rule minimum) gap. The beams are anchored at both ends by oxide. Each beam connects to the floating gate of an EEPROM cell for charge injection and monitoring." One of the co-authors holds U.S. Pat. No. 6,597,048 issued Jul. 22, 2003 to Kan which describes in their abstract: "A method of injecting electrostatic charges into opposing elements of MEMS structures to produce repulsing forces between the elements." The entire structure or opposing elements are formed and remains attached to the one substrate for both reference. Our invention, among many other things: incorporates Coulomb islands in juxtaposed substrates that are used to control an independent movement of detached levitated substrates; and proposes a plurality of EEPROMs connected to a charged structure where one EEPROM can charge the structure negatively while the second EEPROM can charge the structure positively.

In a published paper, "Survey of sticking effects for micro parts handling", Intelligent Robots and Systems 95, Proc. 1995 IEEE/RSJ Inter, Conf. Aug. 5-9, 1995, pp. 212-217 by R. Fearing offers an insightful look into the sticking effect or stiction of micro components.

U.S. Pat. No. 4,947,228 issued Aug. 7, 1990 to Gabara describes a single via contact through the entire substrate to the back surface of the substrate. U.S. Pat. No. 5,298,800 issued Mar. 29, 1994 to Dunlop et. al. describes a closed loop link adjusting the intensity of light in a fiber. U.S. Pat. No. 5,396,195 issued Mar. 7, 1995 to Gabara describes a LC CMOS tank circuit. U.S. Pat. No. 5,708,389 issued Jan. 13, 1998 to Gabara describes a circuit for transferring digital data through a capacitive interconnect. Both U.S. Pat. No. 6,281, 590 issued Aug. 28, 2001 and U.S. Pat. No. 6,465,336 issued Oct. 15, 2002 to Gabara et. al. describe the use of an MCM with traces to bypass the input and output circuitry between two substrates and make a permanent connection. Please see FIG. 29b of this specification. The traces are located in the grand daughter substrate 29-9 and the substrate is levitated into position by Colomb forces to make a temporary connection. The "connect substrate" can then be detached and used to provide a metallic path between two different daughter substrates as a metallic switch for antennas, for example.

A system for electrostatic bonding is described in U.S. Pat. No. 6,638,627 issued Oct. 28, 2003 to Potter. Charges are placed into a first region of a first unit at least adjacent to a first region of a second unit. A bond between these regions is formed between the bound charge of the first unit and the induced charge of the second unit. A second U.S. Pat. No. 6,841,917 issued Jan. 11, 2005 to Potter as stated in the abstract, describes "an electrostatic interaction system includes a first stricture having a first fixed electrostatic charge and a second stricture having a second fixed electrostatic charge. The polarity of the first and second fixed electrostatic charges determines a positional relationship of the first structure to the second structure." Our invention, among many other things: forms pockets of islands in two substrates where each island can be adjusted independently of each another allowing lateral motion, detachment, attachment, rotation, etc.

A proof mass is caused to levitate by electrostatic repulsion and is described in U.S. Pat. No. 7,225,674 issued Jun. 5, 2007 to Clark. In Col. 8, line 35-39, "In addition, if both the side electrodes/proof mass and the stabilizing electrodes are charged to the same potential, there is no danger of short-circuiting, in contrast to floating devices based upon the attraction of opposite charges." Clark uses a charged proof mass that is non-insulated. The oxide surrounding this proof mass is a sacrificial layer. During the MEMS processing step of releasing the proof mass, the sacrificial oxide layer is etched away thereby exposing the proof mass. The exposed proof mass can now make electrical contact with the stabilizing electrode and short out. Interestingly, the proof mass is charged up initially by this connection. For example, see Col. 5, lines 28-36. "One convenient method for charging the conductors involves the application of a voltage to conductors 3 and 7, thereby delivering charge to conductor 5 in contact therewith. However, when charged, conductor 5 will repel from both 3 and 7 to float as depicted in FIG. 1b. Thus, conductor 5 remains in electrical contact with conductor 3 for so long as is necessary for conductor 5 to accumulate sufficient charge to repel or "float" and break electrical contact with conductors 3." Once the electrical contact is broken the conductor 5 levitates. Our invention, among many other things: forms a plurality of islands in the levitated substrate where each island can be adjusted independently of each another allowing the same structure to be placed in motion, attachment, rotation, detachment, motion, etc.

U.S. Pat. No. 7,250,826 issued Jul. 31, 2007 and U.S. Appl. 20070176704 published Aug. 2, 2007 to Gabara describes a way of reducing die eddy current loss within a coil or inductor by placing a plurality of coils in parallel.

U.S. Appl. 2007018739 published Jan. 25, 2007 to Gabara describes a mechanical lifting of an inductor in of a structure to decrease the eddy current loss in the substrate. Please see FIG. 15a of this specification. The substrate 15-2 containing the inductor has been lifted away the mother substrate 15-3 using Coulomb forces. In addition, material has been etched away from the far side of the inductor to further cut on eddy current losses in the substrate.

U.S. Appl. 20060122504 published Jul. 8, 2006 to Gabara et. al. describe a charged capacitor that is used to power a independent unit. Once the capacitor is placed in the system, it remains stationary for the life of the system. Please see FIG. 29c of this specification. The substrate 29-26 contains a capacitor 29-27 that is charged when the system 29-24 is in contact with the mother substrate and discharges when the substrate 29-24 is detached from the mother substrate. The charged capacitor can be detached from the substrate 29-25 and moved to another daughter substrate to provide additional power to a second substrate.

U.S. Appl. 20040080456 published Apr. 29, 2004 to Tran describes "a selectable antenna array formed from a planar field of microelectro-mechanical switches (MEMSs)" in paragraph 2. Paragraph 12 provides: "The switch is fabricated using silicon nitride as the armature structural layer and silicon dioxide as a sacrificial layer supporting the armature during fabrication". All MEMSs devices are permanently anchored into position once the array is fabricated. This means that the freedom to provide a feedpoint anywhere on the array is limited. In paragraph 73, Tran indicates that "Theoretically, there are no limitations to the shape of the active element. Practically, the shape is limited to the placement of feedpoints, . . . " In paragraph 75, Tran reinforces this limitation again, "Practically, the position of the active elements is limited to the position of the feedpoint 202, or selectively engageable feedpoints in the field 101." Our invention, among many other things: allows a conductive path to be formed from the RF front end to the feedpoint by positioning antenna substrates on the mother substrate to where the feedpoint is located.

What is claimed is:

1. An apparatus comprising:
   a first daughter substrate with a first cavity in a first bottom surface, and a first top surface with a plurality of first Coulomb islands;
   a second daughter substrate with a second cavity in a second bottom surface, and a second top surface with a plurality of second Coulomb islands;
   the first and second top surfaces adjacent to a top surface of a mother substrate with a plurality of third Coulomb islands;
   a first drop of a first fluid with a contact angle greater than 90° in the first cavity;
   a second drop of a second fluid in the second cavity;
   the first drop overhangs an edge of the first daughter substrate;
   the second drop overhangs an edge of the second daughter substrate; and
   all Coulomb islands have a charge, whereby
   at least one Coulomb force levitates the first and second daughter substrates over the top surface of the mother substrate.

2. The apparatus of claim 1, whereby
   a first surface of the first drop is in contact with a second surface of the second drop.

3. The apparatus of claim 1, further comprising:
   a pump that extracts a portion of the fluid from either the first or second drop then adds a different fluid to alter properties of the first or second drop.

4. The apparatus of claim 1, whereby
   the second drop has a contact angle greater than 90°.

5. The apparatus of claim 1, whereby
   the second drop has a contact angle equal to or less than 90°.

6. The apparatus of claim 1, further comprising:
a control unit that adjusts the charge on the Coulomb islands.

7. The apparatus of claim 6, further comprising:
a joystick that supplements the control unit; and
a microscope to view an interface formed between the first and second drops.

8. The apparatus of claim 6, whereby
the control unit causes the first drop to tangentially rub the second drop.

9. The apparatus of claim 6, whereby
the control unit adjusts a normal force applied between the first drop and the second drop.

10. The apparatus of claim 6, whereby
the control unit applies a voltage potential between the first drop and the second drop.

11. The apparatus of claim 6, whereby
the control unit forces a current to flow between the first drop and the second drop.

12. The apparatus of claim 6, whereby
the control unit alters a content of either the first drop or the second drop.

13. An apparatus comprising:
a drop of a first fluid in a cavity in a bottom surface of a first substrate;
a top surface of the first substrate adjacent to a top surface of a mother substrate; and
a means for using Coulomb forces to levitate and move the first substrate over the top surface of the mother substrate.

14. The apparatus of claim 13, further comprising:
a drop of a second fluid in a cavity in a bottom surface of a second substrate;
a top surface of the second substrate adjacent to the top surface of the mother substrate; and
a means for using Coulomb forces to levitate and move the second substrate over the top surface of the mother substrate.

15. The apparatus of claim 14, further comprising:
a control unit with a means of adjusting the Coulomb forces.

16. The apparatus of claim 14, whereby
a surface of the first drop is in contact with a surface of the second drop.

17. The apparatus of claim 16, whereby
a control unit moves the surface of the first drop to tangentially rub the surface of the second drop.

18. The apparatus of claim 14, further comprising:
a pump that extracts a portion of the fluid from either the first or second drop then adds a different fluid to alter properties of the first or second drop.

19. An apparatus comprising:
a first substrate with a first cavity in a first bottom surface, and a first top surface with a plurality of first Coulomb islands;
the first top surface adjacent to a top surface of a mother substrate with a plurality of second Coulomb islands;
a drop of a first fluid in the first cavity; and
all Coulomb islands have a charge, whereby
at least one Coulomb force levitates the first substrate over the top surface of the mother substrate.

20. The apparatus of claim 19, further comprising:
a second substrate with a second cavity in a second bottom surface, and a second top surface with a plurality of second Coulomb islands;
the second top surface adjacent to the top surface of the mother substrate;
a drop of a second fluid in the second cavity; and
all remaining Coulomb islands have a charge, whereby
at least one Coulomb force levitates the second substrate over the top surface of the mother substrate.

21. The apparatus of claim 19, further comprising:
a control unit that adjusts the charge on the Coulomb islands.

* * * * *